United States Patent
Rowe et al.

(10) Patent No.: US 10,960,018 B2
(45) Date of Patent: Mar. 30, 2021

(54) METHODS AND COMPOUNDS FOR STIMULATING READ-THROUGH OF PREMATURE TERMINATION CODONS

(71) Applicant: The UAB Research Foundation, Birmingham, AL (US)

(72) Inventors: Steven Rowe, Birmingham, AL (US); David M. Bedwell, Hoover, AL (US); Venkateshwar Mutyam, Birmingham, AL (US); Ming Du, Birmingham, AL (US); Kim M. Keeling, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 16/093,516

(22) PCT Filed: Apr. 17, 2017

(86) PCT No.: PCT/US2017/027982
§ 371 (c)(1),
(2) Date: Oct. 12, 2018

(87) PCT Pub. No.: WO2017/181193
PCT Pub. Date: Oct. 19, 2017

(65) Prior Publication Data
US 2019/0125775 A1    May 2, 2019

Related U.S. Application Data

(60) Provisional application No. 62/323,045, filed on Apr. 15, 2016.

(51) Int. Cl.

| | |
|---|---|
| *A61K 31/70* | (2006.01) |
| *A01N 43/04* | (2006.01) |
| *A61K 31/704* | (2006.01) |
| *A61K 45/06* | (2006.01) |
| *C12Q 1/68* | (2018.01) |
| *A61K 31/165* | (2006.01) |
| *A61K 31/45* | (2006.01) |
| *A61K 31/4184* | (2006.01) |
| *A61P 11/00* | (2006.01) |
| *A61K 31/443* | (2006.01) |
| *A61K 31/47* | (2006.01) |
| *A61K 31/4745* | (2006.01) |
| *A61K 31/498* | (2006.01) |

(52) U.S. Cl.
CPC .......... *A61K 31/704* (2013.01); *A61K 31/165* (2013.01); *A61K 31/4184* (2013.01); *A61K 31/443* (2013.01); *A61K 31/45* (2013.01); *A61K 31/47* (2013.01); *A61K 31/4745* (2013.01); *A61K 31/498* (2013.01); *A61K 45/06* (2013.01); *A61P 11/00* (2018.01); *C12Q 1/68* (2013.01)

(58) Field of Classification Search
None
See application file for complete search history.

(56) References Cited

U.S. PATENT DOCUMENTS

| | | |
|---|---|---|
| 2005/0233327 A1 | 10/2005 | Welch |
| 2014/0135296 A1 | 5/2014 | Deretic |
| 2015/0080431 A1 | 3/2015 | Van Goor et al. |

FOREIGN PATENT DOCUMENTS

| | | |
|---|---|---|
| EP | 2149378 | 8/2014 |

OTHER PUBLICATIONS

Valayannopoulos, Vassili, and Frits A. Wijburg. "Therapy for the mucopolysaccharidoses." Rheumatology 50.suppl_5 (2011): v49-v59.*
Zhang et al. Molecular Therapy (2004), vol. 10, pp. 990-1000.*
Zhou et al. Planta. Med. (2009), vol. 75, pp. 1580-1585.*
Tanaka et al. Cancer Research (1993), vol. 53, pp. 2884-2887.*
Venkateshwar Mutyam, Discovery of Clinically Approved Agents that Promote Suppression of Cystic Fibrosis Transmembrane Conductance Regulator Nonsense Mutations, American Journal of Respiratory and Critical Care Medicine, vol. 194, No. 9, Nov. 1, 2016.
Blaine Copenheaver, International Search Report and Written Opinion, Int'l Search Authority (PCT/US17/27982), dated Sep. 21, 2017.

* cited by examiner

*Primary Examiner* — Patrick T Lewis
(74) *Attorney, Agent, or Firm* — Thomas G. Peterson; Maynard Cooper & Gale

(57) ABSTRACT

The present disclosure provides compositions and methods for treating and/or preventing diseases and conditions associated with premature termination mutations. The methods disclosed herein comprise the step of administering to the subject a therapeutically effective dose of a compound described herein that induces read-through of the premature termination codon. The methods of the present disclosure may further comprise treating the subject with enzyme replacement therapy wherein the enzyme replacement therapy is selected for the disease or condition to be treated. Furthermore, the present disclosure provides method of pharmacologically suppressing premature termination codons in a subject in need of such suppression.

24 Claims, 28 Drawing Sheets
Specification includes a Sequence Listing.

NMDI-1　　　　　NMDI-14

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: synthesized sequence

<400> SEQUENCE: 1

```
atagttcttt gagaaggtgg a                                      21

<210> SEQ ID NO 2
<211> LENGTH: 21
<212> TYPE: DNA
<213> ORGANISM: Artificial Sequence
<220> FEATURE:
<223> OTHER INFORMATION: sythesized sequence

<400> SEQUENCE: 2
aaatcccaat gacatgcagg a                                      21
```

METHODS AND COMPOUNDS FOR STIMULATING READ-THROUGH OF PREMATURE TERMINATION CODONS

CROSS-REFERENCE TO RELATED APPLICATIONS

This application is a national stage under 35 U.S.C. 371 of International Application No. PCT/US2017/191193, with an international filing date of Apr. 17, 2017 (currently published). International Application No. PCT/US2017/191193 cites the priority of US Provisional Application No. filed 62/323,045, filed Apr. 15, 2016.

STATEMENT REGARDING GOVERNMENT SUPPORT

This invention was made with government support under contract number Cystic Fibrosis Foundation # ROWE13XXO; NIH P30 #P30 DK072482. The government has certain rights in the invention.

BACKGROUND OF THE DISCLOSURE

Cystic fibrosis (CF) is an autosomal recessive disorder caused by mutations in the gene encoding the CF transmembrane conductance regulator (CFTR), an anion channel primarily localized to the apical membranes of secretory epithelial cells lining the airways and multiple organs. Among the most common mutation class, premature termination codons (PTCs) in CFTR lead to translation termination due to an in-frame nonsense mutation in the coding sequence, resulting in nonfunctional CFTR protein (Welsh M J, et al. Cell; 73:1251-1254; 1993). PTCs are the proximate cause of ~11% of CF causing alleles and many other genetic diseases (Sloane P A, et al. *Current opinion in pulmonary medicine;* 16:591-597; 2010).

Efforts to develop treatments for CF patients with nonsense mutations have focused on strategies to promote termination suppression (also known as translational readthrough) of PTCs. Translational read-through is accomplished when an amino acid carried by near-cognate aminoacyl tRNA is inserted into a polypeptide chain at the erroneous stop codon, allowing translation to continue, and partially restoring full-length, functional protein (Bedwell D M, et al., *Nat Med;* 3:1280-1284; 1997; Howard M, et al, *Nat Med;* 2:467-469; 1996). Several phatmacologic approaches to induce read-through have been discovered, yet none has yielded an optimal combination of efficacy and safety. For instance, in vitro work has demonstrated that certain aminoglycosides can promote read-through and have been tested in clinical trials with mixed results (Clancy J P, et al., *Am J Respir Crit Care Med;* 163:1683-1692; 2001; Clancy J P, et al., *American journal of respiratory cell and molecular biology;* 37:57-66; 2007; Wilschanski M, et al., *N Engl J Med;* 349:1433-1441; 2003; Wilschanski M, et al., *N Engl J Med;* 349:1433-1441; 2003; Wilschanski M, et al., Am J Respir Crit Care Med; 161:860-865; 2000; Sermet-Gaudelus I, et al., *BMC Med;* 5:5; 2007), but are not well suited for long-term use. Synthetic aminoglycoside derivatives optimized for translation suppression of the eukaryotic ribosome have exhibited improved read-through and reduced toxicity when compared in vitro. Ataluren (formerly PTC124) is an orally bioavailable small-molecule that induces readthrough. In a sub-set analysis, ataluren demonstrated a modest treatment benefit in CF patients not using chronic inhaled tobramycin, which interferes with its effect (Kerem E, et al., *Lancet Respir Med* 2014), a finding currently under prospective evaluation.

An attractive strategy for development of non-toxic, orally bioavailable, and efficacious read-through agents is to evaluate the utility of compounds already approved for clinical use, thus facilitating rapid evaluation of promising compounds in humans. The present disclosure provides new compounds for use in treating diseases and conditions mediated, at least in part, by the presence of a PTC. Such diseases and conditions include, but are not limited to, genetic conditions in which a PTC codon produces a non-functional polypeptide, such as but not limited to, CF. The present disclosure also provides methods for increasing the stability level of a mRNA transcript that is involved, at least in part, in a disease or condition, wherein the mRNA transcript contains a missense mutation as a result of readthrough suppression by a compound of the present disclosure. Such diseases and conditions include, but are not limited to, genetic conditions in which a PTC codon produces a non-functional polypeptide, such as but not limited to, CF. The present disclosure further provides compounds for use in the above methods and pharmaceutical compositions comprising such compounds.

BRIEF DESCRIPTION OF THE FIGURES

For all figures if not specifically mentioned otherwise, *P<0.05, P<0.01, *P<0.001, ****P<0.0001

FIG. 2A shows a representative tracing of conductance.

DETAILED DESCRIPTION

Definitions

Figure 1A:
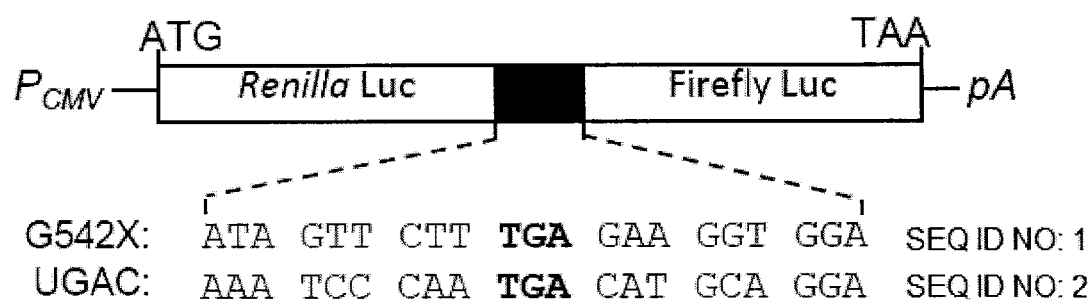
FIG. 1A shows a diagram of the dual luciferase constructs showing the CFTR PTC context (G542X and UGAC) and WT inserted between *renilla* and firefly luciferase.

As used herein, the term "alkyl", whether used alone or as part of a substituent group, includes straight hydrocarbon groups comprising from one to twenty carbon atoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)CH(CH$_3$)$_2$, —CH(CH$_2$CH$_3$)CH(CH$_3$)CH(CH$_3$)(CH$_2$CH$_3$), and others. The phrase also includes cyclic alkyl groups such as cyclopropyl, cyclobutyl, cyclopentyl, cyclohexyl, cycloheptyl, and cyclooctyl and such rings substituted with straight and branched chain alkyl groups as defined above. The phrase also includes polycyclic alkyl groups such as, but not limited to, adamantyl norbornyl, and bicyclo[2.2.2]octyl and such rings substituted with straight and branched chain alkyl groups as defined above.

As used herein, the term "alkenyl", whether used alone or as part of a substituent group, includes an alkyl group having at least one double bond between any two adjacent carbon atoms.

As used herein, the term "unsubstituted alkyl" and "unsubstituted alkenyl" refers to alkyl, alkenyl and alkynyl groups that do not contain heteroatoms.

As used herein, the term "substituted alkyl" and "substituted alkenyl" refers to alkyl alkenyl and alkynyl groups as defined above in which one or more bonds to a carbon(s) or hydrogen(s) are replaced by a bond to non-hydrogen or non-carbon atoms such as, but not limited to, an oxygen atom in groups such as alkoxy groups and aryloxy groups; a sulfur atom in groups such as, alkyl and aryl sulfide groups, sulfone groups, sulfonyl groups, and sulfoxide groups; a silicon atom in groups such as in trialkylsilyl groups, dialkylarylsilyl groups, alkyldiarylsilyl groups, and triarylsilyl groups; and other heteroatoms in various other groups.

As used herein the term "alkanoyl" refers to an alkylcarbonyl group, wherein the alkyl portion is substituted or unsubstituted.

As used herein the term "alkenoyl" refers to an alkenylcarbonyl group, wherein the alkenyl portion is substituted or unsubstituted.

As used herein, the terms "treatment", "treat" and "treating" refers a course of action (such as administering a conjugate or pharmaceutical composition) initiated after the onset of a symptom, aspect, or characteristics of a disease or condition so as to eliminate or reduce such symptom, aspect, or characteristics. Such treating need not be absolute to be useful.

As used herein, the term "in need of treatment" refers to a judgment made by a caregiver that a patient requires or will benefit from treatment. This judgment is made based on a variety of factors that are in the realm of a caregiver's expertise, but that includes the knowledge that the patient is ill, or will be ill, as the result of a disease or condition that is treatable by a method or compound of the disclosure.

As used herein, the term "in need of prevention" refers to a judgment made by a caregiver that a patient requires or will benefit from prevention. This judgment is made based on a variety of factors that are in the realm of a caregiver's expertise, but that includes the knowledge that the patient will be ill or may become ill, as the result of a disease or condition that is preventable by a method or compound of the disclosure.

As used herein, the term "individual", "subject" or "patient" refers to any animal, including mammals, such as mice, rats, other rodents, rabbits, dogs, cats, swine, cattle, sheep, horses, or primates, and humans. The term may specify male or female or both, or exclude male or female.

As used herein, the term "therapeutically effective amount" refers to an amount of a conjugate, either alone or as a part of a pharmaceutical composition, that is capable of having any detectable, positive effect on any symptom, aspect, or characteristics of a disease or condition. Such effect need not be absolute to be beneficial.

The following substituents are deemed to have the following structures when referred to in the present specification:

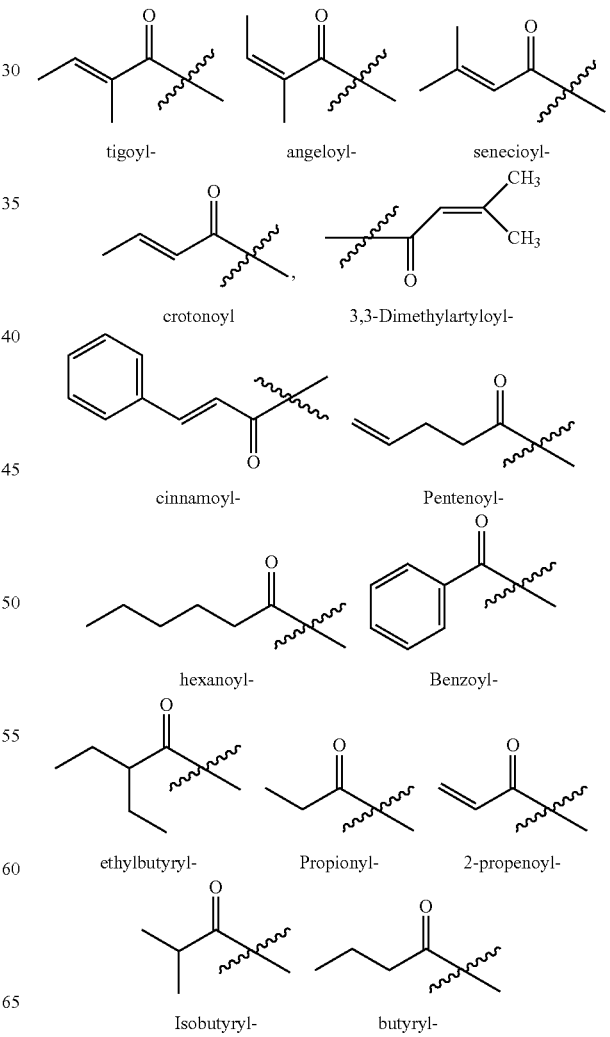

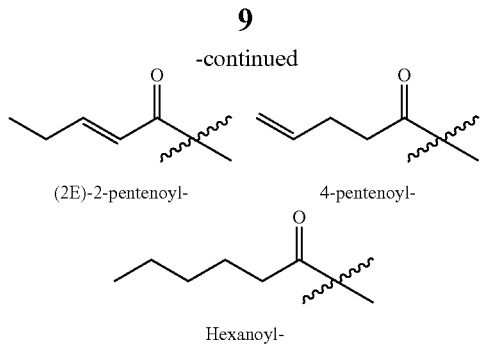

(2E)-2-pentenoyl-    4-pentenoyl-

Hexanoyl-

BACKGROUND

In the present study, a library of 1600 clinically approved compounds was evaluated using high throughput screening (HTS) to identify agents that suppress CFTR-PTC nonsense mutations. Two primary assays in parallel (one mechanistic, the other phenotypic) were conducted, and then confirmed for selected compounds in a series of secondary assays specific to read-through of CFTR nonsense mutations that have also proven predictive of clinical success. Through this process, several compounds were identified that induced read-through, including escin, a natural product that was efficacious and potent in a variety of primary human airway cells expressing CFTR premature termination alleles. These results indicated that the identified compounds have utility in treating nonsense-mediated genetic diseases, such as CF.

The agents that suppressed PTCs and induced read-through were a mixture of different medicinal classes (see Table 1). Categories that were represented by more than one agent were translational inhibitors (cyclohexamide), anti-inflammatories (colchicine, escin), anti-helmenthic (oxibendazole) and corticosteroids (prednicarbate, several related agents). The identification of translational inhibitors, which efficiently enhanced PTC suppression in both CFTR expression and functional assays, suggests that their ability to reduce translational fidelity occurs at doses prior to complete translation inhibition.

The present disclosure used two complementary assays coupled with a robust series of secondary testing focused on CFTR expression and function. In doing so, the problems encountered with luciferase stabilization, which has been reported to enhance firefly luciferase signal independent of read-through activity of PTCs, were avoided. In the secondary screen, a dual-luciferase read-through assay was used to validate initial data obtained in the HTS and allowed internal normalization of firefly luciferase to *renilla* luciferase to eliminate variability in mRNA abundance or translation initiation. The secondary evaluation of agents revealed the concordance between assays was generally high. The relatively weaker correlation between read-through (TECC) and function (Dual-Luciferase) assays might be due to the differences in how cell growth and translation affects the readouts detected in the assays. For example, in the TECC assay, the drug is added after the formation of monolayers when cell growth and translation is minimal. In contrast, in the dual-luciferase assay, drugs are added during cell seeding while growth and translation are both rapidly occurring. In addition, there are multiple intervening steps (i.e. ER retention, cAMP dependent-gating, etc.) between translation and CFTR-dependent ion transport that are likely to impact a precise correlation. Nevertheless, the relatively balanced number of compounds arising from each assay suggests that either approach could work as a primary screen when paired with an appropriate secondary evaluation strategy.

Among the eight lead compounds, escin exhibits an interesting profile and was one of few agents from the initial screen that also responded robustly to addition of $CFTR_{Inh}$-172. Interestingly, functional CFTR activity in both FRT and HBE cells following escin treatment was relatively strong compared to its read-through efficacy. This effect can be explained by the stabilization of mRNA transcripts and inhibition of non-sense-mediated RNA decay (NMD), which would be expected to synergistically improve function in the context of PTC suppression. Another possibility is escin's dual role as a CFTR agonist. Escin improves outcomes in patients with chronic venous insufficiency due to its effects on nitric oxide (NO) metabolism. NO is also involved in activation of CFTR channels and chloride currents in human lung epithelial cells, which may be a potential advantage of the compound. The present disclosure evaluated escin in CFTR-independent read-through constructs, CFTR deficient parental cells and F508del homozygous HBE cells. These experimental results clearly indicate that the effect of escin is not due to stimulation of CFTR activity outside of read-through.

There is prior experience with herbal agents in the treatment of CF. For example, curcumin has been shown to activate CFTR channels in vitro and may also have species-specific corrector activity. Two resveratrol oligomers derived from a Chinese medicinal plant were identified as CFTR inhibitors; others have been isolated from herbal plant *Rhodiola kirilowii*. This experience provides reason for optimism regarding the potential for escin to improve CF outcomes. Escin is highly suitable for human administration and has been previously used effectively for chronic venous insufficiency, exhibiting reasonable safety and pharmacokinetic properties (Suter A, et al., *Adv Ther;* 23:179-190; 2006).

Methods

As discussed above, the presence of a PTC codon results in a polypeptide that is prematurely truncated and lacks, either in whole or in part, the functional activity of its wild-type counterpart. When read-through of the PTC is stimulated, such as with the compounds of the present disclosure, an amino acid carried by near-cognate aminoacyl tRNA, or in some cases the cognate aminoacyl tRNA, is inserted into a polypeptide chain at the erroneous stop codon, allowing translation to continue, and partially restoring full-length, functional protein. As such, expression of the protein is increased. When a near-cognate aminoacyl tRNA is incorporated, the resulting polypeptide contains an amino acid that is not present in the wild-type polypeptide. In addition, the mRNA transcript itself, by virtue of the presence of the PTC, may be subject to NMD. NMD is a surveillance pathway that exists in all eukaryotes. Its main function is to reduce errors in gene expression by eliminating mRNA transcripts that contain PTCs. By decreasing the process of NMD, levels of the mRNA transcript containing the PTC are increased and thus available for translation in the presence of read-through stimulating compounds of the present disclosure. The present disclosure demonstrates that certain compounds disclosed not only stimulate read-through of the PTC codon, but also inhibit NMD, thereby increasing the stability and/or levels of mRNA transcripts containing a PTC.

In one embodiment, the present disclosure provides methods for treating a disease or condition mediated, at least in part, by the presence of a PTC. Such diseases and conditions include, but are not limited to, those in which a gene encoding a polypeptide contains a nonsense mutation resulting in the presence of a PTC codon in the polypeptide that results in the polypeptide being non-functional or having reduced function. Such diseases and conditions include, but are not limited to, CF, Duchenne muscular dystrophy, Becker muscular dystrophy, Spinal muscular atrophy, mucopolysaccharidosis I (including, Hurler syndrome, Hurler-Scheie syndrome and Scheie syndrome), Hemophilia, Hemophilia B, Usher syndrome, and cancer. PTCs in cancer include, but are not limited to, PTC in a tumor suppressor gene (such as but not limited to p53). Represented PTC codons in p53 include, but are not limited to, W53X, Q144X, W146X, Q192X, R196X, R213X, E298X and R306X.

The methods described herein comprise the step of administering to the subject a compound of the present disclosure. Such administration stimulates read-through of the PTC and/or increases the stability of the mRNA containing the PTC. In one aspect of this embodiment, such administration suppresses a naturally occurring PTC and stimulates read-through of the mRNA transcript containing the PTC. In another aspect of this embodiment, such administration increases the levels and/or stability of an mRNA transcript containing a PTC codon and suppresses a naturally occurring PTC and stimulates read-through of the mRNA transcript containing the PTC. In one aspect of this embodiment, the compound is administered in a therapeutically effective amount. Further, such methods may further comprise identifying a subject in need of such treatment, such as by identifying the presence of a PTC in the subject. In the methods described, the PTC may be any PTC known in the art. In another embodiment, the PTC is known or suspected of causing, at least in part, or being associated with a disease or condition. In another embodiment, the PTC is one associated with or one causing CF, such as but not limited to, R553X, G542X, W1282X, R1162X and Y122X. In another embodiment, the PTC is one associated with or one causing Hurler syndrome, such as but not limited to, W402X, Q70X, R628X, Q148X or E404X.

In another embodiment, the present disclosure provides methods for treating CF in a subject, wherein the CF is mediated, at least in part, by the presence of a PTC. In certain aspects of this embodiment, the PTC codon produces a non-functional polypeptide, such as but not limited to, the CTFR. Such method comprises the step of administering to the subject a compound of the present disclosure. Such administration stimulates read-through of the PTC and/or to increases the stability of the mRNA containing the PTC. In one aspect of this embodiment, such administration suppresses a naturally occurring PTC and stimulates read-through of the mRNA transcript containing the PTC. In another aspect of this embodiment, such administration increases the levels and/or stability of an mRNA transcript containing a PTC codon and suppresses a naturally occurring PTC and stimulates read-through of the mRNA transcript containing the PTC. In one aspect of this embodiment, the compound is administered in a therapeutically effective amount. Further, such methods may further comprise identifying a subject in need of such treatment, such as by identifying the presence of a PTC in the subject. In one aspect of this embodiment, the PTC is R553X, G542X, W1282X, R1162X, Y122X, Q637X, Q2X, S4X, Q39X or Q1313X. In another aspect of this embodiment, the PTC is G542X. In another aspect of this embodiment, the PTC is W1282X.

In another embodiment, the present disclosure provides methods for treating CF in a subject, wherein the CF is mediated, at least in part, by the presence of a PTC in the CFTR. In certain aspects of this embodiment, the PTC codon produces a non-functional polypeptide CFTR. Such method comprises the step of administering to the subject a compound of the present disclosure and further administering to the subject at least one of: i) an agent that increases the function of the CFTR polypeptide (for example, a CFTR potentiator); ii) an agent that increases the trafficking of the CFTR polypeptide (for example, a CFTR corrector); iii) an agent that inhibits NMD (for example, an NMD inhibitor); iv) an agent that that increases mRNA levels of the target mRNA (for example, a histone deacetylase inhibitor); v) an agent that increase general pulmonary function; or vi) a combination of the foregoing (each of the foregoing being considered a secondary agent). In this method, the administration of the compound stimulates read-through of the PTC and/or increases the stability of the mRNA transcript, thereby increasing the levels of CFTR polypeptide in the subject, while the administration of the agent that increases the function of the CFTR polypeptide improves the function of the CFTR produced by the read-through of the PTC, the agent that allows for improved trafficking of the CFTR polypeptide increases the levels of the CFTR polypeptide produced by the read-through of the PTC in functionally relevant locations (for example, the surface of the cell), and the agent that inhibits NMD and/or increases the levels of mRNA provide increased levels of mRNA for the action of the compounds of the present disclosure. In one aspect of this method, only an agent that increases the function of the CFTR polypeptide (for example, a CFTR potentiator) is administered with a compound of the present disclosure. In another aspect of this embodiment, only an agent that increases the trafficking of the CFTR polypeptide to the cell surface (for example, a CFTR corrector) is administered with a compound of the present disclosure. In another aspect of this embodiment, an agent that increases the function of the CFTR polypeptide and an agent that increases the trafficking of the CFTR polypeptide to the cell surface (for example, a CFTR potentiator and a CFTR corrector) is administered with a compound of the present disclosure. In another aspect of this embodiment, an agent that inhibits NMD (for example, a NMD inhibitor) is administered with a compound of the present disclosure. In another aspect of this embodiment, an agent that inhibits NMD and an agent that increases the trafficking of the CFTR polypeptide to the cell surface (for example, a CFTR corrector) is administered with a compound of the present disclosure. In another aspect of this embodiment, and an agent that increases the function of the CFTR polypeptide (for example, a CFTR potentiator) is administered with a compound of the present disclosure. In another aspect of this embodiment, an agent that increases the trafficking of the CFTR polypeptide to the cell surface (for example, a CFTR corrector) and an agent that increases the function of the CFTR polypeptide (for example, a CFTR potentiator) is administered with a compound of the present disclosure. In any of the foregoing embodiments, an agent that increases the levels of mRNA may be administered with a compound of the present disclosure. In any of the foregoing embodiments, an agent that increases general pulmonary function may be administered with a compound of the present disclosure.

In one aspect of this embodiment, the PTC is R553X, G542X, W1282X, R1162X, Y122X, Q637X, Q2X, S4X, Q39X or Q1313X. In another aspect of this embodiment, the PTC is G542X. In another aspect of this embodiment, the PTC is W1282X. In one aspect of this embodiment, the agent that increases the function of the CFTR polypeptide is VX-770, GP-5 or a combination of the foregoing. In one aspect of this embodiment, the agent that increases the trafficking of the CFTR polypeptide is VX-809, C1, C2, C1+C2, or a combination of the foregoing. In one aspect of this embodiment, the agent that inhibits NMD is NMDI-1, NMDI-9, NMDI-25, or NMDI-14. The administration of one or more agents may be prior to, contemporaneously with or after the administration of the compound of the present disclosure. In one aspect of this embodiment, the compound is administered in a therapeutically effective amount. Further, such methods may further comprise identifying a subject in need of such treatment, such as by identifying the presence of a PTC in the subject.

In another embodiment, the present disclosure provides methods for treating mucopolysaccharidosis I (including, but not limited to, Hurler syndrome, Hurler-Scheie syndrome and Scheie syndrome) in a subject, wherein any of the foregoing are mediated, at least in part, by the presence of a PTC in the α-Liduronidase polypeptide. In certain aspects of this embodiment, the PTC codon produces a non-functional α-Liduronidase polypeptide. Such method comprises the step of administering to the subject a compound of the present disclosure and optionally further administering to the subject an agent that inhibits NMD. In this method, the administration of the compound stimulates read-through of the PTC and/or increases the stability of the mRNA transcript, thereby increasing the levels of α-Liduronidase polypeptide in the subject. When an agent that inhibits NMD is administered, such agent increases the levels of the mRNA encoding the α-Liduronidase polypeptide. In one embodiment, the mucopolysaccharidosis I is Hurler syndrome.

In one aspect of this embodiment, the PTC is W402X, Q70X, R628X, Q148X, E404X, Y343X or Q548X. In another aspect of this embodiment, the PTC is W402X. In another aspect of this embodiment, the PTC is Q70X. In one aspect of this embodiment, the agent that inhibits NMD is NMDI-1, NMDI-9, NMDI-25, or NMDI-14. The administration of one or more agents may be prior to, contemporaneously with or after the administration of the compound of the present disclosure. In one aspect of this embodiment, the compound is administered in a therapeutically effective amount. Further, such methods may further comprise identifying a subject in need of such treatment, such as by identifying the presence of a PTC in the subject.

In another embodiment, the present disclosure provides methods for pharmacologically suppressing PTC in a subject. Such method comprises the step of administering to the subject a compound of the present disclosure. Such administration stimulates read-through of the PTC. In one aspect of this embodiment, the compound is administered in a therapeutically effective amount. Further, such methods may further comprise identifying a subject in need of such treatment, such as by identifying the presence of a PTC in the subject.

In another embodiment, the present disclosure provides methods for pharmacologically suppressing PTC associated with CF in a subject. Such method comprises the step of administering to the subject a compound of the present disclosure. Such administration stimulates read-through of the PTC associated with CF. In one aspect of this embodiment, the PTC is R553X, G542X, W1282X, R1162X, Y122X, Q637X, Q2X, S4X, Q39X or Q1313X.

In another aspect of this embodiment, the PTC is G542X. In another aspect of this embodiment, the PTC is W1282X. In one aspect of this embodiment, the compound is administered in a therapeutically effective amount. Further, such methods may further comprise identifying a subject in need of such treatment, such as by identifying the presence of a PTC in the subject.

In another embodiment, the present disclosure provides methods for pharmacologically suppressing PTC associated with CF in a subject, wherein the PTC is present in the CFTR. In certain aspects of this embodiment, the PTC codon produces a non-functional polypeptide CTFR. Such method comprises the step of administering to the subject a compound of the present disclosure and further administering to the subject at least one of: i) an agent that increases the function of the CFTR polypeptide (for example, a CFTR potentiator); ii) an agent that increases the trafficking of the CFTR polypeptide (for example, a CFTR corrector); iii) an agent that inhibits NMD (for example, an NMD inhibitor); iv) an agent that that increases mRNA levels of the target mRNA (for example, a histone deacetylase inhibitor); v) an agent that increase general pulmonary function; or vi) a combination of the foregoing (each of the foregoing being considered a secondary agent). In this method, the administration of the compound stimulates read-through of the PTC and/or increases the stability of the mRNA transcript, thereby increasing the levels of CFTR polypeptide in the subject, while the administration of the agent that increases the function of the CFTR polypeptide improves the function of the CFTR produced by the read-through of the PTC, the agent that allows for improved trafficking of the CFTR polypeptide increases the levels of the CFTR polypeptide produced by the read-through of the PTC in functionally relevant locations (for example, the surface of the cell), and the agent that inhibits NMD and/or increases the levels of mRNA provide increased levels of mRNA for the action of the compounds of the present disclosure. In one aspect of this method, only an agent that increases the function of the CFTR polypeptide (for example, a CFTR potentiator) is administered with a compound of the present disclosure. In another aspect of this embodiment, only an agent that increases the trafficking of the CFTR polypeptide to the cell surface (for example, a CFTR corrector) is administered with a compound of the present disclosure. In another aspect of this embodiment, an agent that increases the function of the CFTR polypeptide and an agent that increases the trafficking of the CFTR polypeptide to the cell surface (for example, a CFTR potentiator and a CFTR corrector) is administered with a compound of the present disclosure. In another aspect of this embodiment, an agent that inhibits NMD (for example, a NMD inhibitor) is administered with a compound of the present disclosure. In another aspect of this embodiment, an agent that inhibits NMD and an agent that increases the trafficking of the CFTR polypeptide to the cell surface (for example, a CFTR corrector) is administered with a compound of the present disclosure. In another aspect of this embodiment, and an agent that increases the function of the CFTR polypeptide (for example, a CFTR potentiator) is administered with a compound of the present disclosure. In another aspect of this embodiment, an agent that increases the trafficking of the CFTR polypeptide to the cell surface (for example, a CFTR corrector) and an agent that increases the function of the CFTR polypeptide (for example, a CFTR potentiator) is administered with a compound of the present disclosure. In any of the foregoing embodiments, an agent that increases the levels of mRNA may be administered with a compound of the present disclosure. In any of the foregoing embodiments, an agent that increases general pulmonary function may be administered with a compound of the present disclosure.

In one aspect of this embodiment, the PTC is R553X, G542X, W1282X, R1162X, Y122X, Q637X, Q2X, S4X, Q39X or Q1313X. In another aspect of this embodiment, the PTC is G542X. In another aspect of this embodiment, the PTC is W1282X. In one aspect of this embodiment, the agent that increases the function of the CFTR polypeptide is VX-770, GP-5 or a combination of the foregoing. In one aspect of this embodiment, the agent that increases the trafficking of the CFTR polypeptide is VX-809, C1, C2, C1+C2, or a combination of the foregoing. In one aspect of this embodiment, the agent that inhibits NMD is NMDI-1, NMDI-9, NMDI-25, or NMDI-14. The administration of one or more agents may be prior to, contemporaneously with or after the administration of the compound of the present disclosure. In one aspect of this embodiment, the compound is administered in a therapeutically effective amount. Further, such methods may further comprise identifying a subject in need of such treatment, such as by identifying the presence of a PTC in the subject.

In another embodiment, the present disclosure provides methods for stabilizing an mRNA transcript containing a PTC, including by means of suppressing nonsense-mediated decay. Such method comprises the step of administering to the subject a compound of the present disclosure. In one aspect of this embodiment, the PTC is R553X, G542X, W1282X, R1162X, Y122X, Q637X, Q2X, S4X, Q39X or Q1313X. In another aspect of this embodiment, the PTC is G542X. In another aspect of this embodiment, the PTC is W1282X. In one aspect of this embodiment, the PTC is W402X, Q70X, R628X, Q148X, E404X, Y343X or Q548X. In another aspect of this embodiment, the PTC is W402X. In another aspect of this embodiment, the PTC is Q70X. In another aspect of this embodiment, the PTC is Q70X. In one aspect of this embodiment, the PTC is associated with a disease or condition selected from the group consisting of: cystic fibrosis, Duchenne muscular dystrophy, Becker muscular dystrophy, spinal muscular atrophy, Hurler syndrome, Hemophilia, Hemophilia B, Usher syndrome and cancer. In one aspect of this embodiment, the compound is administered in a therapeutically effective amount. Further, such methods may further comprise identifying a subject in need of such treatment, such as by identifying the presence of a PTC in the subject.

In another embodiment, the present disclosure provides methods for increasing the levels of an mRNA transcript containing a PTC codon, including by means of suppressing nonsense-mediated decay. Such method comprises the step of administering to the subject a compound of the present disclosure. In one aspect of this embodiment, the PTC is R553X, G542X, W1282X, R1162X, Y122X, Q637X, Q2X, S4X, Q39X or Q1313X. In another aspect of this embodiment, the PTC is G542X. In another aspect of this embodiment, the PTC is W1282X. In one aspect of this embodiment, the PTC is W402X, Q70X, R628X, Q148X, E404X, Y343X or Q548X. In another aspect of this embodiment, the PTC is W402X. In another aspect of this embodiment, the PTC is Q70X. In one aspect of this embodiment, the PTC is associated with a disease or condition selected from the group consisting of: cystic fibrosis, Duchenne muscular dystrophy, Becker muscular dystrophy, spinal muscular atrophy, Hurler syndrome, Hemophilia, Hemophilia B, Usher syndrome and cancer. In one aspect of this embodiment, the compound is administered in a therapeutically effective amount. Further, such methods may further comprise identifying a subject in need of such treatment, such as by identifying the presence of a PTC in the subject.

In a preferred embodiment, the methods above may further comprise the administration of a secondary agent that may be administered prior to or contemporaneously with a compound of the present disclosure. In certain embodiments, the secondary agent is: i) an agent that increases the function of the CFTR polypeptide (for example, a CFTR potentiator); ii) an agent that increases the trafficking of the CFTR polypeptide (for example, a CFTR corrector); iii) an agent that inhibits NMD (for example, an NMD inhibitor); iv) an agent that that increases mRNA levels of the target mRNA (for example, a histone deacetylase inhibitor); v) an agent that increase general pulmonary function; or vi) a combination of the foregoing (each of the foregoing being considered a secondary agent). In certain embodiments, the secondary agent is a CFTR potentiator, a CFTR corrector, an NMD inhibitor, an agent that increases mRNA levels or a combination of any of the foregoing. In certain embodiments, the CFTR potentiator is VX-770, GP-5 or a combination of the foregoing. In certain embodiments, the CFTR corrector is VX-809, C1, C2 or a combination of the foregoing. In certain embodiments, the NMD inhibitor is NMDI-1, NMDI-9, NMDI-25, NMDI-14 or a combination of the foregoing. In certain embodiments, the agent that increases the levels of mRNA is a histone deacetylase inhibitor. In certain embodiments, the agent that increase general pulmonary function is a flavone, an isoflavone, boswellic acid, forskolin, EGCG, bioperine, quercetin, amentoflavone, trans-resveratrol, turmeric or a combination of the foregoing.

In the foregoing methods, representative examples of therapeutically useful compounds include, but are not limited to, escin, a purified or partially purified isomer of escin, a compound of the formula I, a compound of the formula IIa, a compound of the formula IIb, escin 1a, escin 1b, isoescin 1a, isoescin 1b, colchicine, cyclohexamide, doxorubicin, pyranoradine tetraphosphate (PT), prednicarbate, oxibendazole, albendazole, mebendazole and potassium p-aminobenzoate (PABA). In certain preferred embodiments, the compound is a compound of the formula Ia. In certain preferred embodiments, the compound is a compound of the formula Ib. In certain preferred embodiments, the compound is a compound of the formula IIa. In certain preferred embodiments, the compound is a compound of the formula III) wherein $R_4$ is H. In certain preferred embodiments, the compound is escin 1a. In certain preferred embodiments, the compound is escin 1b. In certain preferred embodiments, the compound is isoescin 1a. In certain preferred embodiments, the compound is isoescin 1b. In certain preferred embodiments, the compound is potassium para-aminobenzoate (PABA).

Administration of the compounds of the present disclosure may be accomplished as is known in the art as the compounds disclosed are all known to be therapeutically useful for other conditions in the human. This includes oral dosing regiments to provide the most effective concentrations in human plasma. This also includes dosing regimens with subcutaneous or intravenous routes of administration to achieve adequate levels.

Compounds for Use with the Present Disclosure

As discussed above, the present disclosure provides for methods for increasing read-through of a PTC codon, methods for stabilizing an mRNA transcript that contains a PTC codon and methods for increasing the levels of an mRNA that contains a PTC codon by administering a compound of the present disclosure.

A variety of compounds are disclosed herein which may be used in the disclosed methods. Certain compounds described herein or contained in compositions of the present disclosure may exist in particular geometric or stereoisomeric forms. In addition, compounds of the present disclosure may also be optically active. The present disclosure contemplates all such compounds, including cis- and trans-isomers, (R)- and (S)-enantiomers, diastereoisomers, (D)-isomers, (L)-isomers, the racemic mixtures thereof, and other mixtures thereof, as falling within the scope of the disclosure. Additional asymmetric carbon atoms may be present in a substituent such as an alkyl group. All such isomers, as well as mixtures thereof, are intended to be included in this disclosure. In certain cases, specific geometric or stereoisomeric forms may be specified.

In one embodiment, the compound is escin (also known as aescin). Escin is a mixture of saponins found in *Aesculus hippocastanum* (the horse chestnut). Escin is the main active compound in horse chestnut, and is responsible for most of its medicinal properties. Extracts from the seeds of *Aesculus hippocastanum* have been traditionally used in China as as stomachic and analgesic agent, an anti-fever and anti-hemorrhoidal agent (Matsuda et al., 1997). The saponin mixture isolated from the seeds is a pentacyclic triterpene and is referred to as escin which exists in alpha and beta form. It is the beta form of escin that has been described to exhibit ant inflammatory (Matsuda et al., 1997; Rothkopf and Vogel, 1976), anti-edema, capillary protective, hypoglycemic (Kimura et al., 2006), antiobesity (Hu et al., 2008) and ethanol absorption inhibitory (Sirtori, 2001; Yoshikawa et al., 1996) activities. Escin was found to inhibit acute inflammation induced by acetic acid in mice and histamine in rats (Matsuda et al., 1998), suppress traumatic brain injury in rats (Xiao and Wei, 2005), attenuate postoperative adhesions (Fu et al., 2005), accelerate gastrointestinal transit (Matsuda et al., 1999), inhibit brain ischemia injury induced apoptosis in rats (Hu et al., 2004), abrogate ovariectomized induced osteopenia in rats (Pytlik et al., 2000; Pytlik et al., 1999), manifest hypoglycemic activity (Yoshikawa et al., 1996) and exhibit anti-ulcerogenic effects (Marhuenda et al., 1994). This triterpene was also found to inhibit chronic aberrant foci formation in rats, and induce apoptosis in human colon cancer HT29 cells (Patlolla et al., 2006). Escin is in clinical trial in patients with HIV-1 (Grases et al., 2004) for treatment of blunt impact injuries (Wetzel et al., 2002), and for cutaneous pruritus (Li et al., 2004). In addition, this triterpene was found to suppress the expression of adhesion molecules on endothelial cells (Hu et al., 2004; Montopoli et al., 2007), prevent hypoxia-induced adhesiveness of neutrophils to endothelial cells (Arnould et al., 1996), and inhibit HIV-1 protease (Yang et al., 1999). Clinical evidence suggests aescin is a safe and effective treatment for chronic venous insufficiency (Sirtori C R, Pharmacol. Res. 44 (3): 183-193, September 2001; Pittler M H, et al.; Cochrane Database Syst Rev (1): CD003230, 2006; Diehm C., et al.; Lancet 347 (8997): 292-294, February 1996).

In one embodiment, the compound is escin. When escin is specified without any further characterization, it refers to escin purified from *Aesculus hippocastanum* (such as from the seeds) and is understood to include a mixture of pentacyclic triterpenes and includes both alpha and beta forms and includes escin 1a, escin 1b, isoescin 1a and isoescin 1b. In one aspect of this embodiment, escin comprises a mixture of compounds of the general formula Ia or a pharmaceutically acceptable salt, hydrate or solvate thereof:

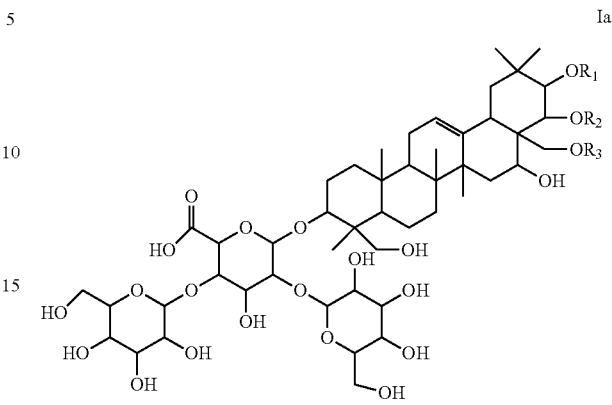

Ia wherein:
$R_1$ is selected from the group consisting of: angeloyl and tigoyl;
$R_2$ is selected from the group consisting of: acetyl (—C(O)CH$_3$) and —H; and
$R_3$ is selected from the group consisting of: acetyl (—C(O)CH$_3$) and —H.

In one aspect of this embodiment, the mixture of compounds includes at least one of the following compounds:
i) The compound of formula Ia, wherein $R_1$ is tigoyl, $R_2$ is acetyl and $R_3$ is —H (escin 1a);
ii) The compound of formula Ia, wherein $R_1$ is angeloyl, $R_2$ is acetyl and $R_3$ is —H (escin 1b);
iii) The compound of formula Ia, wherein $R_1$ is tigoyl, $R_2$ is —H and $R_3$ is acetyl (isoescin 1a); and
iv) The compound of formula Ia, wherein $R_1$ is angeloyl, $R_2$ is —H and $R_3$ is acetyl (isoescin 1b).

In certain embodiments, the mixture contains all 4 compounds i) to iv). In certain embodiments, the mixture contains compound i) and optionally one or more of compounds ii) to iv). In certain embodiments, the mixture contains compound ii) and optionally one or more of compounds i) or iii) to iv).

In another aspect of this embodiment, escin comprises a mixture of compounds of the general formula Ib, or a pharmaceutically acceptable salt, hydrate or solvate thereof, wherein $R_1$, $R_2$ and $R_3$ are as defined for the compound of general formula Ia.

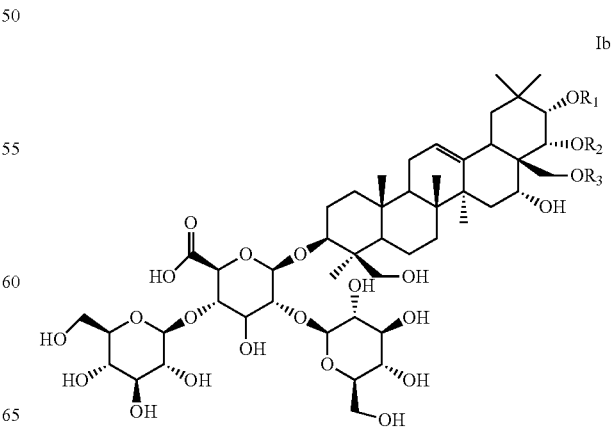

Ib

In one aspect of this embodiment, the mixture of compounds includes at least one of the following compounds:

v) The compound of formula Ib, wherein $R_1$ is tigoyl, $R_2$ is acetyl and $R_3$ is —H (escin 1a);

vi) The compound of formula Ib, wherein $R_1$ is angeloyl, $R_2$ is acetyl and $R_3$ is —H (escin 1b);

vii) The compound of formula Ib, wherein $R_1$ is tigoyl, $R_2$ is —H and $R_3$ is acetyl (isoescin 1a); and viii) The compound of formula Ib, wherein $R_1$ is angeloyl, $R_2$ is —H and $R_3$ is acetyl (isoescin 1b).

In certain embodiments, the mixture contains all 4 compounds v) to viii). In certain embodiments, the mixture contains compound v) and optionally one or more of compounds vi) to viii). In certain embodiments, the mixture contains compound vi) and optionally one or more of compounds v) and vii) to viii). In certain embodiments, the mixture contains compound vii) and optionally one or more of compounds v), vi) and viii). In certain embodiments, the mixture contains compound viii) and optionally one or more of compounds v) to vii).

In another embodiment, the compound is a purified isomer of escin. Suitable isomers include, but are not limited to:

escin 1a, wherein $R_1$ is tigoyl, $R_2$ is acetyl and $R_3$ is —H in formula Ia or Ib;

escin 1b, wherein $R_1$ is angeloyl, $R_2$ is acetyl and $R_3$ is —H in formula Ia or Ib;

isoescin 1a, wherein $R_1$ is tigoyl, $R_2$ is —H and $R_3$ is acetyl in formula Ia or Ib;

isoescin 1b, wherein $R_1$ is angeloyl, $R_2$ is —H and $R_3$ is acetyl in formula Ia or Ib; and mixtures of the foregoing.

In certain embodiments, the mixture contains all 4 compounds. In certain embodiments, the mixture contains escin 1a and optionally one or more of escin 1b, isoescin 1a and isoescin 1b. In certain embodiments, the mixture contains escin 1b and optionally one or more of escin 1a, isoescin 1a and isoescin 1b. In certain embodiments, the mixture contains isoescin 1a and optionally one or more of escin 1a, escin 1b and isoescin 1b. In certain embodiments, the mixture contains isoescin 1b and optionally one or more of escin 1a, escin 1b and isoescin 1a. In certain embodiments, the mixture contains escin 1a and escin 1b and optionally one or more of isoescin 1a and isoescin 1b.

In a particular embodiment, the isomer of escin is escin 1a. In another particular embodiment, the isomer of escin is isoescin 1a. In a particular embodiment, the isomer of escin is escin 1b. In another particular embodiment, the isomer of escin is isoescin 1b.

The term "purified" when used in relation to an isomer of escin, means that the specified isomer is present at equal to or greater than 85 wt % (such as 90 wt %, 95 wt %, 98 wt % or 99 wt %) with respect to the total weight of the compounds present. The term "partially purified" when used in relation to an isomer of escin, means that the specified isomer is present at equal to or greater than 50 wt % (such as 60 wt %, 70 wt %, 80 wt % or 90 wt %) with respect to the total weight of the compounds present.

In another embodiment, the compound has the structure of formula IIa or IIb or a pharmaceutically acceptable salt, hydrate or solvate thereof

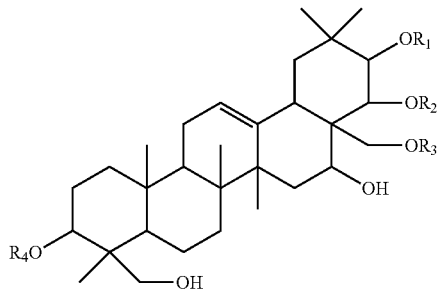

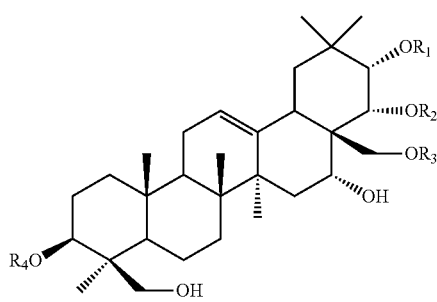

wherein:

$R_1$, $R_2$ and $R_3$ are each independently selected from the group consisting of: —H, alkyl, alkenyl, alkanoyl and alkenoyl; and $R_4$ is selected from the group consisting of: a linear saccharide chain of 1-11 saccharide units, a branched saccharide chain of 1-11 saccharide units and —H.

In one aspect of this embodiment, the alkyl group has an alkyl portion from 1 to 10 carbons in length and the alkyl portion is substituted or unsubstituted. In another aspect of this embodiment, the alkyl group has an alkyl portion from 1 to 10 carbons in length and the alkyl portion is unsubstituted. In another aspect of this embodiment, the alkyl group has an alkyl portion from 1 to 5 carbons in length and the alkyl portion is unsubstituted.

In one aspect of this embodiment, the alkenyl group has an alkyl portion from 1 to 10 carbons in length and the alkenyl portion is substituted or unsubstituted. In another aspect of this embodiment, the alkenyl group has an alkyl portion from 1 to 10 carbons in length and the alkenyl portion is unsubstituted. In another aspect of this embodiment, the alkenyl group has an alkyl portion from 1 to 5 carbons in length and the alkenyl portion is unsubstituted.

In one aspect of this embodiment, the alkanoyl group has an alkyl portion from 1 to 10 carbons in length and the alkyl portion is substituted or unsubstituted. In another aspect of this embodiment, the alkanoyl group has an alkyl portion from 1 to 10 carbons in length and the alkyl portion is unsubstituted. In another aspect of this embodiment, the alkanoyl group has an alkyl portion from 1 to 5 carbons in length and the alkyl portion is unsubstituted. Representative alkanoyl groups include, but are not limited to, acetyl, hexanoyl, benzoyl, ethylbutyryl, ethanoyl, propionyl, isobutyryl and butyryl.

In one aspect of this embodiment, the alkenoyl group has an alkenyl portion from 1 to 10 carbons in length and the alkenyl portion is substituted or unsubstituted. In another aspect of this embodiment, the alkenoyl group has an alkenyl portion from 1 to 10 carbons in length and the alkenyl portion is unsubstituted. In another aspect of this embodiment, the alkenoyl group has an alkenyl portion from 1 to 5 carbons in length and the alkenyl portion is unsubstituted. Representative alkenoyl groups include, but are not limited to, angeloyl, tigoyl, senecioyl, crotonoyl, 3,3-Dimethylartyloyl, cinnamoyl, pentenoyl, 2-propenoyl, (2E)-2-pentenoyl and 4-pentenoyl.

In another aspect of this embodiment:
$R_1$ is selected from the group consisting of: —H, alkyl, alkenyl, acetyl, hexanoyl, benzoyl, ethylbutyryl, ethanoyl, propionyl, isobutyryl, butyryl, angeloyl, tigoyl, senecioyl, crotonoyl, 3,3-dimethylartyloyl, cinnamoyl, pentenoyl, 2-propenoyl, (2E)-2-pentenoyl and 4-pentenoyl;
$R_2$ is acetyl;
$R_3$ is —H; and
$R_4$ is selected from the group consisting of: a linear saccharide chain of 1-11 saccharide units, a branched saccharide chain of 1-11 saccharide units and —H.

In another aspect of this embodiment:
$R_1$ is selected from the group consisting of: —H, angeloyl, tigoyl, senecioyl, crotonoyl, 3,3-dimethylartyloyl, cinnamoyl, pentenoyl, 2-propenoyl, (2E)-2-pentenoyl and 4-pentenoyl;
$R_2$ is acetyl;
$R_3$ is —H; and
$R_4$ is selected from the group consisting of: a linear saccharide chain of 1-11 saccharide units, a branched saccharide chain of 1-11 saccharide units and —H.

In another aspect of this embodiment:
$R_1$ is selected from the group consisting of: angeloyl and tigoyl;
$R_2$ is acetyl;
$R_3$ is —H; and
$R_4$ is selected from the group consisting of: a linear saccharide chain of 1-11 saccharide units, a branched saccharide chain of 1-11 saccharide units and —H.

In another aspect of this embodiment:
$R_1$ is selected from the group consisting of: —H, alkyl, alkenyl, acetyl, hexanoyl, benzoyl, ethylbutyryl, ethanoyl, propionyl, isobutyryl, butyryl, angeloyl, tigoyl, senecioyl, crotonoyl, 3,3-dimethylartyloyl, cinnamoyl, pentenoyl, 2-propenoyl, (2E)-2-pentenoyl and 4-pentenoyl;
$R_2$ is —H;
$R_3$ is acetyl; and
$R_4$ is selected from the group consisting of: a linear saccharide chain of 1-11 saccharide units, a branched saccharide chain of 1-11 saccharide units and —H.

In another aspect of this embodiment:
$R_1$ is selected from the group consisting of: —H, angeloyl, tigoyl, senecioyl, crotonoyl, 3,3-dimethylartyloyl, cinnamoyl, pentenoyl, 2-propenoyl, (2E)-2-pentenoyl and 4-pentenoyl;
$R_2$ is —H;
$R_3$ is acetyl; and
$R_4$ is selected from the group consisting of: a linear saccharide chain of 1-11 saccharide units, a branched saccharide chain of 1-11 saccharide units and —H.

In another aspect of this embodiment:
$R_1$ is selected from the group consisting of: angeloyl and tigoyl;
$R_2$ is —H;
$R_3$ is acetyl; and
$R_4$ is selected from the group consisting of: a linear saccharide chain of 1-11 saccharide units, a branched saccharide chain of 1-11 saccharide units and —H.

In one aspect of the foregoing embodiments, $R_4$ is a linear saccharide chain of 1 to 5 saccharide units. In another aspect of this embodiment, $R_4$ is a linear saccharide chain of 3 saccharide units.

In one aspect of the foregoing embodiments, $R_4$ is a branched saccharide chain of 1 to 5 saccharide units. In another aspect of the foregoing embodiments, $R_4$ is a branched saccharide chain of 3 saccharide units. In still another aspect of the foregoing embodiments, $R_4$ is a branched saccharide chain of the structure Ma for a compound of the formula IIa or IIIb for a compound of the formula IIb:

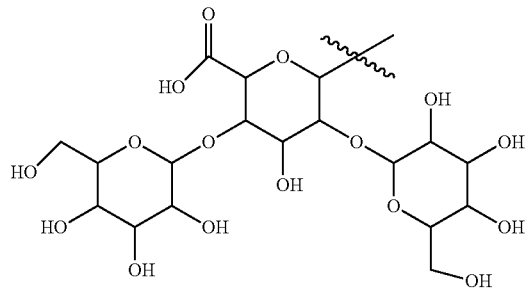 [SMILES: *C1OC(C(=O)O)C(OC2OC(CO)C(O)C(O)C2O)C(O)C1OC1OC(CO)C(O)C(O)C1O]

IIIa

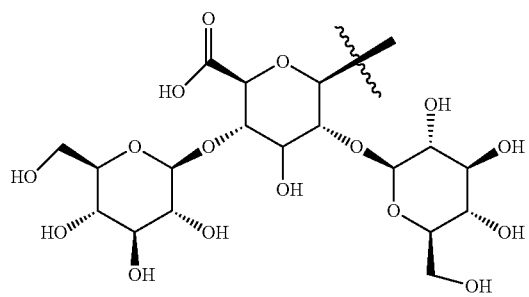

IIIb

In one aspect of this embodiment, $R_4$ is —H and the compound may be considered a sapogenin.

In a first preferred aspect of this embodiment, the compound has the general formula IIa, wherein $R_1$ is angeloyl, $R_2$ is acetyl, $R_3$ is —H and $R_4$ is —H.

In a second preferred aspect of this embodiment, the compound has the general formula IIa, wherein $R_1$ is tigolyl, $R_2$ is acetyl, $R_3$ is —H and $R_4$ is —H.

In a third preferred aspect of this embodiment, the compound has the general formula IIa, wherein $R_1$ is angeloyl, $R_2$ is —H, $R_3$ is acetyl and $R_4$ is —H.

In a fourth preferred aspect of this embodiment, the compound has the general formula IIa, wherein $R_1$ is tigoyl, $R_2$ is —H, $R_3$ is acetyl and $R_4$ is —H.

In a fifth preferred aspect of this embodiment, the compound has the general formula IIa, wherein $R_1$ is angeloyl, $R_2$ is acetyl, $R_3$ is —H and $R_4$ is a branched saccharide chain of 1-5 saccharide units.

In a sixth preferred aspect of this embodiment, the compound has the general formula IIa, wherein $R_1$ is tigoyl, $R_2$ is acetyl, $R_3$ is —H and $R_4$ is a branched saccharide chain of 1-5 saccharide units.

In a seventh preferred aspect of this embodiment, the compound has the general formula IIa, wherein $R_1$ is angeloyl, $R_2$ is —H, $R_3$ is acetyl and $R_4$ is a branched saccharide chain of 1-5 saccharide units.

In an eighth preferred aspect of this embodiment, the compound has the general formula IIa, wherein $R_1$ is tigoyl, $R_2$ is —H, $R_3$ is acetyl and $R_4$ is a branched saccharide chain of 1-5 saccharide units.

In a ninth preferred aspect of this embodiment, the compound has the general formula IIb, wherein $R_1$ is angeloyl, $R_2$ is acetyl, $R_3$ is —H and $R_4$ is —H.

In a tenth preferred aspect of this embodiment, the compound has the general formula IIb, wherein $R_1$ is tigolyl, $R_2$ is acetyl, $R_3$ is —H and $R_4$ is —H.

In an eleventh preferred aspect of this embodiment, the compound has the general formula IIb, wherein $R_1$ is angeloyl, $R_2$ is —H, $R_3$ is acetyl and $R_4$ is —H.

In a twelfth preferred aspect of this embodiment, the compound has the general formula IIb, wherein $R_1$ is tigoyl, $R_2$ is —H, $R_3$ is acetyl and $R_4$ is —H.

In a thirteenth preferred aspect of this embodiment, the compound has the general formula IIb, wherein $R_1$ is angeloyl, $R_2$ is acetyl, $R_3$ is —H and $R_4$ is a branched saccharide chain of 1-5 saccharide units.

In a fourteenth preferred aspect of this embodiment, the compound has the general formula IIb, wherein $R_1$ is tigoyl, $R_2$ is acetyl, $R_3$ is —H and $R_4$ is a branched saccharide chain of 1-5 saccharide units.

In a fifteenth preferred aspect of this embodiment, the compound has the general formula IIb, wherein $R_1$ is angeloyl, $R_2$ is —H, $R_3$ is acetyl and $R_4$ is a branched saccharide chain of 1-5 saccharide units.

In a sixteenth preferred aspect of this embodiment, the compound has the general formula IIb, wherein $R_1$ is tigoyl, $R_2$ is —H, $R_3$ is acetyl and $R_4$ is a branched saccharide chain of 1-5 saccharide units.

In another embodiment, the compound is albendazole or a pharmaceutically acceptable salt, hydrate or solvate thereof.

In another embodiment, the compound is colchicine or a pharmaceutically acceptable salt, hydrate or solvate thereof.

In another embodiment, the compound is cyclohexamide or a pharmaceutically acceptable salt, hydrate or solvate thereof.

In another embodiment, the compound is oxibendazole or a pharmaceutically acceptable salt, hydrate or solvate thereof.

In another embodiment, the compound is mebendazole or a pharmaceutically acceptable salt, hydrate or solvate thereof.

In another embodiment, the compound is pyronaridine tetraphosphate or a pharmaceutically acceptable salt, hydrate or solvate thereof.

In another embodiment, the compound is prednicarbate or a pharmaceutically acceptable salt, hydrate or solvate thereof.

In another embodiment, the compound is potassium para-aminobenzoate (PABA) or a pharmaceutically acceptable salt, hydrate or solvate thereof.

In another embodiment, the compound is doxorubicin or a pharmaceutically acceptable salt, hydrate or solvate thereof.

Composition of Matter, Combination and Formulation

The present disclosure also provides for compositions of matter, combinations and formulations comprising, consisting essentially of or consisting of a mixture of purified or partially purified escin isomers. Such compositions of matter, combinations and formulations provide an advantage over the compounds of the art in that specific isomers of escin are combined in a purified or partially purified form, whereas the composition of matter, combinations and formulations of the prior art contained unfractionated extracts from a plant source.

In one aspect of this embodiment, the composition of matter, combination or formulation comprises, consists essentially of or consists of a mixture of compounds of the general formula IIa or 1b, or a pharmaceutically acceptable salt, hydrate or solvate thereof, wherein $R_1$, $R_2$ and $R_3$ are as defined for the compound of general formula Ia.

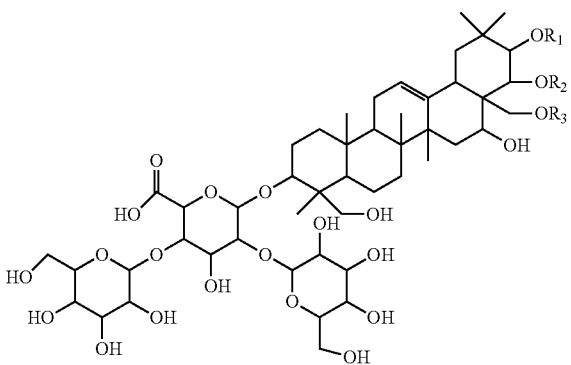

Ia

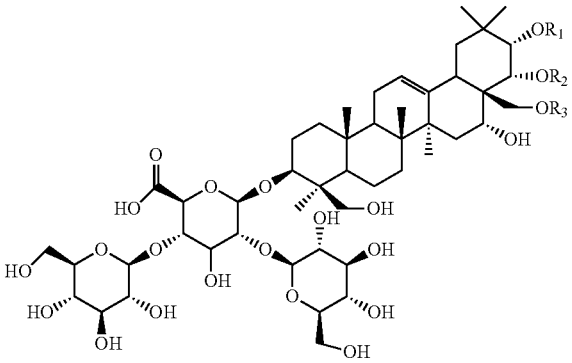

Ib

In one aspect of this embodiment, the composition of matter, combination or formulation comprises, consists essentially of or consists of escin 1a, escin 1b, isoescin 1a and isoescin 1b. In another aspect of this embodiment, the composition of matter, combination or formulation comprises, consists essentially of or consists of escin 1a and optionally one or more of escin 1b, isoescin 1a and isoescin 1b. In another aspect of this embodiment, the composition of matter, combination or formulation comprises, consists essentially of or consists of escin 1b and optionally one or more of escin 1a, isoescin 1a and isoescin 1b. In another aspect of this embodiment, the composition of matter, combination or formulation comprises, consists essentially of or consists of isoescin 1a and optionally one or more of escin 1a, escin 1b and isoescin 1b. In another aspect of this embodiment, the composition of matter, combination or formulation comprises, consists essentially of or consists of isoescin 1b and optionally one or more of escin 1a, escin 1b and isoescin 1a. In certain embodiments, the mixture contains escin 1a and escin 1b and optionally one or more of isoescin 1a and isoescin 1b.

The term "purified" when used in relation to an isomer of escin in a composition of matter, combination or formulation, means that the specified isomer is present at equal to or greater than 85 wt % (such as 90 wt %, 95 wt %, 98 wt % or 99 wt %) with respect to the total weight of the compounds present. The term "partially purified" when used in relation to an isomer of escin in a composition of matter, combination or formulation, means that the specified isomer is present at equal to or greater than 50 wt % (such as 60 wt %, 70 wt %, 80 wt % or 90 wt %) with respect to the total weight of the compounds present.

Such composition of matter, combination or formulation may optionally include one or more of the secondary agents disclosed herein. Such composition of matter, combination or formulation may optionally be administered in conjunction with one or more of the secondary agents disclosed herein. Such administration of a secondary agent may be either concurrently, before or after the administration of the composition of matter, combination or formulation.

Pharmaceutical Compositions

The compounds of the disclosure may be formulated into pharmaceutical compositions for administration to subjects in a biologically compatible form suitable for administration in vivo. The present disclosure provides a pharmaceutical composition comprising compounds of the disclosure in admixture with a pharmaceutically acceptable excipient. The pharmaceutically-acceptable excipient must be acceptable in the sense of being compatible with the other ingredients of the composition and not deleterious to the recipient thereof. The pharmaceutically-acceptable excipients employed herein may be selected from various organic or inorganic materials that are used as materials for pharmaceutical formulations and which are incorporated as analgesic agents, buffers, binders, disintegrants, diluents, emulsifiers, excipients, extenders, glidants, solubilizers, stabilizers, suspending agents, tonicity agents, vehicles and viscosity-increasing agents. Pharmaceutical additives, such as antioxidants, aromatics, colorants, flavor-improving agents, preservatives, and sweeteners, may also be added. Examples of acceptable pharmaceutical excipients include carboxymethyl cellulose, crystalline cellulose, glycerin, gum arabic, lactose, magnesium stearate, methyl cellulose, powders, saline, sodium alginate, sucrose, starch, talc and water, among others. In some embodiments, the term "pharmaceutically acceptable" means approved by a regulatory agency of the Federal or a state government or listed in the U.S. Pharmacopeia or other generally recognized pharmacopeia for use in animals, and more particularly in humans.

Often, the pharmaceutically acceptable excipient is chemically inert toward the active compounds and is non-toxic under the conditions of use. Examples of pharmaceutically acceptable excipients may include, for example, water or saline solution, polymers such as polyethylene glycol, carbohydrates and derivatives thereof, oils, fatty acids, or alcohols. In some embodiments, the excipient is saline or water. In some embodiments, the excipient is saline. In some embodiments, the excipient is water. Pharmaceutically acceptable excipients are also well-known to those who are skilled in the art. The choice of excipient will be determined in part by the particular compound(s), as well as by the particular method used to administer the composition. Accordingly, there is a wide variety of suitable formulations of the pharmaceutical composition of the present invention. The following methods and excipients are merely exemplary and are in no way limiting.

Surfactants such as, but not limited to, detergents, are also suitable for use in the formulations. Specific examples of surfactants include polyvinylpyrrolidone, polyvinyl alcohols, copolymers of vinyl acetate and of vinylpyrrolidone, polyethylene glycols, benzyl alcohol, mannitol, glycerol, sorbitol or polyoxyethylenated esters of sorbitan; lecithin or sodium carboxymethylcellulose; or acrylic derivatives, such as methacrylates and others, anionic surfactants, such as alkaline stearates, in particular sodium, potassium or ammonium stearate; calcium stearate or triethanolamine stearate; alkyl sulfates, in particular sodium lauryl sufate and sodium cetyl sulfate; sodium dodecylbenzenesulphonate or sodium dioctyl sulphosuccinate; or fatty acids, in particular those derived from coconut oil, cationic surfactants, such as water-soluble quaternary ammonium salts of formula $N^+R'R''R'''R''''Y^-$, in which the R radicals are identical or different optionally hydroxylated hydrocarbon radicals and Y is an anion of a strong acid, such as halide, sulfate and sulfonate anions; cetyltrimethylammonium bromide is one of the cationic surfactants which can be used, amine salts of formula $N^+R'R''R'''$, in which the R radicals are identical or different optionally hydroxylated hydrocarbon radicals; octadecylamine hydrochloride is one of the cationic surfactants which can be used, non-ionic surfactants, such as optionally polyoxyethylenated esters of sorbitan, in particular Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide, amphoteric surfactants, such as substituted lauryl compounds of betaine, When administered to a subject, the compounds of the disclosure and pharmaceutically acceptable excipients may be sterile. In some embodiments, an aqueous solution is an excipient when the compound of the disclosure is administered intravenously. In some embodiments, the excipient is a saline solution when a compound of the disclosure is administered intravenously. Aqueous dextrose and glycerol solutions may also be employed as liquid excipients, particularly for injectable solutions. Suitable pharmaceutical excipients may also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, polyethylene glycol 300, water, ethanol, polysorbate 20, and the like. The present compositions, if desired, may also contain minor amounts of wetting or emulsifying agents, or pH buffering agents.

The pharmaceutical formulations of the present disclosure are prepared by methods well-known in the pharmaceutical arts. For example, the compounds of the disclosure are brought into association with an excipient, as a suspension or solution. Optionally, one or more accessory ingredients (e.g., buffers, flavoring agents, surface active agents, and the like) also are added. The choice of excipient is determined by the solubility and chemical nature of the compounds, chosen route of administration and standard pharmaceutical practice. In some embodiments, the formulation comprises a compound of the disclosure and water. In some embodiments, the formulation comprises a compound of the disclosure and saline.

Additionally, the compounds of the disclosure are administered to a subject, such as a human or animal subject, by known procedures including, without limitation, oral administration, sublingual or buccal administration, parenteral administration, subcutaneous administration, transdermal administration, via inhalation or intranasally, vaginally, rectally, and intramuscularly. The compounds of the disclosure may be administered parenterally, by epifascial, intracapsular, intracranial, intracutaneous, intrathecal, intramuscular, intraorbital, intraperitoneal, intraspinal, intrasternal, intravascular, intravenous, parenchymatous, subcutaneous or sublingual injection, or by way of catheter. In some embodiments, the compounds of the disclosure are administered to the subject by way of intramuscular delivery. In some embodiments, the compounds of the disclosure are administered to the subject by way of intraperitoneal delivery. In some embodiments, the compounds of the disclosure are administered to the subject by way of intravenous delivery. In some embodiments, the compounds of the disclosure are administered orally. In certain embodiments, the compounds of the disclosure are administered by bolus administration, for example an IV or IM bolus administration.

For oral administration, a formulation of the compound of the disclosure may be presented as capsules, tablets, powders, granules, or as a suspension or solution. Capsule formulations may be gelatin, soft-gel or solid. Tablets and capsule formulations may further contain one or more adjuvants, binders, diluents, disintegrants, excipients, fillers, or lubricants, each of which are known in the art. Examples of such include carbohydrates such as lactose or sucrose, dibasic calcium phosphate anhydrous, corn starch, mannitol, xylitol, cellulose or derivatives thereof, microcrystalline cellulose, gelatin, stearates, silicon dioxide, talc, sodium starch glycolate, acacia, flavoring agents, preservatives, buffering agents, disintegrants, and colorants. Orally administered compositions may contain one or more optional agents such as, but not limited to, sweetening agents such as fructose, aspartame or saccharin; flavoring agents such as peppermint, oil of wintergreen, or cherry; coloring agents; and preservative agents, to provide a pharmaceutically palatable preparation.

For parenteral administration (i.e., administration by injection through a route other than the alimentary canal), the compounds of the disclosure may be combined with a sterile aqueous solution that is isotonic with the blood of the subject. Such a foimulation is prepared by dissolving a solid active ingredient in water containing physiologically-compatible substances, such as sodium chloride, glycine and the like, and having a buffered pH compatible with physiological conditions, so as to produce an aqueous solution, then rendering said solution sterile. The formulation may be presented in unit or multi-dose containers, such as sealed ampules or vials. The formulation may be delivered by any mode of injection, including, without limitation, epifascial, intracapsular, intracranial, intracutaneous, intrathecal, intramuscular, intraorbital, intraperitoneal, intraspinal, intrasternal, intravascular, intravenous, parenchymatous, subcutaneous, or sublingual or by way of catheter into the subjects body.

Parenteral administration includes aqueous and non-aqueous based solutions. Examples of which include, for example, water, saline, aqueous sugar or sugar alcohol solutions, alcoholic (such as ethyl alcohol, isopropanol, glycols), ethers, oils, glycerides, fatty acids, and fatty acid esters. In some embodiments, water is used for parenteral administration. In some embodiments, saline is used for parenteral administration. Oils for parenteral injection include animal, vegetable, synthetic or petroleum based oils. Examples of sugars for solution include sucrose, lactose, dextrose, mannose, and the like. Examples of oils include mineral oil, petrolatum, soybean, corn, cottonseed, peanut, and the like. Examples of fatty acids and esters include oleic acid, myristic acid, stearic acid, isostearic acid, and esters thereof.

For transdermal administration, the compounds of the disclosure are combined with skin penetration enhancers, such as propylene glycol, polyethylene glycol, isopropanol, ethanol, oleic acid, N-methylpyrrolidone and the like, which increase the permeability of the skin to the compounds of the disclosure and permit the compounds to penetrate through the skin and into the bloodstream. The compound/enhancer compositions also may be further combined with a polymeric substance, such as ethylcellulose, hydroxypropyl cellulose, ethylene/vinylacetate, polyvinyl pyrrolidone, and the like, to provide the composition in gel form, which are dissolved in a solvent, such as methylene chloride, evaporated to the desired viscosity and then applied to backing material to provide a patch.

In some embodiments, the compounds of the disclosure are in unit dose form such as a tablet, capsule or single-dose vial. Suitable unit doses, i.e., an effective amount, may be determined during clinical trials designed appropriately for each of the conditions for which administration of a chosen compound is indicated and will, of course, vary depending on the desired clinical endpoint.

The present disclosure also provides articles of manufacture for treating and preventing disorders described herein in a subject. The articles of manufacture comprise a compound of the disclosure or a pharmaceutical composition comprising a compound of the disclosure, optionally further containing a secondary agent, as described herein. The articles of manufacture may be packaged with indications for various disorders that the compound of the disclosure or the pharmaceutical compositions comprising a compound of the disclosure are capable of treating and/or preventing. For example, the articles of manufacture may comprise a unit dose of a compound of the disclosure or a pharmaceutical compositions comprising a compound of the disclosure that is capable of treating or preventing a certain disorder, and an indication that the unit dose is capable of treating or preventing a certain disorder, for example cystic fibrosis.

Dosage and Administration

In accordance with the methods of the present disclosure, the compounds of the disclosure are administered to the subject (or are contacted with cells of the subject) in a therapeutically effective amount. This amount is readily determined by the skilled artisan, based upon known procedures, including analysis of titration curves established in vivo and methods and assays disclosed herein. In some embodiments, a therapeutically effective amount increases read-through of a PTC codon in the subject. In some embodiments, a therapeutically effective amount increases the stability of an mRNA containing a PTC in a subject.

In one embodiment, the compounds of the present disclosure are administered in a therapeutically effective amount, whether alone or as a part of a pharmaceutical composition. The therapeutically effective amount and the dosage administered will, of course, vary depending upon known factors, such as the pharmacodynamic characteristics of the particular agent and its mode and route of administration, the age, health and weight of the recipient; the severity and stage of the disease state or condition; the kind of concurrent treatment; the frequency of treatment; and the effect desired.

The total amount of the compound administered will also be determined by the route, timing and frequency of administration as well as the existence, nature, and extent of any adverse side effects that might accompany the administration of the compound and the desired physiological effect. It will be appreciated by one skilled in the art that various conditions or disease states, in particular chronic conditions or disease states, may require prolonged treatment involving multiple administrations. In these pharmaceutical compositions, the compound(s) of the present disclosure will ordinarily be present in an amount of about 0.5-95% weight based on the total weight of the composition. Multiple dosage forms may be administered as part of a single treatment.

In some embodiments, the therapeutically effective amount of a compound of the disclosure ranges from about 0.1 mg/kg/day to about 50 mg/kg/day. In some embodiments, the therapeutically effective amount ranges from about 0.5 mg/kg/day to about 30 mg/kg/day. In some embodiments, the therapeutically effective amount ranges from about 1 mg/kg/day to about 25 mg/kg/day. In some embodiments, the therapeutically effective amount ranges from about 2 mg/kg/day to about 20 mg/kg/day. In some embodiments, the therapeutically effective amount ranges from about 3 mg/kg/day to about 15 mg/kg/day. In some embodiments, the therapeutically effective amount ranges from about 4 mg/kg/day to about 10 mg/kg/day. In some embodiments, the therapeutically effective amount ranges from about 0.1 mg/kg/day to about 20 mg/kg/day. In some embodiments, the therapeutically effective amount ranges from about 0.1 mg/kg/day to about 15 mg/kg/day. In some embodiments, the therapeutically effective amount ranges from about 0.1 mg/kg/day to about 10 mg/kg/day. In some embodiments, the therapeutically effective amount ranges from about 0.1 mg/kg/day to about 5 mg/kg/day. In some embodiments, the therapeutically effective amount ranges from about 0.1 mg/kg/day to about 6.5 mg/kg/day. In some embodiments, the therapeutically effective amount ranges from about 0.1 mg/kg/day to about 9 mg/kg/day. In some embodiments, the therapeutically effective amount ranges from about 1 mg/kg/day to about 14 mg/kg/day.

In certain embodiments, the therapeutically effective amount is administered in one or more doses according to a course of treatment (where a dose refers to an amount of a compound of the invention administered in a single day). In certain embodiments, the dose is administered q.d. (1 time/administration per day). In certain embodiments, the dose is administered b.i.d. (2 times/administrations per day; for example, one-half of the effective amount in two administrations a day). In certain embodiments, the dose is administered t.i.d. (three times/administrations per day; for example, one-third of the effective amount in two administrations a day). When a dose is divided into multiple administrations per day, the dose may be divided equally or the dose may be divided unequally at each administration. Any given dose may be delivered in a single dosage form or more than one dosage form (for example, a tablet).

The amount of active ingredient that is combined with the inactive ingredients to produce a pharmaceutical compositions described herein will vary depending upon the host treated and the particular mode of administration. For example, in some embodiments, a dosage form for oral administration to humans contains approximately 1 to 1000 mg of a compound of the present disclosure formulated with an appropriate and convenient amount of pharmaceutically acceptable excipient. In some embodiments, the pharmaceutical compositions described herein contain about 1 to 800 mg, 1 to 600 mg, 1 to 400 mg, 1 to 200 mg, 1 to 100 mg or 1 to 50 mg of a compound of the present disclosure.

Materials and Methods

Compounds

The Pharmakon 1600 library was obtained from (MicroSource Discovery Systems, Inc., Gaylordsville, Conn.). Compounds were supplied as stock in DMSO. Additional compounds were obtained from commercially available sources. Escin for the further characterization experiments was obtained from Sigma-Aldrich (St. Louis, Mo.; cat. No. E1378) as a powder. Additional escin was obtained from MicroSource Discovery Systems, Inc. (Gaylordsville, Conn.) for additional validation.

Cell Culture

Fischer Rat Thyroid (FRT) cells were stably transduced with the UGAC stop codon, CFTR G542X and W1282X stop codons, and matched CFTR WT control cDNA using the Flp-In™ system per the manufacturer's protocol (Invitrogen). The cells were maintained and grown in Nutrient Mixture F-12 Ham (Sigma F6636) medium supplemented with 2.68 g/L sodium bicarbonate and 10% FBS.

Human bronchial epithelial (HBE) cells derived from lung explants carrying nonsense alleles (such as G542X or W1282X) either alone or in trans with F508del CFTR (G542X/ΔF508, W1282X/ΔF508) were expanded using conditional reprogramming (Liu X, et al., *Am J Pathol;* 180: 599-607, 2012), seeded onto permeable supports and grown in differentiating media for at least 6-8 weeks until terminally differentiated.

Luciferase HTS Reporter Assay

The luciferase assay was performed on a Pharmakon 1600 library to determine the efficacy of each compound in promoting read-through. 5 ul of each compound as a DMSO stock solution were dissolved in F-12 Ham medium and dispensed into separate wells of 384-well plates (Corning) using a BioMek FX. FRT cells (10,000 cells/well) containing the reporter gene construct (QXN UGAC) were then added using the Matrix WellMate. The plates were incubated for 24 hours at 37° C., 5% $CO_2$, and 95% humidity, after which firefly luciferase activity was determined by equilibrating the plates to room temperature, adding an equal volume of Promega BrightGlo (Promega), and reading enhanced luminescence with an Envision Plate Reader (PerkinElmer) within 5 minutes. Holding DMSO concentration constant at 0.3%, compounds were tested at 10 concentrations (100 nM to 30 μM) in a stacked intra-plate format, with 320 compound samples per plate serially diluted 1:2 sequentially across 10 plates. G418 (500 μg/ml) served as a positive control.

Transepithelial Chloride Conductance Assay

Stably transfected FRT cells as described herein cells were seeded onto Costar 24-well 0.4 μM permeable supports at a density of ~2×10$^6$ cells/filter and maintained at 37° C. with 5% $CO_2$. Transepithelial resistance was assessed using an epithelial voltmeter to ensure the formation of tight monolayers, as defined by resistance >6 kcm$^2$. During initial evaluation of agents, cells were treated with compounds (10 μM), vehicle control (0.3% DMSO), or positive control (250 μg/mL G418) for 48 hours before transepithelial conductance ($G_t$) was assessed; subsequent studies used other concentrations of compounds. Measurements were taken at baseline, after the addition of 20 μM forskolin (FSK, a cAMP agonist that stimulates CFTR activity) and 10 μM $CFTR_{Inh}$-172 (a CFTR-specific inhibitor).

Confirmatory Dual Luciferase Assay

The basic features of the dual luciferase reporter system have been described previously (Grentzmann G, et al., *RNA;* 4: 479-486, 1998). The UGA-containing read-through cassette used in this study (5'-AAA TCC CAA TGA CAT GCA GGA-3'; SEQ ID NO: 1) was inserted between the *Renilla* and firefly luciferase genes in the expression plasmid and stable FRT cell lines were made using the FlipIn™ system. These constructs were grown in the presence of lead compounds, vehicle control (0.3% DMSO), or positive control (250 μg/mL G418) for 24 hrs and the assay was performed as previously described (Xue X, et al., *American journal of respiratory cell and molecular biology;* 50: 805-816; 2014).

Using Chamber Studies in Primary Cell Monolayers

Short circuit current (Isc) was measured under voltage clamp conditions as previously described (Rowe S M, et al., *J Mol Med (Berl)*; 89: 1149-1161; 2011). Briefly, primary HBE cells as described herein were seeded on Costar 0.4-mm permeable supports ($5.3 \times 10^5$ cells/filter, 6.5 mm diameter; Bethesda, Md.) after coating with fibroblast-conditioned media (Liu X, et al., *Am J Pathol*; 180: 599-607, 2012). Well-differentiated cells were treated with compounds for 48 hours and Isc measurements were obtained by using an epithelial voltage clamp apparatus in Ussing chambers (Physiologic Instruments). After measuring the baseline Isc, amiloride (100 µM) was added to block the epithelial sodium channel activity followed by the addition of CFTR agonists (20 µM FSK and 10 µM VX-770). $CFTR_{Inh}$-172 (10 µM) was added at the end of experiment to block CFTR-dependent Isc. DMSO (0.1%) and G418 (250 µg/mL) served as vehicle and positive controls, respectively.

Horse Radish Peroxidase (HRP) CFTR Expression Assay

To measure cell surface expression of CFTR, FRT cells expressing the fusion protein of G542X CFTR and HRP were treated with 10 µM of lead compounds for 48 hours at 37° C. and 5% $CO_2$. Holding DMSO concentration at 0.3%, FRT cells were washed 4 times in PBS supplemented with 1 mM $MgCl_2$ and 0.1 mM $CaCl_2$ and then incubated with the HRP substrate (Fisher, #PI-34096, 15 µl/well) at room temperature for 10 minutes. The luminescent HRP signal was analyzed via a Synergy NEO microplate reader (BioTek Instruments).

Real-Time Polymerase Chain Reaction (RT-PCR)

RNA was isolated from FRT G542X cells treated with escin (10 µM) using Qiagen RNAeasy isolation kit (Qiagen) and real-time PCR was carried out using TaqMan One Step PCR master mix reagents (Applied Biosystems) as described previously (Sloane P A, et al., *PLoS One*; 7: e39809; 2012). Briefly, total RNA was isolated using the Qiagen RNeasy mini kit according to manufacturer's instructions. To prevent possible DNA contamination, samples were pretreated with RNase-free DNase (Qiagen, Valencia, Calif.). Sequence-specific primers and probes for human CFTR were purchased from Assays on Demand (Applied Biosystems; Assay ID for CFTR: Hs00357011_m1). The probe extends across the exon 21/22 boundary of the human CFTR sequence. TaqMan One Step PCR Master Mix Reagents Kit (Applied Biosystems) was used for reverse transcription and PCR. The reaction volume was 25 µl and contained 12.5 µl of 2× Master Mix without uracil-N-glycosylase, 0.625 µl of 40× MultiScribe and RNase Inhibitor Mix, 1.25 µl of 20× target primer and probe, 5.625 µl of nuclease-free water (Ambion, Austin, Tex.), and 5 µl of RNA sample. Reaction plates were covered with an optical cap and centrifuged briefly to remove bubbles. Thermocycler conditions were as follows: Stage 1: 48° C. for 30 min; Stage 2: 95° C. for 10 min; Stage 3: 95° C. for 15 sec, repeat 40 cycles, 60° C. for 1 min. All experiments were run in triplicate for verification. The relative transcript levels were normalized to FRT WT mRNA levels.

α-L-Iduronidase Activity Assay

α-L-iduronidase activity was determined as follows. Cell extracts were obtained from mouse embryonic fibroblast (MEF) cells homozygous for the W402X mutation and immortalized using the SV40 Large T antigen using a lentiviral expression system. α-L-iduronidase activity was determined as described by Wang et al. (Wang, D. et al., 2012; Mol Genet Metab 105: 116-125). Briefly, 4-methylumbelliferone iduronide (FMU) was added to the cell lysate as a substrate at low pH (for example, 130 mM sodium formate buffer, pH 3.5). The reaction was incubated for 72 h at 37° C. after which the reaction was quenched by the addition of high pH buffer (for example, glycine-NaOH buffer, pH 10.8). The fluorescence of the cleaved free FMU molecule was immediately measured at 365 nm excitation and 450 nm emission using a fluorometer and the amount of active iduronidase was expressed as nmol FMU released/mg protein/hour.

Statistics

Thresholds for hit identification on HTS assays were >95% of CI for negative controls. For TECC, Isc, Dual luciferase and HRP cell-based assays, descriptive statistics (mean, SD, and SEM) were compared using t tests or ANOVA performed using Graphpad Prism software (La Jolla, Calif.), and Microsoft Excel (Seattle, Wash.), as appropriate. All statistical tests were two sided and were performed at a 5% significance level (i.e., α=0.05).

EXAMPLES

Example 1—Development and Validation of Stable Cell Lines for Luciferase HTS Assay In previous publications, the Applicants have shown that in mammalian cells the four most common CF-related nonsense mutations (G542X, R553X, R1162X, and W1282X) are all relatively resistant to read-through induction by available drugs (Xue X, et al., *American journal of respiratory cell and molecular biology*; 50:805-816; 2014). As such, the goal was to identify compounds via HTS that would be efficient in promoting read-through of PTCs. To measure read-through activity, stable FRT cell lines were generated using dual-luciferase reporter constructs comprised of *Renilla* and firefly luciferase genes surrounding a CFTR read-through cassette with either G542X or UGAC sequence (FIG. 1A) (sequences designated SEQ ID NOS: 1 and 2 in FIG. 1A). G542X was selected because it is the most common CFTR-PTC nonsense mutation and the Applicants had previously established FRT G542X for measurements of CFTR function (Xue X, et al., *American journal of respiratory cell and molecular biology*; 50:805-816; 2014; Rowe S M, et al.; *J Mol Med (Berl)*; 89:1149-1161; 2011). UGAC was selected because it is the most responsive PTC to positive control agents. Use of two distinct constructs minimized bias and maximized the potential of identifying effective drugs.

Figure 1B:
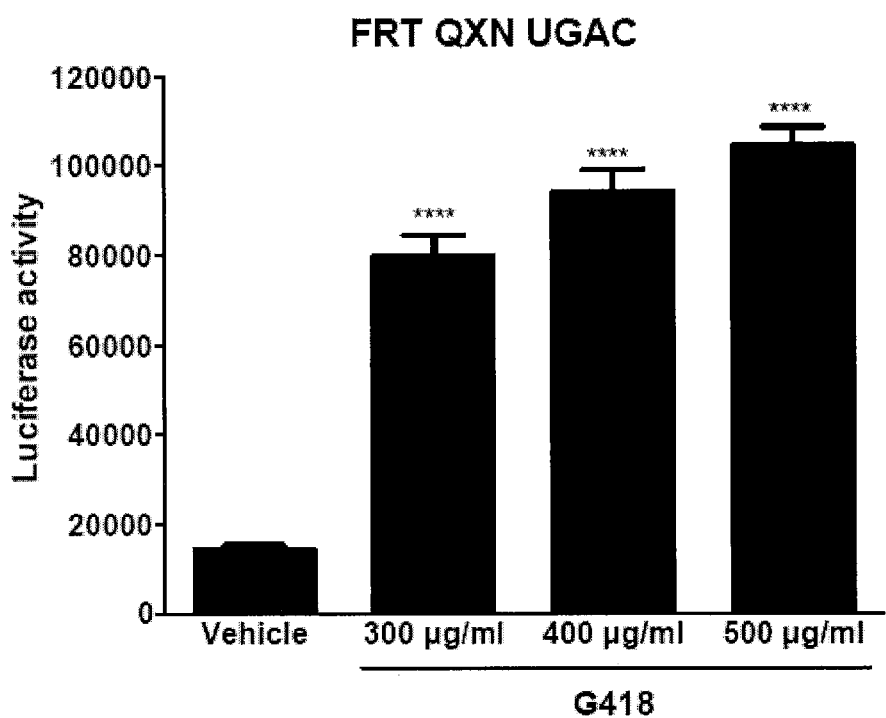
FIG. 1B shows the effect of G418 on luciferase activity in FTR QXN UGAC cells. FRT QXN UGAC cells were incubated with G418 (300 to 500 µg/ml) or vehicle control (0.3% DMSO) for 24 hours prior to determination of luciferase activity (****P<0.0001 as compared to vehicle control).
Figure 1C:
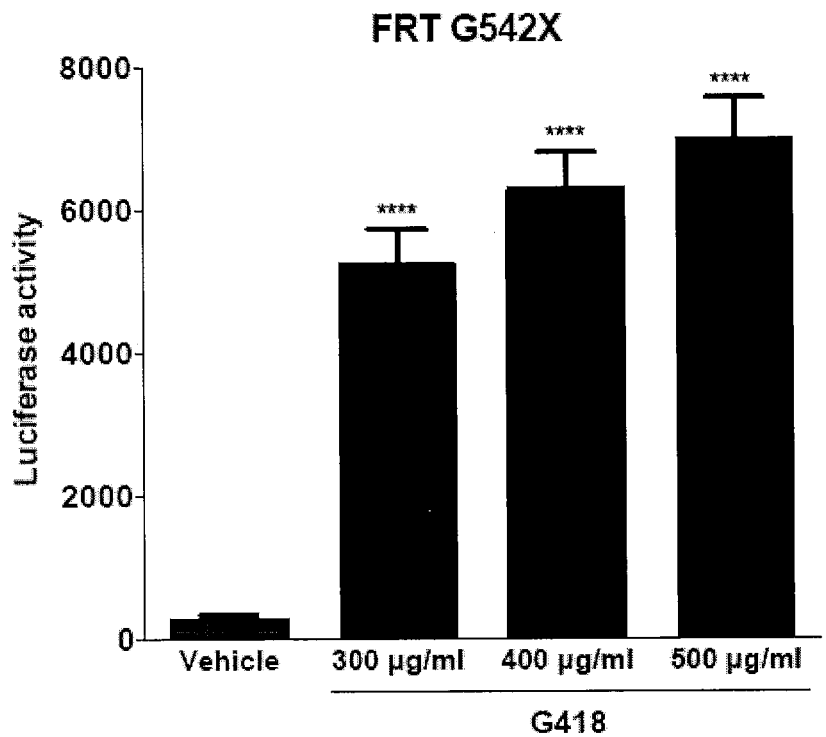
FIG. 1C shows the effect of G418 on luciferase activity in FTR G542X cells. FRT G542X cells were incubated with G418 (300 to 500 µg/ml) or vehicle control (0.3% DMSO) for 24 hours prior to determination of luciferase activity (****P<0.0001 as compared to vehicle control).
Figure 1D:
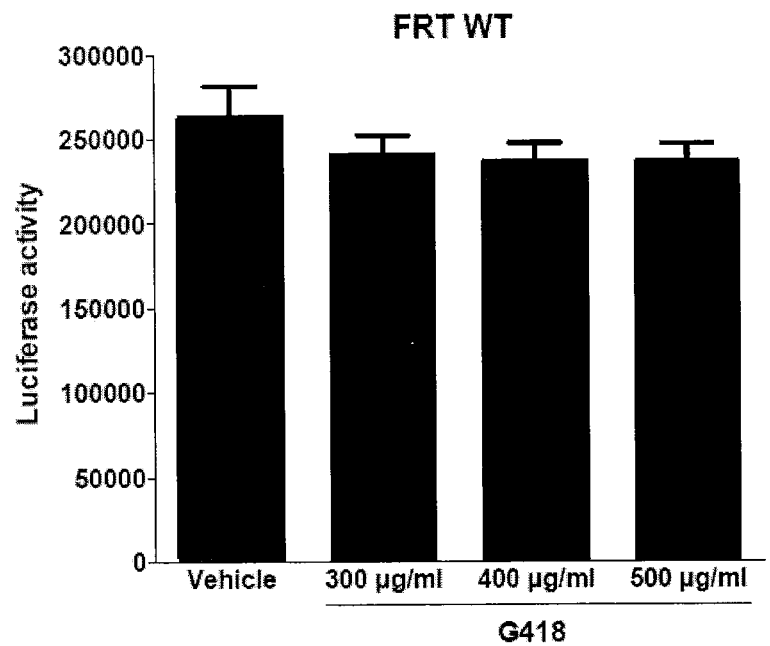
FIG. 1D shows the effect of G418 on luciferase activity in FTR WT cells. FRT wild type cells were incubated with G418 (300 to 500 µg/ml) or vehicle control (0.3% DMSO) for 24 hours prior to determination of luciferase activity.

To validate these cell lines, the cell lines were treated with G418, a read-through agent with established efficacy in vitro (Bedwell D M, et al.; *Nat Med*; 3:1280-1284; 1997), at doses up to from 300 to 500 µg/ml. An increase in luciferase activity indicates G418 stimulated read-through of the PTC in the constructs tested. G418 or vehicle control (0.3% DMSO) were pre-incubated with the cells for 24 hours prior to the determination of luciferase activity. G418 significantly increased firefly luciferase activity in a dose-dependent manner compared to DMSO-treated vehicle (P<0.0001) (FIGS. 1B and 1C) in FRT UQXN GAC cells and FRT G542X cells, but had no significant effect in matched FRT wild-type CFTR control cells (FIG. 1D), confirming that FRT G542X and FRT QXN UGAC cell lines would be informative models for use in the screens. For screening purposes, firefly luciferase levels were measured without assessment of *Renilla* expression as an indication of total construct expression.

Figure 2A:
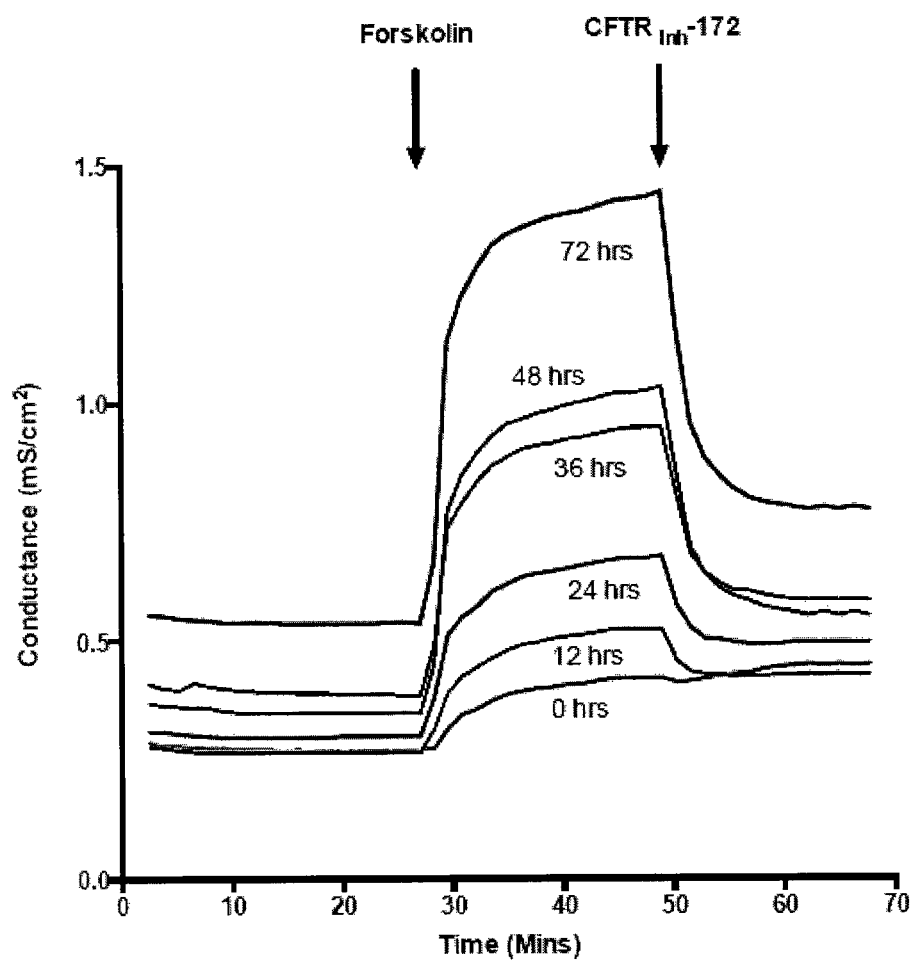
FIG. 2A shows the time-dependent effects of G418 on CFTR conductance in FRT G542X cells. FRT G542X cells were incubated with G418 (250 µg/ml) or vehicle control (0.3% DMSO) for 0 to 72 hours prior to determination of conductance. Immediately prior to the determination of conductance, cells were treated with FSK (20 µM); $CFTR_{Inh}$-172 (10 µM) was added at the end of the experiment to inhibit CFTR activity.
Figure 2B:
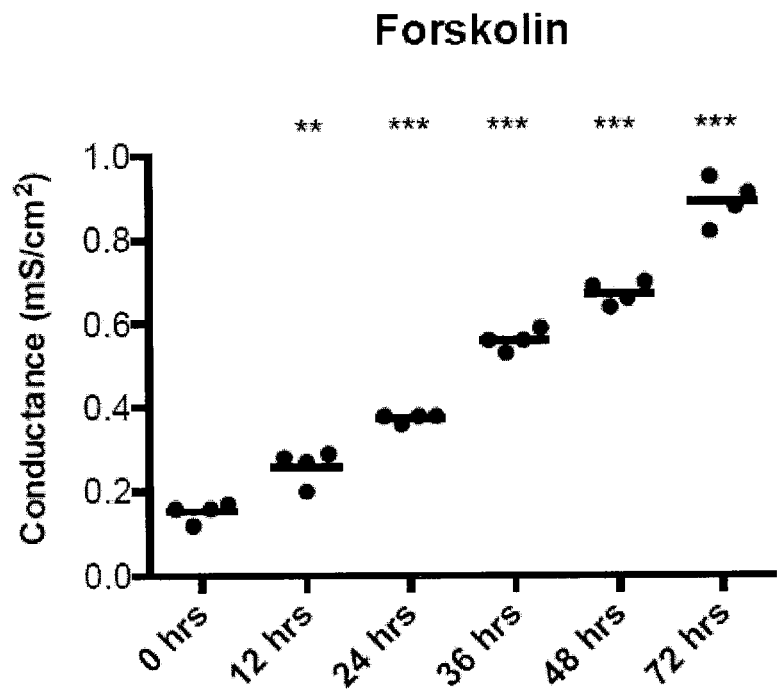
FIG. 2B shows a plot of the data in FIG. 2A demonstrating the stimulation of conductance by G418 in FRT G542X cells (P<0.01, *P<0.001 as compared to vehicle control).
Figure 2C:
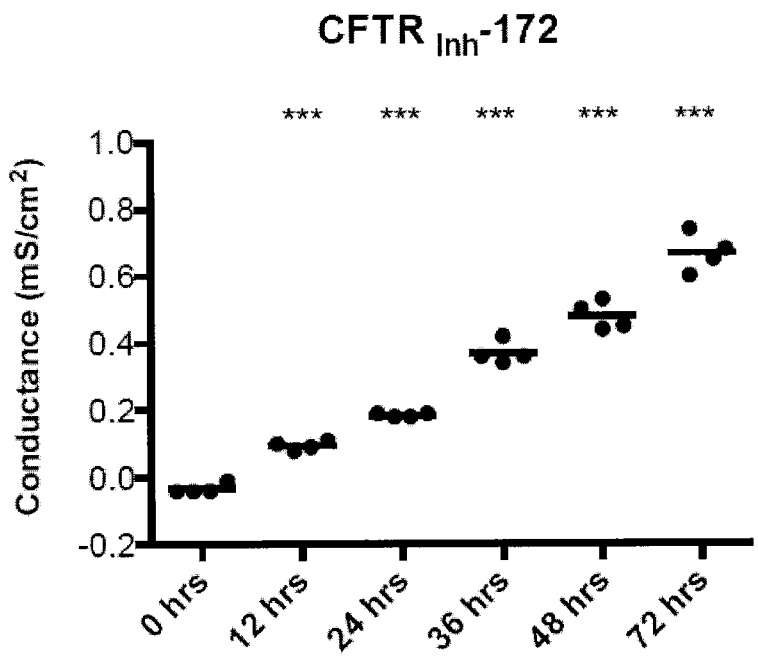
FIG. 2C shows a plot of the data in FIG. 2A demonstrating inhibition of G418 stimulated conductance by $CFTR_{Inh}$172 (***P<0.001 as compared to vehicle control).

To assess time-dependence, the efficacy of G418 in FRT G542X cells by determining the effect of G418 on CFTR conductance in the presence of forskolin. In this assay, an increase in CFTR conductance indicates G418 stimulated read-through of the PTC in the constructs tested. CFTR conductance in the presence of forskolin indicates FRT G542X cells were incubated with G418 (250 µg/ml) or vehicle control (0.3% DMSO) for 0 to 72 hours prior to determination of conductance. Immediately prior to the determination of conductance, cells were treated with FSK (20 µM); CFTR$_{Inh}$-172 (10 µM) was added at the end of the experiment to inhibit CFTR activity. There were time-dependent increases in forskolin-induced conductance, with maximal effects seen at 72 hrs (FIGS. 2A and 2B); this increase in forskolin-induced Gt was also sensitive to CFTR$_{Inh}$-172 (FIGS. 2A and 2C). For expediency, 48 hrs pre-incubation with the test compounds was chosen for subsequent studies since this time point resulted in >75% of the signal intensity and facilitated high-throughput evaluation. A similar time-dependent increase was also seen with the dual luciferase reporter (data not shown).

Example 2—High Throughput Screening

Upon establishing stable CFTR G542X and UGAC construct lines sensitive to read-through agent, HTS of 1600 clinically approved compounds was conducted. Two independent approaches were performed in parallel. Both a CFTR-mediated transepithelial chloride conductance (TECC) assay and a highly sensitive luciferase-based reporter assay (Xue X, et al.; *American journal of respiratory cell and molecular biology*; 50:805-816; 2014) were employed. The TECC assay provides a readout of CFTR activity and thus ensures physiological relevance. The luciferase-based reporter assay enables simultaneous testing of multiple concentrations of test compounds with much higher throughput.

In the TECC assay, FRT G542X cells were treated with a single dose (10 µM) of each compound. FRT G542X cells were incubated for 48 hours with the compounds prior or vehicle control (0.3% DMSO). During the assay the baseline conductance (Gt) was initially determined prior to the acute addition of forskolin (20 µM) and VX-770 (10 µM) to stimulate CFTR activity; the CFTR inhibitor, CFTR$_{Inh}$-172 (10 µM), was added to inhibit CFTR activity at the end of the assay. In these experiments, an increase in CFTR conductance indicates the compounds stimulated read-through of the PTC in the constructs tested and that the CFTR was functional.

Figure 3A:
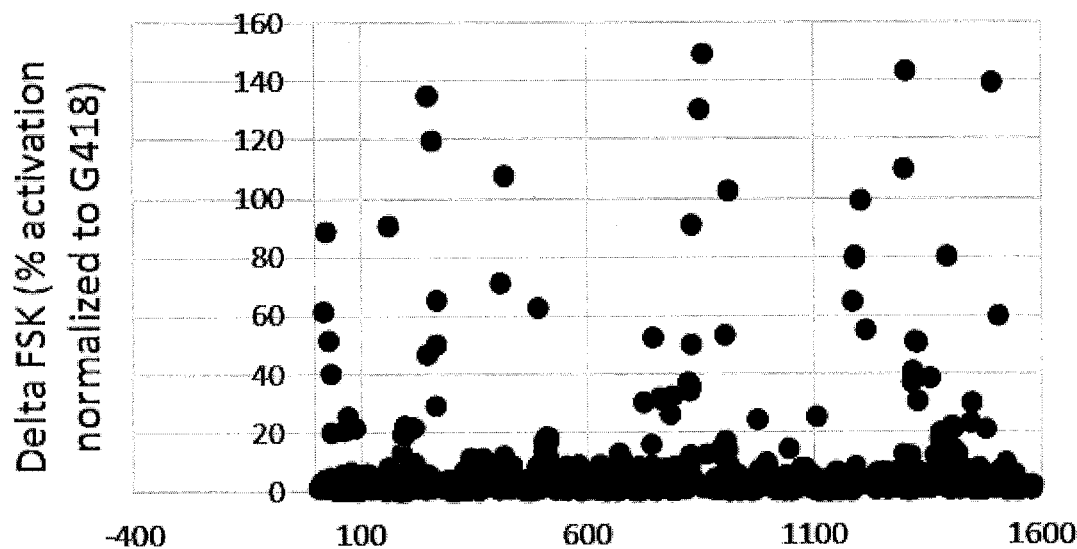
FIG. 3A shows a scatter plot demonstrating the percent change in CFTR conductance in the presence of forskolin (normalized to G418 control, 250 µg/ml) in FRT G542X cells. FRT G542X cells were incubated with the compounds (10 µM) or vehicle control (0.3% DMSO) for 48 hours. During the assay the baseline conductance (Gt) was initially determined prior to the acute addition of forskolin (20 μM) to stimulate CFTR activity; the CFTR inhibitor, CFTR$_{Inh}$-172 (10 μM), was added to inhibit CFTR activity at the end of the assay.

Of the 1600 compounds, 58 elicited an increase in CFTR conductance (as normalized to G418 at 250 µg/ml) in the presence of forskolin, representing a hit rate of 3.6% (FIG. 3A). Compounds that stimulated forskolin activity 20% normalized to the G418 positive control were considered active. Compounds that also responded to CFTR$_{Inh}$-172 after forskolin activation was measured in FRT cells with no CFTR expression (i.e. parental cells). Thirty agents increased forskolin-stimulated Gt above the ≥20% threshold, and thus were eliminated from the screen for their non-specific activity (data not shown).

Figure 3B:
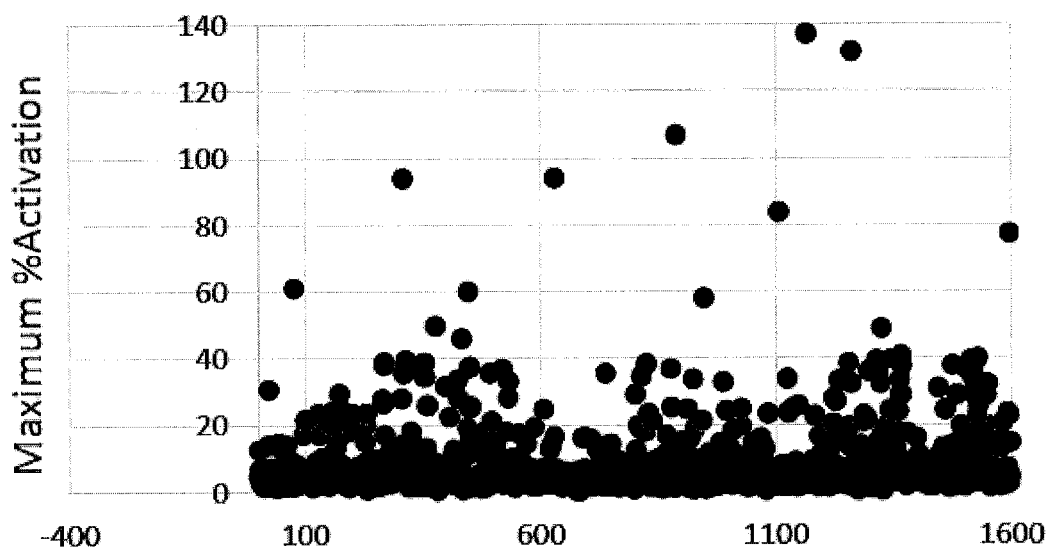
FIG. 3B shows a scatter plot demonstrating the maximum percent activation of luciferase activity in FRT QXN UGAC and FRT G542X cells. Cells were incubated with compound (0.1 μM-30 μM) for 48 hours prior to determination of luciferase activity.

In the firefly luciferase assay, FRT QXN UGAC and FRT G542X luciferase reporters were treated with the same 1600 compounds using a 10-point, serial 2-fold dilution concentration response assay (0.1 µM-30 µM). An increase in luciferase activity indicates the compounds stimulated read-through of the PTC in the constructs tested. The HTS assay was robust, with Z-values averaging 0.7. In FRT UGAC cells, the initial screen yielded 115 active hits as defined by maximum luciferase activation 20% relative to the G418 positive control (FIG. 3B). 90 of these compounds were excluded based on unfavorable medicinal properties.

Together, the TECC and luciferase screening yielded a total of 48 initial hits after accounting for specificity, medicinal properties and other factors. Five compounds were common hits for both assays at this stage.

Example 3—Evaluation of Lead Compounds

To prioritize which of the 48 read-through-positive compounds identified would be most efficacious in augmenting PTC read-through and restoring protein function, the TECC assay was repeated (in triplicate) using FRT G542X cells and FRT cells without CFTR (parental cells). Compounds (10 µM) or vehicle control (0.3% DMSO) were incubated for 48 hours with the cells. During the assay the baseline conductance (Gt) was initially determined prior to the acute addition of forskolin (20 µM) and VX-770 (10 µM) to stimulate CFTR activity; the CFTR inhibitor, CFTR$_{Inh}$-172 (10 µM), was added to inhibit CFTR activity at the end of the assay. G418 (250 µg/ml) was used as a positive control. In this assay, an increase in CFTR conductance indicates the compound stimulated read-through of the PTC in the constructs tested and that the CFTR was functional. The 48 compounds tested are provided in the Table 1 below (with the numerical designations corresponding to those shown in FIG. 4). The compounds in bold represent compounds that showed superior properties in one or more of the assays described and are useful as read-through stimulating agents.

TABLE 1

| | |
|---|---|
| 1 | ADENOSINE PHOSPHATE |
| 2 | ALBENDAZOLE |
| 3 | ALLANTOIN |
| 4 | AMINOPYRINE |
| 5 | AMIODARONE HYDROCHLORIDE |
| 6 | AMPHOTERICIN |
| 7 | APOMORPHINE HYDROCHLORIDE |
| 8 | ASCORBIC ACID |
| 9 | AZACITIDINE |
| 10 | CARBACHOL |
| 11 | CARSALAM |
| 12 | CINCHONINE |
| 13 | CISPLATIN |
| 14 | COLCHICINE |
| 15 | COLESEVALAM HYDROCHLORIDE |
| 16 | COLFORSIN |
| 17 | CYCLOHEXIMIDE |
| 18 | DERACOXIB |
| 19 | DOXORUBICIN |
| 20 | DOXYCYCLINE HYDROCHLORIDE |
| 21 | DROFENINE HYDROCHLORIDE |
| 22 | ESCIN |
| 23 | FENBENDAZOLE |
| 24 | FLUBENDAZOLE |
| 25 | FLUOROURACIL |
| 26 | FLUTAMIDE |
| 27 | FORMESTANE |
| 28 | HYCANTHONE |
| 29 | HYDROCORTISONE VALERATE |
| 30 | HYDROXYZINE PAMOATE |
| 31 | HYOSCYAMINE |
| 32 | MEBENDAZOLE |
| 33 | MECLOCYCLINE SULFOSALICYLATE |
| 34 | MELOXICAM SODIUM |
| 35 | METARAMINOL BITARTRATE |
| 36 | METHENAMINE |

TABLE 1-continued

| | |
|---|---|
| 37 | METHYLENE BLUE |
| 38 | NEOMYCIN SULFATE |
| 39 | NEOSTIGMINE BROMIDE |
| 40 | OXIBENDAZOLE |
| 41 | POTASSIUM p-AMINOBENZOATE |
| 42 | PREDNICARBATE |
| 43 | PYRONARIDINE TETRAPHOSPHATE |
| 44 | RIBOSTAMYCIN SULFATE |
| 45 | TEGASEROD MALEATE |
| 46 | TARGOCID |
| 47 | TERFENADINE |
| 48 | VENLAFAXINE HYDROCHLORIDE |

Figure 4:
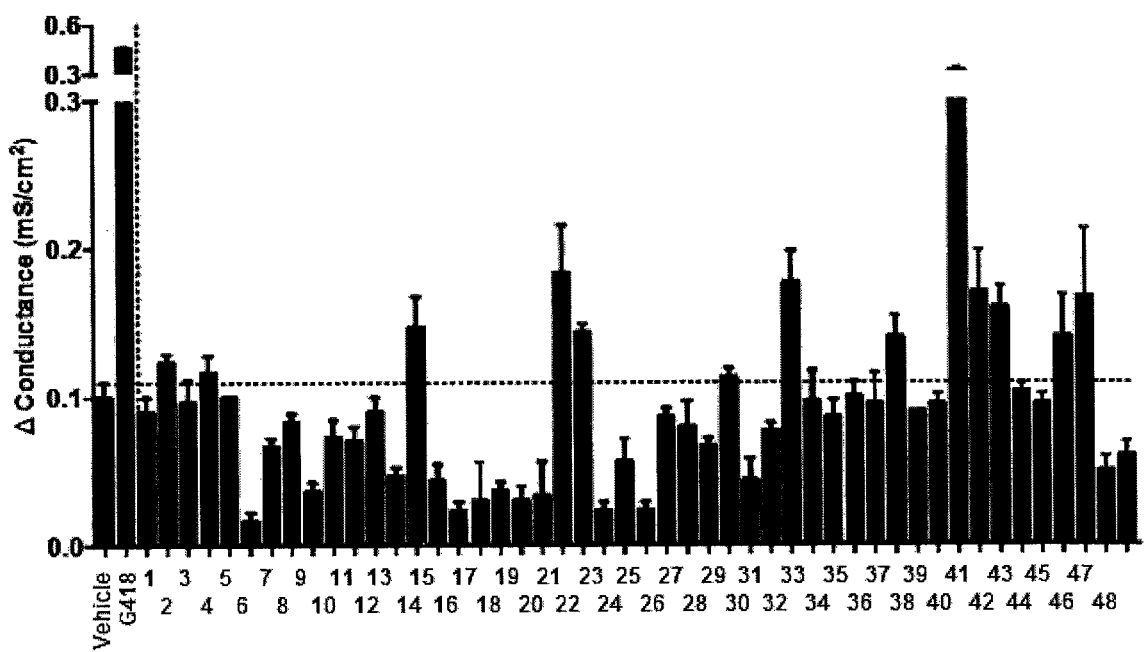
FIG. 4 shows the effect of selected compounds in on CFTR conductance in FRT G542X cells. FRT G542X cells were incubated with test compounds (10 μM), G418 (250 μg/mL) or vehicle control (0.3% DMSO) for 48 hours. During the assay the baseline conductance (Gt) was initially determined prior to the acute addition of forskolin (20 μM) to stimulate CFTR activity.

The change in conductance relative to vehicle control was assessed. Compounds that did not elicit an increase in CFTR conductance were eliminated. As shown in FIG. 4, 13 compounds consistently induced a forskolin-stimulated increase in conductance in FRT G542X cells (0.1±0.005). Those compounds that also increased conductance in FRT cells without CFTR (data not shown), and thus were excluded for poor specificity. The remaining compounds were deemed lead compounds. The lead compounds identified in the assays above were colchicine, cyclohexamide, doxorubicin, escin, pyranoradine tetraphosphate (PT), prednicarbate, oxibendazole and potassium p-aminobenzoate (PABA); albendazole and mebendazole were identified as lead compounds in additional experiments (data not shown).

Figure 5A:
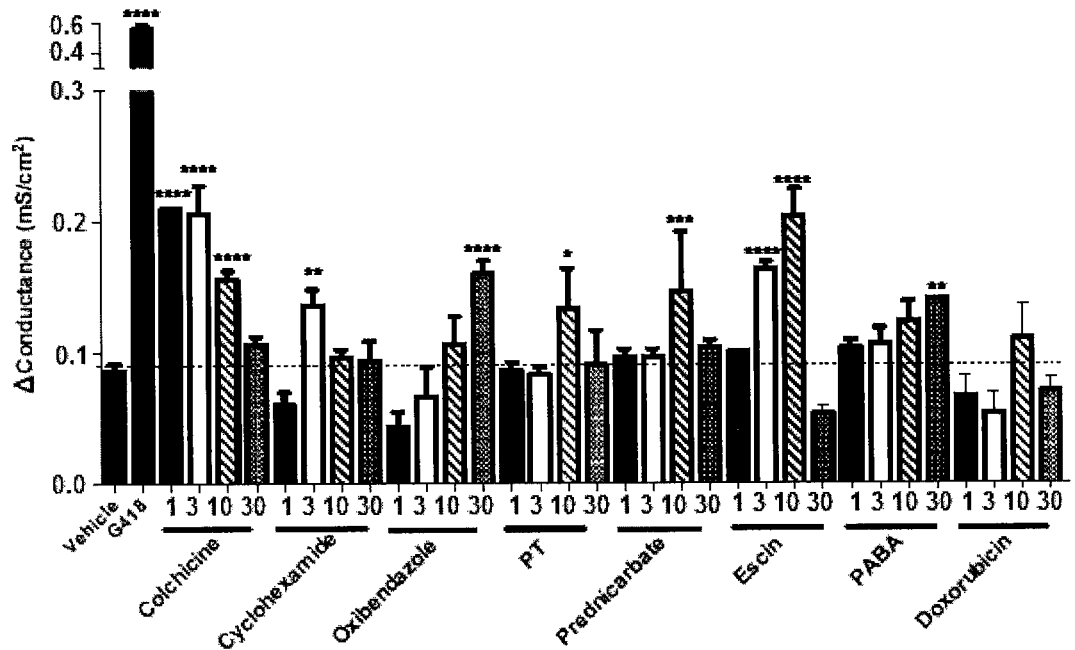
FIG. 5A shows the effect of selected compounds on CFTR conductance in FRT G542X cells. FRT G542X cells were incubated with test compounds (1 to 30 μM), G418 (250 μg/mL) or vehicle control (0.3% DMSO) for 48 hours. During the assay the baseline conductance (Gt) was initially determined prior to the acute addition of forskolin (20 μM) to stimulate CFTR activity. (*P<0.05, P<0.01, *P<0.001, ****P<0.0001).

A series of functional assays was performed to evaluate the efficacy of these lead compounds in greater detail. Using FRT G542X cells, the optimal dose of each compound in augmenting chloride conductance (FIG. 5A) was determined. FRT G542X cells were incubated with compound (1 μM to 30 μM), G418 (250 μg/mL) or vehicle control (0.3% DMSO) for 48 hours. The conductance assay was conducted as described in Example 2 above. In this assay, an increase in CFTR conductance indicates the compounds stimulated read-through of the PTC in the constructs tested and that the CFTR was functional. FRT G542X cells exhibited significantly higher ($P<0.05$) forskolin-stimulated CFTR conductance when treated with colchicine, cyclohexamide, escin, PT, prednicarbate, oxibendazole and PABA (FIG. 5A).

Figure 5B:
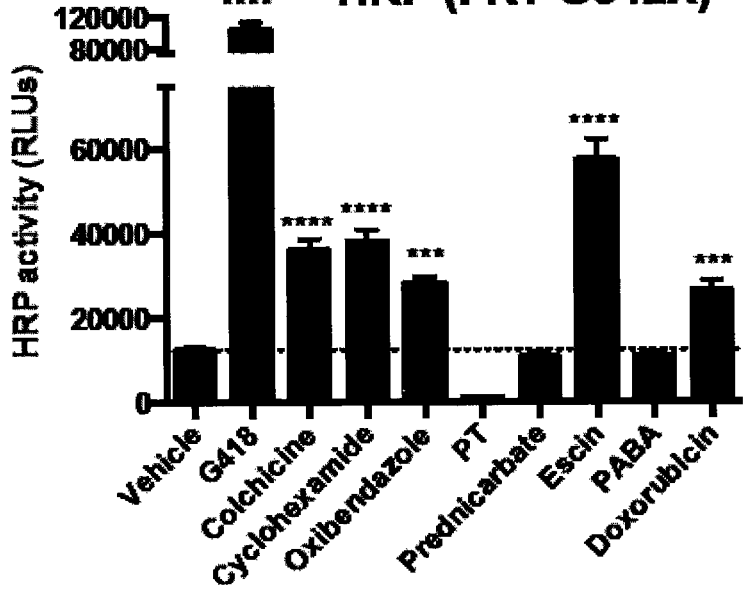
FIG. 5B shows the effect of selected compounds on HRP activity in FRT G542X cells. FRT G542X cells were incubated with compound (10 μM), G418 (250 μg/mL) or vehicle control (0.3% DMSO) for 48 hours prior to determination of HRP activity (*P<0.05, P<0.01, *P<0.001, ****P<0.0001 as compared to vehicle control).
Figure 5C:
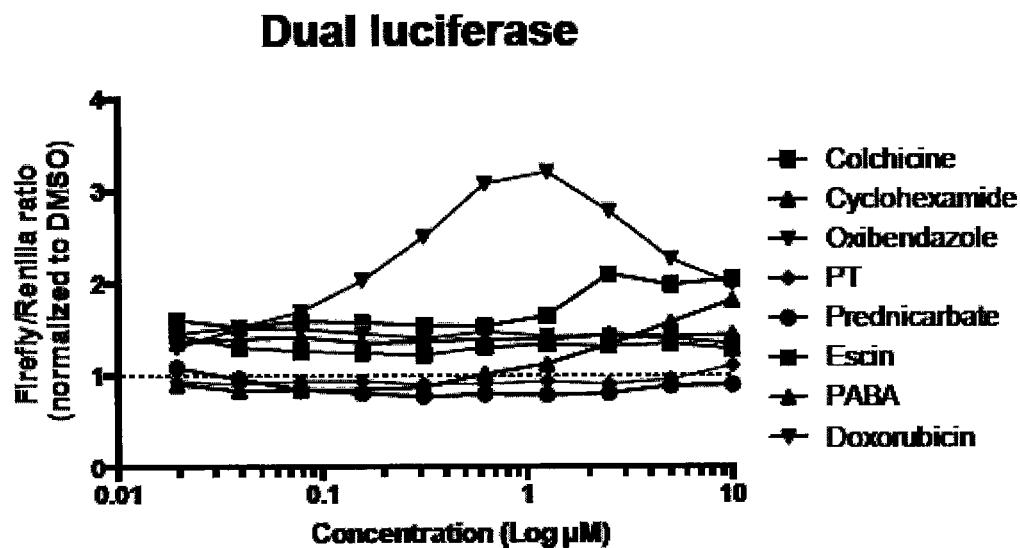
FIG. 5C shows the effect of selected compounds in the dual luciferase assay (ratio of firefly/renilla luciferase) in FRT QXN UGAC cells. FRT QXN UGAC cells were incubated with compound (0.01 μM to 10 μM), G418 (250 μg/mL) or vehicle control (0.3% DMSO) for 48 hours prior to determination of luciferase activity
Figure 5D:
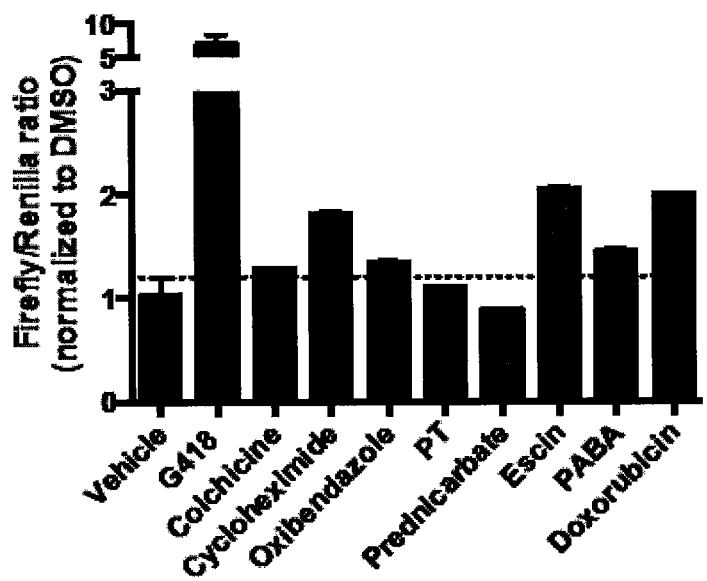
FIG. 5D shows the 8 identified lead compounds by Dual Luciferase Assay represented as fold increase in firefly/renilla ratio of highest efficacy.

Using FRT QXN UGAC cells, the optimal dose of each compound in the dual luciferase assay (ratio of firefly/*renilla* luciferase) was determined (FIG. 5C). In this assay, an increase in the luciferase ratio indicates the compounds stimulated read-through of the PTC in the constructs tested. FRT QXN UGAC cells were incubated with compound (0.01 μM to 10 μM), G418 (250 μg/mL) or vehicle control (0.3% DMSO) for 48 hours. Relative to vehicle control, FRT G542X cells showed optimal efficacy at a 10 μM dose (FIG. 5C). It should be noted that for escin, activity at ~2 μM was similar to that at 10 μM, and, for doxorubicin, activity peaked at ~1 μM (FIGS. 5C and 5D).

To obtain an additional readout of CFTR function, the effect of the lead compounds on CFTR cell surface expression was evaluated using the HRP assay. FTR G542X cells were incubated with compound (10 μM), G418 (250 μg/mL) or vehicle control (0.3% DMSO) for 48 hours prior to determination of HRP activity. In this assay, an increase in HRP activity indicates the compounds stimulated read-through of the PTC in the constructs tested. The HRP activity was significantly higher in FRT G542X cells treated with colchicine, cyclohexamide, oxibendazole, escin, and doxorubicin compared to vehicle control, validating functional measures above with a biochemical assay of CFTR expression (FIG. 5B).

Figure 5E:
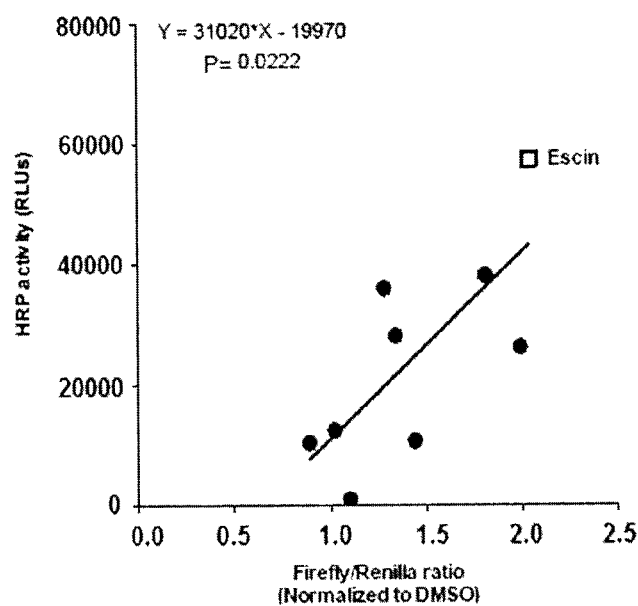
FIG. 5E shows the correlation between the HRP assay and the Dual Luciferase Assay.
Figure 5F:
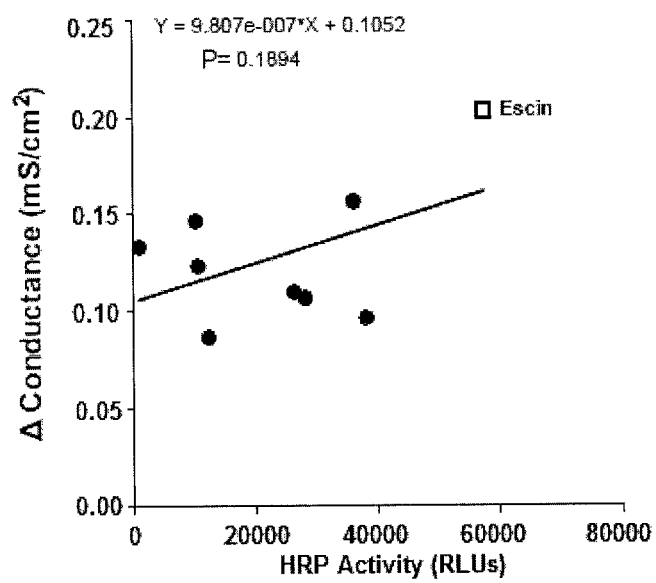
FIG. 5F shows the correlation between the TECC assay and the HRP assay.
Figure 5G:
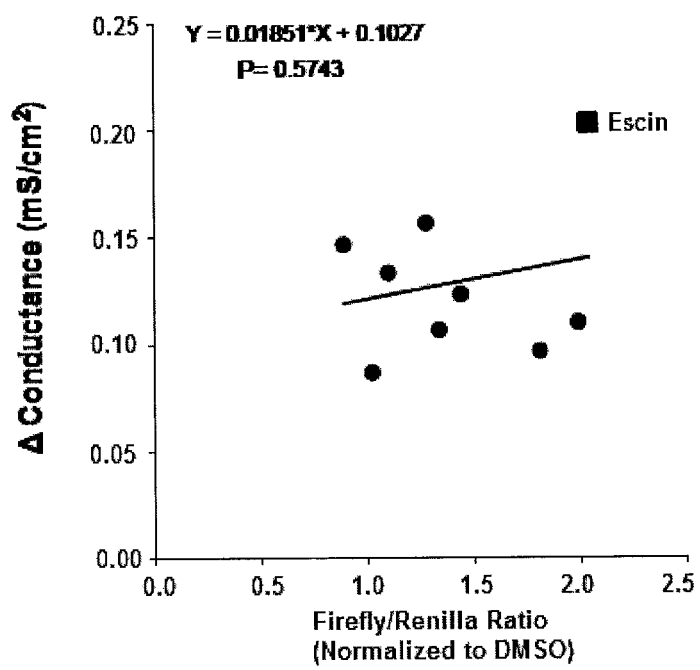
FIG. 5G shows the correlation between the TECC assay and the Dual Luciferase assay.

CFTR expression was also positively correlated with firefly luciferase activity ($P=0.02$) (FIG. 5E) and forskolin-stimulated increase in conductance (FIG. 5F). A moderate correlation between dual luciferase activity and forskolin-stimulated increase in conductance was also was observed (FIG. 5G). Overall, these results suggested that restoration of read-through activity was accompanied by restoration of CFTR function, further indicating the potential efficacy of these eight lead compounds.

Table 2 summarizes the results above for each of the 8 lead compounds. For the TECC assay, results are shown as mean Gt values (mS/cm$^2$±standard error). For the dual luciferase activity assay, results are shown as the mean firefly/*Renilla* ratio (±standard deviation). For the HRP assay results are expressed as detected protein expression in mean relative light units (RLU) (±standard error). For the HBE Ussing chamber assay results are expressed in mean Isc (uA/cm$^2$) (±standard error). Unless otherwise indicated, compounds were tested at 10 μM.

TABLE 2

| Agent | FRT G542X TECC Gt (mS/cm$^2$) Mean ± SE | FRT UGAC Dual Luciferase Firefly/Renilla Mean ± SD | FRT G542X HRP RLU Mean ± SE | HBE G542X/ΔF508 HBE Ussing Chamber Isc (μA/cm$^2$) Mean ± SE |
|---|---|---|---|---|
| Colchicine | 0.21 ± 0.0****,a | 1.28 ± 0.0.008 | 36000 ± 1554**** | 1.2 ± 0.2$^a$ |
| Cyclohexamide | 0.13 ± 0.06**,b | 1.81 ± 0.01 | 38171 ± 1618**** | 3.4 ± 0.07$^b$ |
| Oxibendazole | 0.16 ± 0.005****,c | 1.34 ± 0.01 | 28150 ± 908.6*** | 1.36 ± 0.04$^c$ |
| Pyronaridine Tetraphosphate (PT) | 0.13 ± 0.08* | 1.1 ± 0.005 | 1091 ± 98.8 | 6.2 ± 0.3** |
| Prednicarbate | 0.14 ± 0.02*** | 0.89 ± 0.0034 | 10515 ± 870.2 | 4.9 ± 1.2* |
| Escin | 0.20 ± 0.001**** | 2.04 ± 0.02 | 57402 ± 2836**** | 7.1 ± 0.3**** |
| Potassium p-Aminobenzoate (PABA) | 0.14 ± 0**,c | 1.44 ± 0.02 | 10811 ± 701.1 | 6.6 ± 1.2**,c |
| Doxorubicin | 0.11 ± 0.01 | 1.99 ± 0.007 | 26269 ± 1426*** | 2.38 ± 0.14 |

$^a$1 μM;
$^b$3 μM;
$^c$30 μM;
*$P<0.05$,
**$P<0.01$,
***$P<0.001$,
****$P<0.0001$

Example 4—Evaluation of Lead Compounds in Primary HBE Cells

Figure 6:
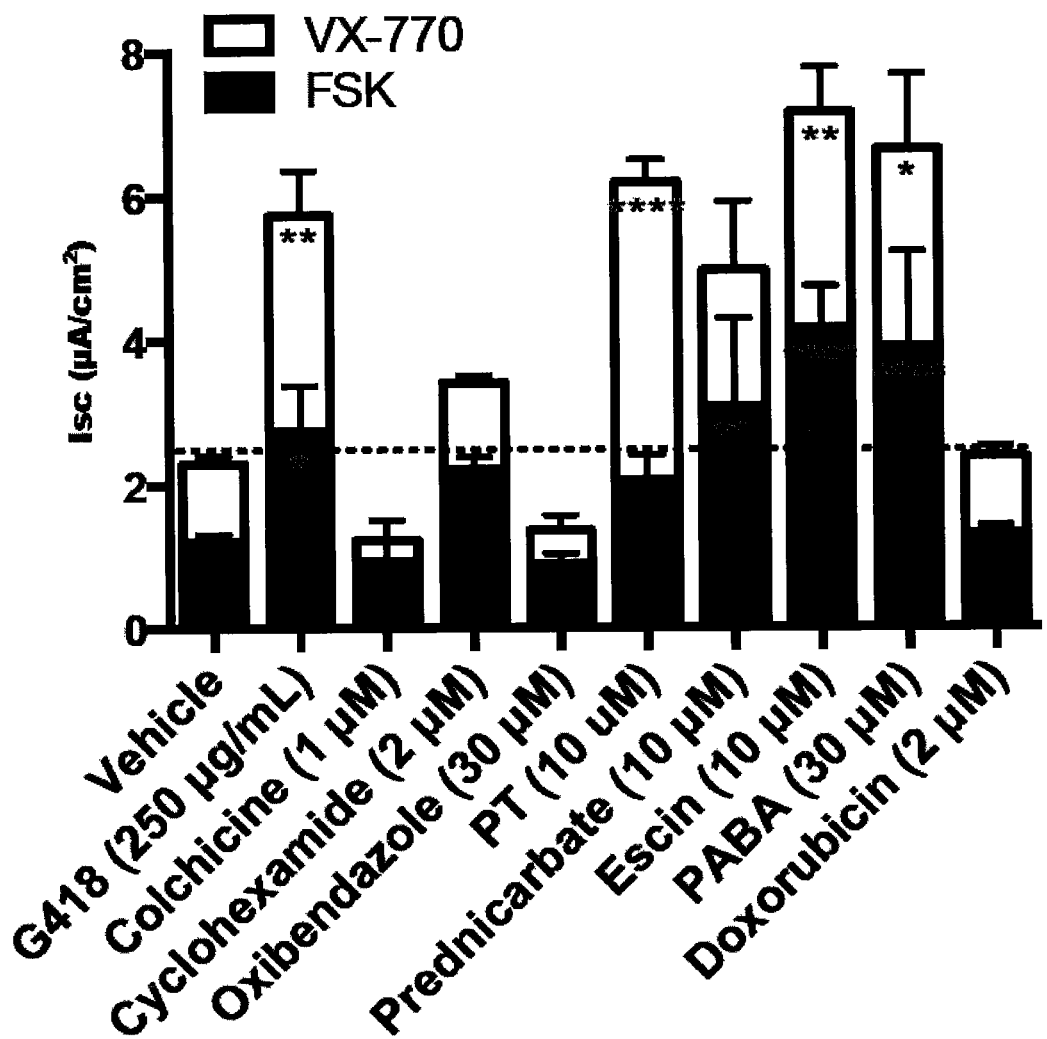
FIG. 6 shows the effect of G418, colchicine, cyclohexamide, oxibendazole, prednicarbate, escin, pyranoradine tetraphosphate, doxorubicin and para-amino benzoic acid on short circuit current (Isc) in primary HBE cells derived from a G542X/ΔF508 donor. G542X/ΔF508 cells were incubated with the test compounds for 48 hours at the indicated concentrations. To determine Isc, G542X/ΔF508 cells were treated with the CFTR agonists FSK (10 μM) and VX-770 (10 μM) Isc (*P<0.05, P<0.01, **P<0.0001 as compared to vehicle control).

Based on previous studies, primary HBE cells have been a valuable preclinical tool for predicting CF clinical trial results (Van Goor F, et al.; *Proc Natl Acad Sci USA;* 106:18825-18830; 2009; Ramsey B W, et al.; *N Engl J Med;* 365:1663-1672; 2011). Functional assays were performed with HBE cells derived from a G542X/ΔF508-CFTR heterozygous patient. It was shown previously that ivacaftor (formerly, VX-770), a CFTR potentiator that acts by increasing the open probability of CFTR at the cell surface, augments the ability of synthetic read-through drugs in restoring CFTR function (Xue X, et al.; *American journal of respiratory cell and molecular biology;* 50:805-8163; 2014). The effect of ivacaftor in combination with the optimal dose of each lead compound as determined in FIG. 5A was determined. To determine short circuit current (Isc), HBE cells were treated with amiloride (100 µM) to block epithelial sodium channel activity followed by the addition of CFTR agonists FSK (10 µM) and VX-770 (10 µM); CFTR$_{Inh}$-172 (10 µM) was added at the end of the experiment to block CFTR-dependent Isc. As shown in FIG. 6, ivacaftor significantly increased Isc following forskolin stimulation in cells treated with PT (6.2±0.3 uA/cm$^2$), prednicarbate (4.9±1.2 uA/cm$^2$), PABA (6.6±1.2 uA/cm$^2$) and escin (7.1±0.3 uA/cm$^2$) as compared to vehicle control. Augmentation was generally proportional to forskolin response, compatible with potentiator activity in this setting. Together, these results are consistent with prior work suggesting the promise of therapeutic strategies combining PTC suppression compounds with ivacaftor, and provide additional data supporting the utility of the compounds identified in the screen.

Example 5—Evaluation of Escin

Based on the results above, escin emerged as a particularly compelling compound among the eight leads. Escin elicited the highest levels of read-through (FIG. 5D), cell surface CFTR expression (FIG. 5B), and forskolin-dependent Isc alone and in combination with ivacaftor (FIG. 6). Importantly, escin, which has been used for its anti-inflammatory, anti-edematous, and vasoprotective properties as discussed above and is a readily available compound with no known side effects. As such, escin was an especially attractive compound for further testing in comparison to other lead agents that exhibited favorable responses.

Figure 7A:
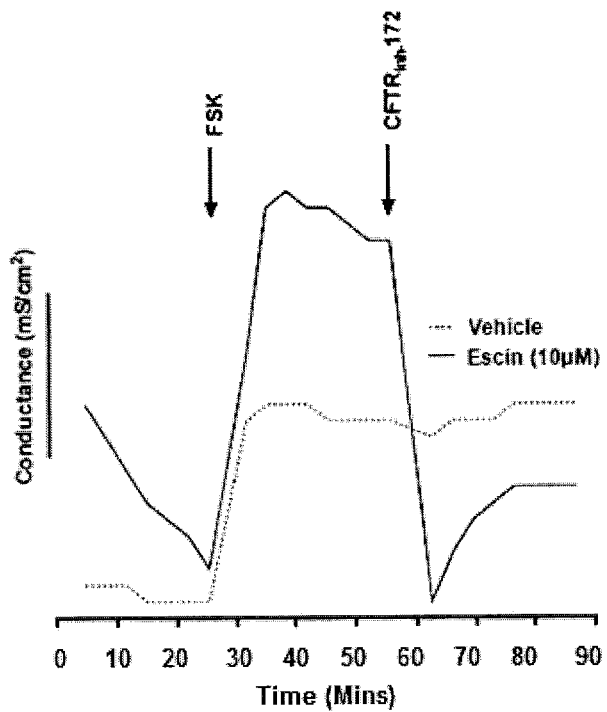
FIG. 7A shows the effect of escin on conductance in FRT G542X cells. FRT G542X cells were treated for 24 hours with escin (10 μM, solid lines) and vehicle control (0.3% DMSO, dotted lines). During the assay the baseline conductance (Gt) was initially determined prior to the acute addition of forskolin (20 μM) to stimulate CFTR activity; the CFTR inhibitor, CFTR$_{Inh}$-172 (10 μM), was added to inhibit CFTR activity at the end of the assay.
Figure 7B:
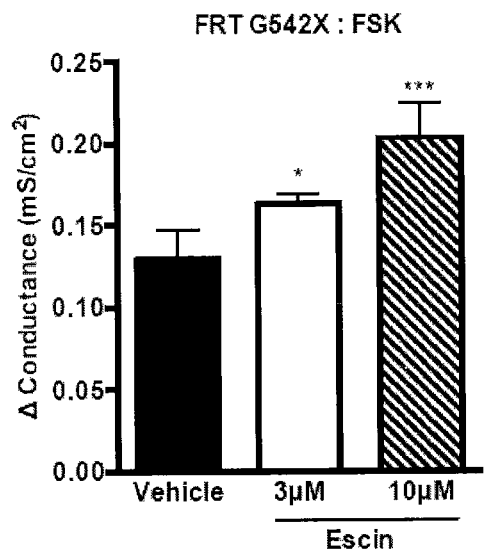
FIG. 7B shows the dose dependent effect of escin conductance in FRT G542X cells. FRT G542X cells were treated for 24 hours with escin (3 and 10 μM) and vehicle control (0.3% DMSO) prior to conductance measurement as described in FIG. 7A (*P<0.05, ***P<0.001 as compared to vehicle control).
Figure 7C:
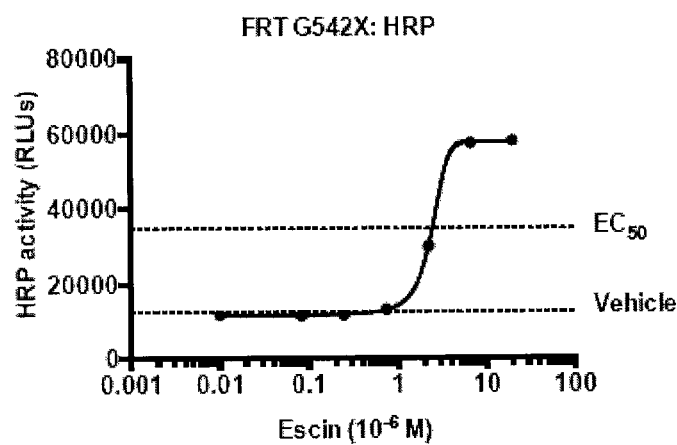
FIG. 7C shows the effect of escin on CFTR protein expression in the HRP assay. FRT G542X$^{HRP}$ cells were treated for 48 hours with escin (0.001 μM to 20 μM) and vehicle control (0.3% DMSO) prior to detection of cell-surface CFTR protein. The half-maximal effective concentration (EC$_{50}$) of escin for CTFR protein expression was determined.

In an independent evaluation of escin, escin showed a significant increase in forskolin-stimulated (20 µM) conductance (G$_t$) in FRT G542X cells pre-treated with 20 µM escin for 24 hours. The stimulatory effect of escin was completely attenuated by the addition of CFTR$_{Inh}$-172 (10 µM) (FIG. 7A). FIG. 7B shows effect of escin was dose-dependent (escin at 3 µM and 10 µM). While efficacy was observed for escin at both 3 µM and 10 µM concentrations in the conductance assays, escin was tested at a broader dose range (0.001 µM to 20 µM; 48 hour incubation) using the HRP assay (measuring cell surface protein expression) to further assess the effect of low doses of escin. FIG. 7C shows the EC$_{50}$ for escin in the HRP assay (FRT G542X cells) was 2.3 µM, indicating sufficient potency for human use.

Figure 7D:
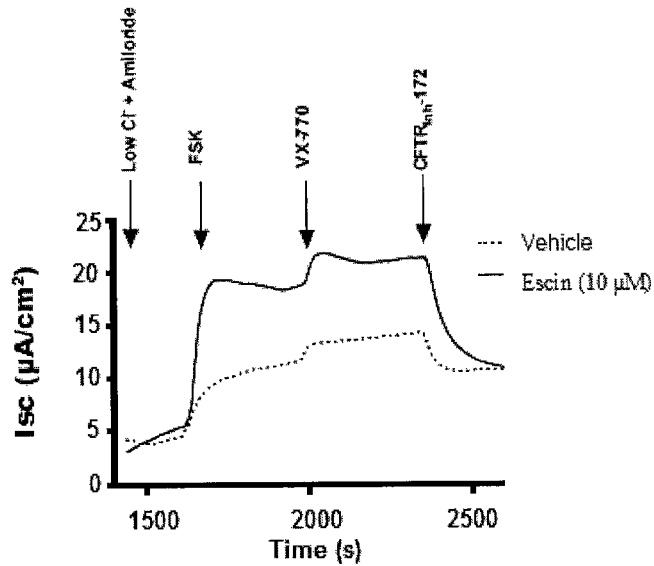
FIG. 7D shows the effect of escin on short circuit current (Isc) in HBE G542X/ΔF508 cells. HBE cells were incubated with escin (10 μM) or vehicle control (0.1% DMSO) for 48 hours. To determine Isc, HBE cells were treated with amiloride (100 μM) to block epithelial sodium channel activity followed by the addition of CFTR agonists FSK (10 μM) and VX-770 (10 μM) and the CFTR inhibitor CFTR$_{Inh}$-172 (10 μM) to inhibit CFTR activity.
Figure 7E:
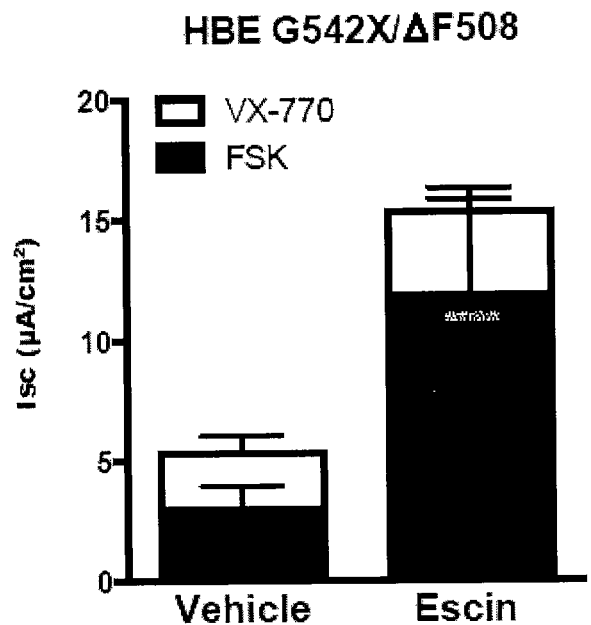
FIG. 7E shows the effect of escin on short circuit current (Isc) in HBE G542X/ΔF508 cells. The experimental set up is the same as described in FIG. 7D. Escin significantly increased FSK stimulated Isc in primary HBE cells, which was further increased by VX-770.
Figure 7F:
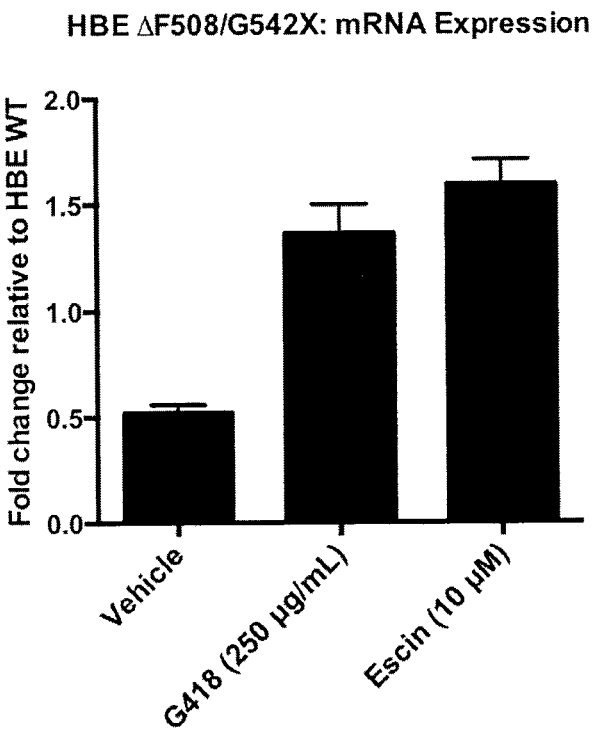
FIG. 7F shows the effect of escin on CFTR mRNA levels in HBE G542X/ΔF508 cells. Escin (10 μM), G4129 (250 μg/ml) and vehicle control (0.1% DMSO) were incubated for 48 hours in HBE cells. RNA was isolated from HBE cells and the levels of G542X mRNA was determined using real-time PCR as described herein. G542X mRNA levels were normalized to FRT wild-type mRNA levels.

Additional studies were performed in primary human bronchial epithelial (HBE) cells from a G542X/ΔF508 CF donor. HBE cells were incubated with escin (10 µM) or vehicle control (0.1% DMSO) for 48 hours. To determine short circuit current (Isc), HBE cells were treated with amiloride (100 µM) to block epithelial sodium channel activity followed by the addition of CFTR agonists FSK (10 tiM) and VX-770 (10 µM); CFTR$_{Inh}$-172 (10 µM) was added at the end of the experiment to block CFTR-dependent Isc. FIG. 7D shows escin (solid lines) induced a significant increase in forskolin-dependent Isc that was further increased with the addition of VX-770 as compared to vehicle control. The escin stimulated Isc was inhibited after administration of CFTR$_{Inh}$-172. CFTR activity upon stimulation with forskolin alone at 10 µM (11.9±2.5 µA/cm$^2$) was ~46% of wild type CFTR activity as determined in the Applicant's laboratory which was further stimulated by VX-770 (FIG. 7E). In addition, escin also enhanced CFTR mRNA expression levels. Escin (10 µM), G4129 (250 µg/ml) and vehicle control (0.1% DMSO) were incubated for 48 hours in HBE cells. RNA was isolated from HBE cells and the levels of G542X mRNA was determined using real-time PCR and normalized to FRT wild-type mRNA levels as described herein. FIG. 7F shows that escin increased G542X mRNA levels by ~2-fold as compared to vehicle control and showed greater enhancement than G418. This finding corroborated the Isc results and demonstrates that escin can both induce read-through of PTC and inhibit NMD.

To explore the potential benefit of escin for treatment of CF patients with other common nonsense mutations, escin was tested in FRT W1282X cells, HBE cells from a W1282X/ΔF508 heterozygous donor, HBE cells from a ΔF508/ΔF508 homozygous donor and HBE cells from a G542X/ΔF508 heterozygous donor. In these experiments, FRT and HBE cells were incubated with escin (10 µM), VX-809 (6 µM) and vehicle control (0.3% DMSO for FRT cells and 0.1% DMSO for HBE cells) as indicated for 48 hours. Individual assays were performed as described herein. The results are shown in FIGS. 7G to 7J.

Figure 7G:
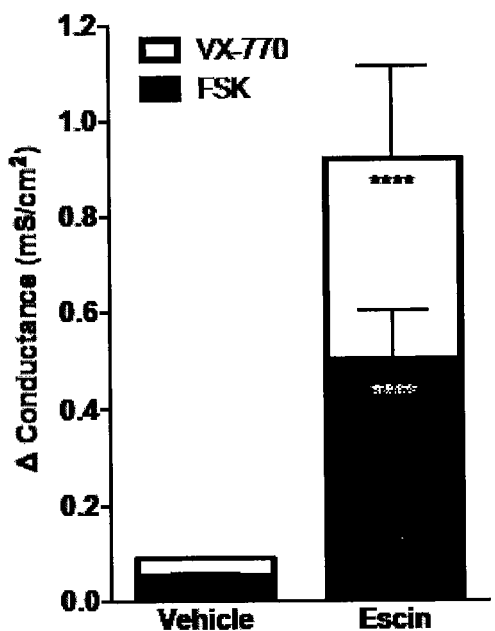
FIG. 7G shows the effect of escin on conductance in FRT W1282X cells. FRT W1282X cells were treated for 48 hours with escin (10 μM) and vehicle control (0.3% DMSO). Forskolin (20 μM) and VX-770 (10 μM) were added to stimulate CFTR immediately prior to determination of conductance (****P<0.001 as compared to vehicle control).
Figure 7H:
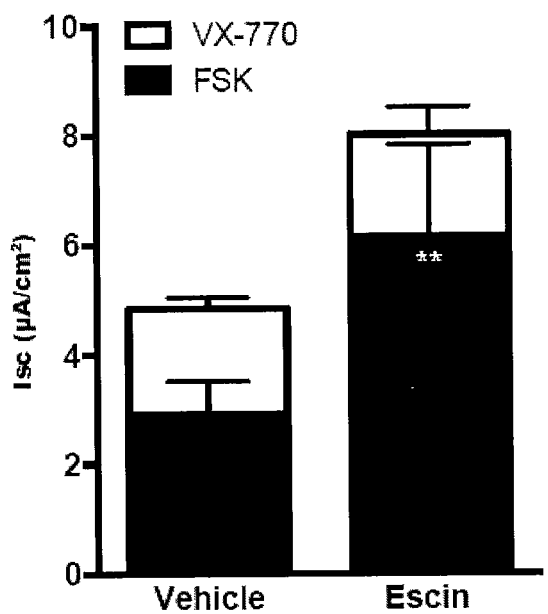
FIG. 7H shows the effect of escin on short circuit current (Isc) in primary HBE W1282X/ΔF508 cells. HBE W1282X/ΔF508 cells were treated for 48 hours with escin (10 μM) and vehicle control (0.1% DMSO). During the assay the baseline conductance (Gt) was initially determined prior to the acute addition of forskolin (20 μM) and VX-770 (10 μM) to stimulate CFTR activity; the CFTR inhibitor, CFTR$_{Inh}$-172 (10 μM), was added to inhibit CFTR activity at the end of the assay.
Figure 7I:
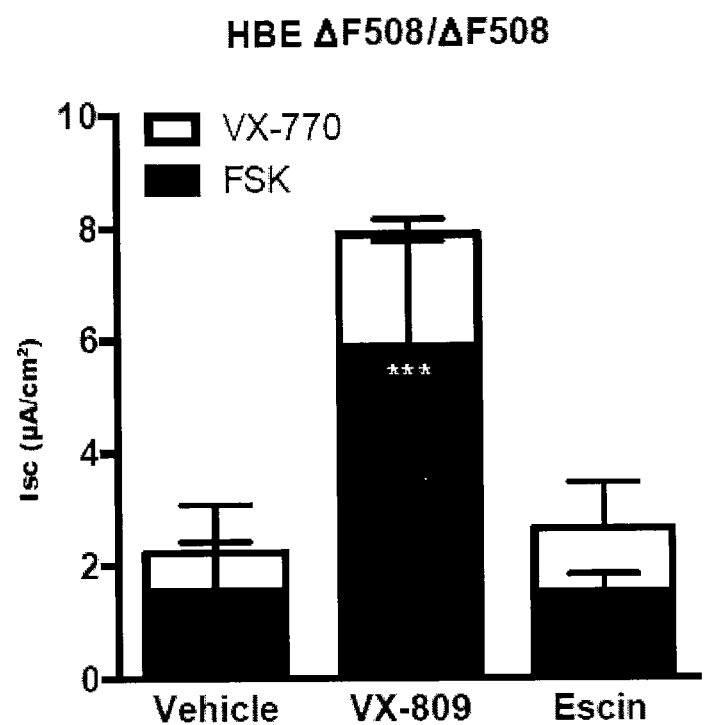
FIG. 7I shows the effect of escin in stimulating short circuit current (Isc) in primary HBE ΔF508/ΔF508 cells. HBE ΔF508/ΔF508 cells were treated for 48 hours with escin (10 μM) and vehicle control (0.1% DMSO). Forskolin (20 μM) and VX-770 (10 μM) were added to stimulate CFTR immediately prior to determination of Isc (***P<0.001 as compared to vehicle control).
Figure 7J:
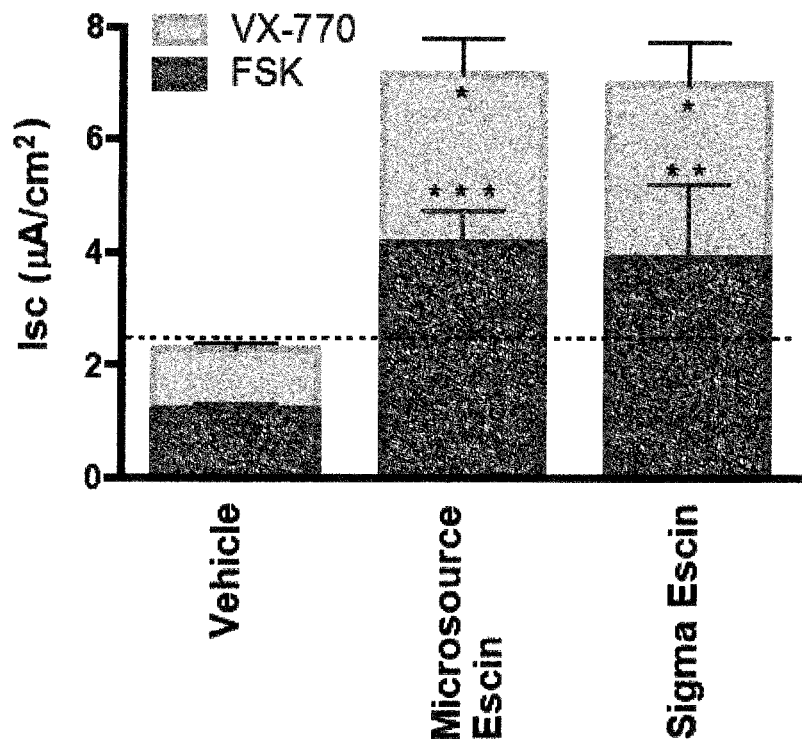
FIG. 7J shows the effect of escin on short circuit current (Isc) in primary HBE G542X/ΔF508 cells. HBE G542X/ΔF508 cells were treated for 48 hours with escin (10 μM) and vehicle control (0.1% DMSO). Forskolin (20 μM) and VX-770 (10 μM) were added to stimulate CFTR immediately prior to determination of Isc (***P<0.001 as compared to vehicle control).

FIG. 7G shows escin significantly enhanced CFTR function in FRT W1282X cells in the presence of forskolin; CFTR function was further enhanced by VX-770. FIG. 7H shows the same results for escin in primary HBE derived from a W1282X/ΔF508 heterozygous donor. To determine the specificity of escin in the stimulation of CFTR activity seen FIGS. 7G and 7H, escin was tested in HBE cells derived from a patient homozygous for ΔF508 mutation. As expected, escin had no effect in primary HBE ΔF508/ΔF508 cells (as these cells do not contain a PTC) as indicated by no increase in forskolin/VX-770 dependent Isc. In contrast, VX-809 showed a significant increase in CFTR activity as shown by an increase in forskolin-dependent Isc that was further increased with the addition of VX-770. VX-809 has been shown to partially restore CFTR function in patients with the ΔF508 mutation (Van Goor F, et al., *Proc Natl Acad Sci USA;* 108:18843-18848; 2011). This results shows that the effects of escin are due to induction of read-through and/or suppression of nonsense mediated mRNA decay.

Additional experiments were conducted in primary HBE from a G542X/ΔF508 donor to further analyze the effects of escin and VX-809 on CFTR activity. Escin stimulated CFTR activity as indicated by an increase in forskolin-dependent Isc that was further increased with the addition of VX-770 as previously see in FIG. 7E. VX-809 induced a modest increase in CFTR activity as indicated by a slight increase in forskolin-dependent Isc that was further increased with the addition of VX-770.

Figure 8:
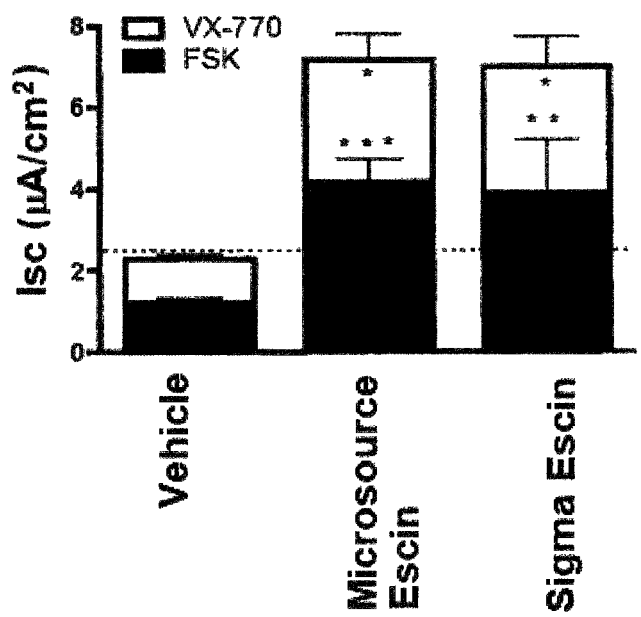
FIG. 8 shows the effect of two commercial sources of escin on short circuit current (Isc) in HBE G542X/ΔF508 cells. HBE G542X/ΔF508 cells were incubated with escin (10 μM for both sources) and vehicle control (0.1% DMSO) for 48 hours. Forskolin (20 μM) and VX-770 (10 μM) were added to stimulate CFTR immediately prior to determination of escin activity (*P<0.05, P<0.01, *P<0.001 as compared to vehicle control).

To compare commercial sources of escin, escin obtained from two different commercial vendors (Sigma-Aldrich and MicroSource Discovery Systems, Inc.) were compared in primary HBE from a G542X/ΔF508 CF donor. HBE G542X/ΔF508 cells were incubated with escin (10 μM for both sources) and vehicle control (0.1% DMSO) for 48 hours. During the assay the baseline conductance (Gt) was initially determined prior to the acute addition of forskolin (20 μM) and VX-770 (10 μM) to stimulate CFTR activity; the CFTR inhibitor, $CFTR_{fith}$-172 (10 μM), was added to inhibit CFTR activity at the end of the assay. Escin from either source induced a significant increase in CFTR activity as indicated by an increase in forskolin-dependent Isc that was further increased with the addition of VX-770 (FIG. 8).

Example 6—Escin Acts Synergistically with CFTR Correctors and Potentiators

As previously reported in the literature, the combination of CFTR correctors (such as VX-809) and CFTR potentiators (such as VX-770) act synergistically to improve CFTR function. To investigate the interaction of the read-through stimulating compounds of the disclosure and CFTR correctors and potentiators, the effect of escin in combination with both a CFTR corrector and a CFTR potentiator was investigated in triple combination studies performed in FRT W1282X cells. In these experiments, escin was used at 10 μM, G418 at 250 μg/ml, VX-770 at 10 μM and VX-809 at 6 μM. Compounds alone or in the indicated combination were pre-incubated with FRT W1282X cells for 48 hours. During the assay the baseline conductance (Gt) was initially determined prior to the acute addition of forskolin (20 μM) and VX-770 (10 μM) to stimulate CFTR activity; the CFTR inhibitor, $CFTR_{Inh}$-172 (10 μM), was added to inhibit CFTR activity at the end of the assay. Enhancement of PTC read-through by the compounds of the present disclosure was determined by an increase in CFTR conductance. CFTR conductance also indicated the CFTR was functional as a result of the read-through of the PTC.

Figure 9:
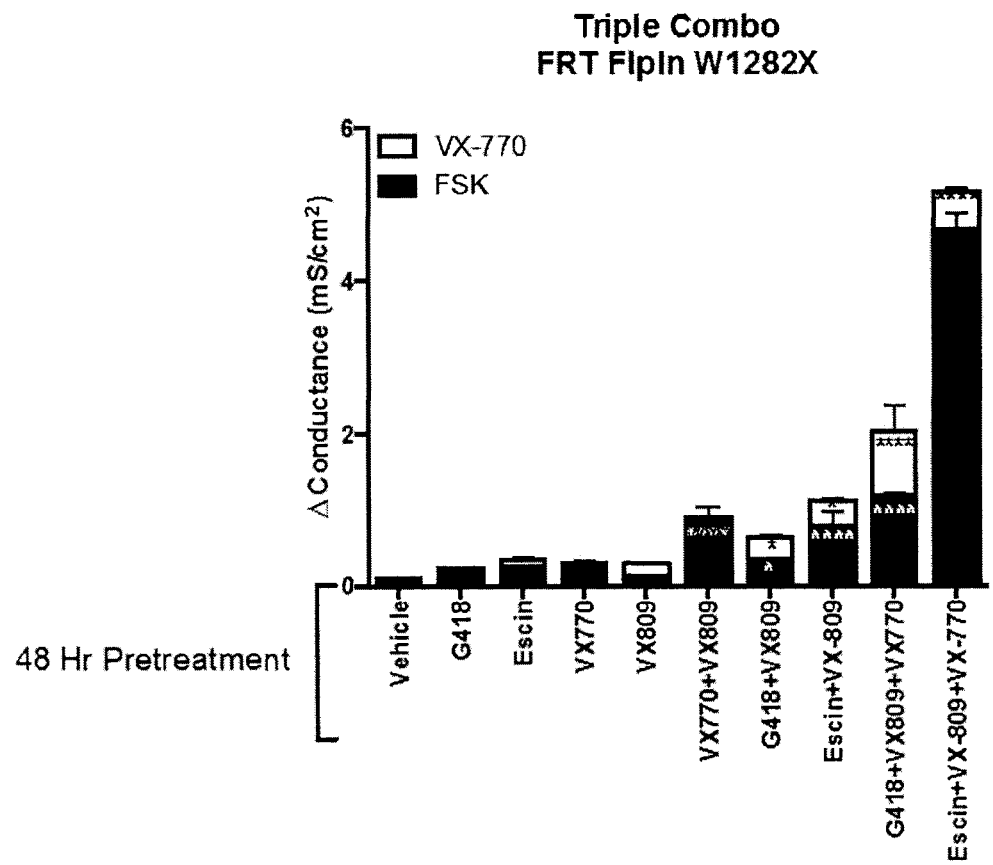
FIG. 9 shows the effect of escin in combination with a CFTR potentiator and a CFTR corrector on conductance in FRT W1282X. Escin (10 μM), G418 (250 μg/ml), VX-770 (10 μM) and VX-809 (6 pA4) either alone or in the indicated combinations were pre-incubated with FRT W1282X cells for 48 hours. During the assay the baseline conductance (Gt) was initially determined prior to the acute addition of forskolin (20 μM) and VX-770 (10 μM) to stimulate CFTR activity; the CFTR inhibitor, $CFTR_{Inh}$-172 (10 μM), was added to inhibit CFTR activity at the end of the assay ($*P<0.05$, $****P<0.0001$ as compared to vehicle control).

The results are shown in FIG. 9. Each compound alone enhanced CFTR function to varying degrees. The combination of VX-809 and VX-770 provided a significant increase in CFTR function, which was not increased with further addition of VX-770. The combination of VX-809 and escin also provided a significant increase in CFTR function, which was increased with further addition of VX-770. Similar results were seen for the combination of G418 (geneticin, an aminoglycoside compound that stimulates read-through) and VX-809, but to a lesser degree than the combination of escin and VX-809. When escin was combined with both VX-809 and VX-770, a synergistic increase in CFTR function was observed for the triple combination. Further addition of VX-770 also further enhanced CFTR function. While a significant enhancement in CFTR function was also seen for the triple combination of G418, VX-809 and VX-770, the enhancement was approximately 3-fold less than observed with escin, VX-809 and VX-770.

These results indicate that escin synergistically enhanced CFTR function in the presence of a CFTR corrector and a CFTR potentiator and enhanced CFTR function in the presence of a CFTR corrector and a CFTR potentiator individually.

Example 7—Escin Shows Synergy with NMD Inhibitors

Transcript including a PTC may be targeted for rapid degradation before they can be translated into protein through NMD. NMD is a surveillance pathway that exists in all eukaryotes that functions to reduce errors in gene expression by eliminating mRNA transcripts that contain PTCs. By decreasing the process of NMD, levels of an mRNA transcript containing a PTC are increased. Therefore, the transcript containing a PTC is available for translation in the presence of read-through stimulating compounds disclosed herein. A variety of small molecule NMD inhibitors (NMDIs) are known, including NMDI-1, NMDI-9, NMDI-25 and NMDI-14. In certain cases, the NMDIs inhibit the formation of protein complexes required for NMD. For example, NMDI-1 inhibits the HSMG5-hUPF1 complex and NMDI-14 inhibits the UPF1-SMG7 complex, which is required for NMD.

To investigate the interaction between the read-through stimulating compounds disclosed and NMDIs, the effect of escin in combination with two exemplary NMDIs, NMDI-1 and NMDI-14, was investigated. In these experiments, FRT G542X cells were used with escin (10 μM), NMDI-1 (80 μg/ml) and NMDI-14 (20 μg/ml). Compounds alone or in the indicated combination were pre-incubated with FRT G542X cells for 48 hours. During the assay the baseline conductance (Gt) was initially deteimined prior to the acute addition of forskolin (20 μM) and VX-770 (10 μM) to stimulate CFTR activity; the CFTR inhibitor, $CFTR_{Inh}$-172 (10 μM), was added to inhibit CFTR activity at the end of the assay. The same experiments were performed identically in FRT W1282X cells with escin and NMDI-14 only. Enhancement of PTC read-through by the compounds of the present disclosure was determined by an increase in CFTR conductance. CFTR conductance also indicated the CFTR was functional as a result of the read-through of the PTC.

Figure 10A:
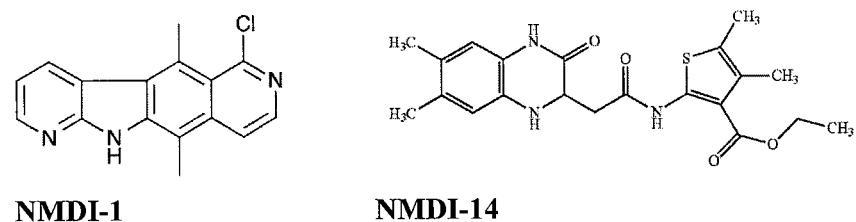
FIG. 10A shows the structure of NMDI-1 and NMDI-14.
Figure 10B:
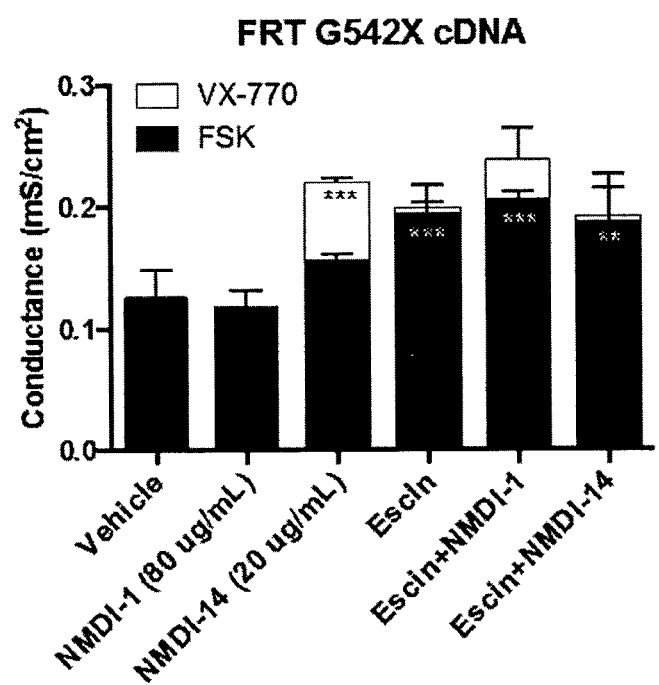
FIG. 10B shows the effect of escin in combination with NMDI-1 or NMDI-14 on conductance in FRT G542X cells. Escin (10 μM), NMDI-1 (80 μg/ml) and NMDI-14 (20 μg/ml), either alone or in the indicated combinations, were pre-incubated with FRT G542X cells for 48 hours. During the assay the baseline conductance (Gt) was initially determined prior to the acute addition of forskolin (20 μM) and VX-770 (10 μM) to stimulate CFTR activity; the CFTR inhibitor, $CFTR_{Inh}$-172 (10 μM), was added to inhibit CFTR activity at the end of the assay ($P<0.01$, $*P<0.001$ as compared to vehicle control).
Figure 10C:
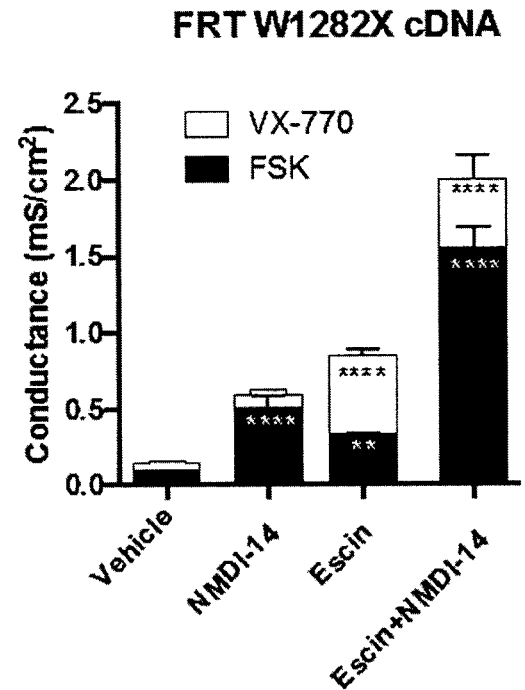
FIG. 10C shows the effect of escin in combination with NMDI-14 on conductance in FRT W1282X cells. Escin (10 μM) and NMDI-14 (20 μg/ml), either alone or in the indicated combinations, were pre-incubated with FRT W1282X cells for 48 hours prior to determination of conductance as described in FIG. 10B ($P<0.01$, $**P<0.0001$ as compared to vehicle control).

The results are shown in FIGS. 10B and 10C. FIG. 10B shows that in FRT G542X cells. Escin stimulated CFTR function alone as previously shown in the presence of both VX-770 and forskolin. NMDI-1 alone had little effect on CFTR function. The combination of NMDI-1 and escin resulted in improvement in CFTR function, particularly in the presence of VX-770, as compared to escin alone. NMDI-14 alone in the presence of VX-770 significantly increased CFTR function. The combination of NMDI-14 and escin did not result in further improvement in CFTR function as compared to escin alone.

FIG. 10C shows that in FRT W1282X cells. Escin stimulated CFTR function alone as previously shown in the presence of both VX-770 and forskolin. NMDI-14 alone in the presence of VX-770 and forskolin significantly increased CFTR function. The combination of NMDI-14 and escin showed a synergistic increase in CFTR function in the presence of both VX-770 and forskolin as compared to escin alone.

These results confirm that compounds of the present disclosure can stimulate read-through of CFTR PTCs and that the combination with NMDIs can further enhance the activity of the read-through stimulating compounds of the present disclosure.

Example 8—Aminoglycosides do not Substantially Antagonize the Effect of Escin

Aminoglycosides are a class of antibacterial agents used mainly to treat Gram-negative bacterial infections. Aminoglycosides have been shown to reduce the fidelity of translation by inhibition of ribosomal proof reading, allowing erroneous insertion of amino acids at nonsense codons and continued translation to the 3' end of the gene Amino glycosides bind to the decoding site of ribosomal RNA of both prokaryotes and eukaryotes and bring about a conformational change that reduces discrimination between cognate and near-cognate tRNA, permitting an amino acid to be inserted at the stop codon. The net effect is continuation of translation through to the natural stop codon.

It has been reported that aminoglycosides interfere with the action read-through stimulating compound. To investigate the interaction between the read-through stimulating compounds disclosed and aminoglycosides, the effect of escin in combination with two exemplary aminoglycosides, tobramycin and gentamicin, was investigated. In these experiments, FRT W1282X cells were used with escin (10 μM), tobramycin (150 μgimp and gentamicin (250 μg/ml). Compounds alone or in the indicated combination were pre-incubated with FRT W1282X cells for 48 hours. During the assay the baseline conductance (Gt) was initially determined prior to the acute addition of forskolin (20 μM) and VX-770 (10 μM) to stimulate CFTR activity; the CFTR inhibitor, $CFTR_{Inh}$-172 (10 μM), was added to inhibit CFTR activity at the end of the assay Enhancement of PTC read-through by the compounds of the present disclosure was determined by an increase in CFTR conductance. CFTR conductance also indicated the CFTR was functional as a result of the read-through of the PTC.

Figure 11:
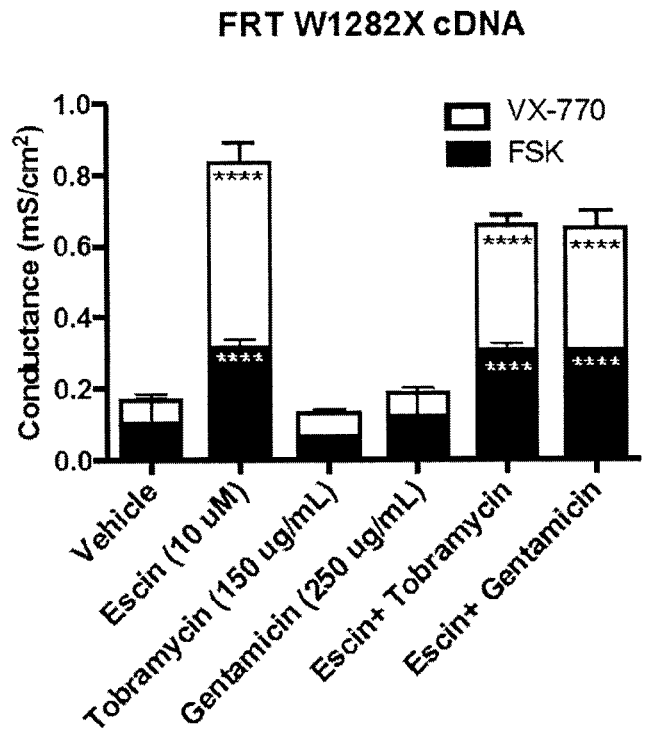
FIG. 11 shows the effect of escin in combination with the aminoglycosides tobramycin or gentamicin on conductance in FRT W1282X cells. Escin (10 μM), tobramycin (150 μgimp, gentamicin (250 μg/ml) and vehicle control (0.3% DMSO), either alone or in the indicated combinations, were pre-incubated with FRT W1282X cells for 48 hours. During the assay the baseline conductance (Gt) was initially determined prior to the acute addition of forskolin (20 μM) and VX-770 (10 μM) to stimulate CFTR activity ($****P<0.0001$ as compared to vehicle control).

The results, provided in FIG. 11, show that neither tobramycin nor gentamicin in combination with escin interfere with escin stimulation of CFTR activity to a significant degree nor augment the stimulation of CFTR activity by escin. Escin stimulated CFTR function alone as previously shown in the presence of both VX-770 and forskolin. In contrast, tobramycin and gentamicin alone did not stimulate CFTR function either in the presence of VX-770 or forskolin. The combination of escin and tobramycin or escin and gentamicin in the presence of forskolin demonstrated the aminoglycosides did not interfere with escin stimulation of CFTR activity or further increase escin stimulation of CFTR activity as compared to escin alone. The combination of escin and tobramycin or escin and gentamicin in the presence of VX-770 showed slightly decreased CFTR stimulation as compared to escin alone, but the CFTR stimulation observed with the combinations was robust and statistically significant. As for the combinations with forskolin, the neither tobramycin nor gentamicin further increased escin stimulation of CFTR activity.

These results confirm that compounds of the present disclosure can stimulate read-through of CFTR PTCs and that the combination with aminoglycosides do not significantly inhibit the activity the read-through stimulating compounds of the present disclosure.

Example 9—Escin Acts Synergistically with CFTR Correctors and Potentiators

As discussed in Example 6, CFTR potentiators and correctors have been shown to be efficacious in the treatment of CF. In this example, an additional CFTR potentiator (GP-5) and an additional CFTR corrector (C1 in combination with C2) along with VX-809 were investigated to determine their interaction with the read-through stimulating compounds of the disclosure.

Figure 12A:
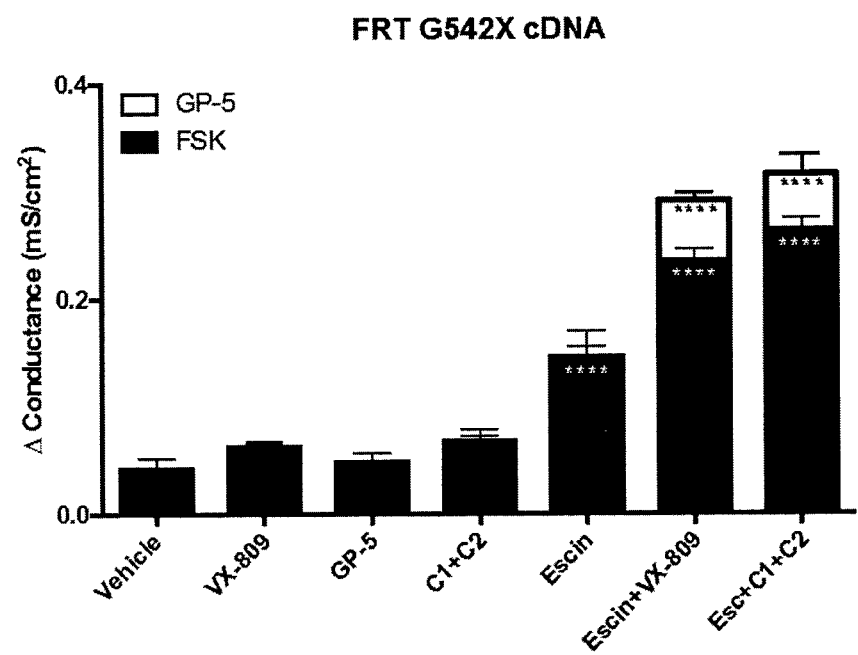
FIG. 12A shows the effect of escin in combination with CFTR potentiators (GP-5) and correctors (VX-809 and the combination of C1 and C2) on conductance in FRT G542X cells. Escin (10 μM), VX-908 (3 μM), GP-5 (10 μM), C1+C2 (10 μM) and vehicle control (0.3% DMSO), either alone or in the indicated combinations, were pre-incubated with FRT G5422X cells for 48 hours. During the assay the baseline conductance (Gt) was initially determined prior to the acute addition of forskolin (20 μM) and VX-770 (10 μM) to stimulate CFTR activity ($****P<0.0001$ as compared to vehicle control).

FIG. 12A shows the effect of escin in combination with the CFTR correctors VX-809 and the combination of C1+C2 in FRT G542X cells Enhancement of PTC read-through by the compounds of the present disclosure was determined by an increase in CFTR conductance. CFTR conductance also indicated the CFTR was functional as a result of the read-through of the PTC. Escin (10 μM), VX-809 (3 μM), GP-5 (10 μM), C1+C2 (10 μM) and vehicle control (0.3% DMSO), either alone or in the indicated combinations, were pre-incubated with FRT G542X cells for 48 hours. During the assay the baseline conductance (Gt) was initially determined prior to the acute addition of forskolin (20 μM) and GP-5 (10 μM) to stimulate CFTR activity; the CFTR inhibitor, $CFTR_{Inh}$-172 (10 μM), was added to inhibit CFTR activity at the end of the assay. In FRT G542X cells, VX-809, GP-5 and C1+C2 showed non-significant effects on CFTR stimulation in the presence of forskolin and GP-5, while escin showed significant effects on CFTR stimulation in the presence of forskolin and GP-5. The combination of escin and VX-809 or escin and C1+C2 showed a synergistic interaction as compared to vehicle control in the presence of forskolin and GP-5.

Figure 12B:
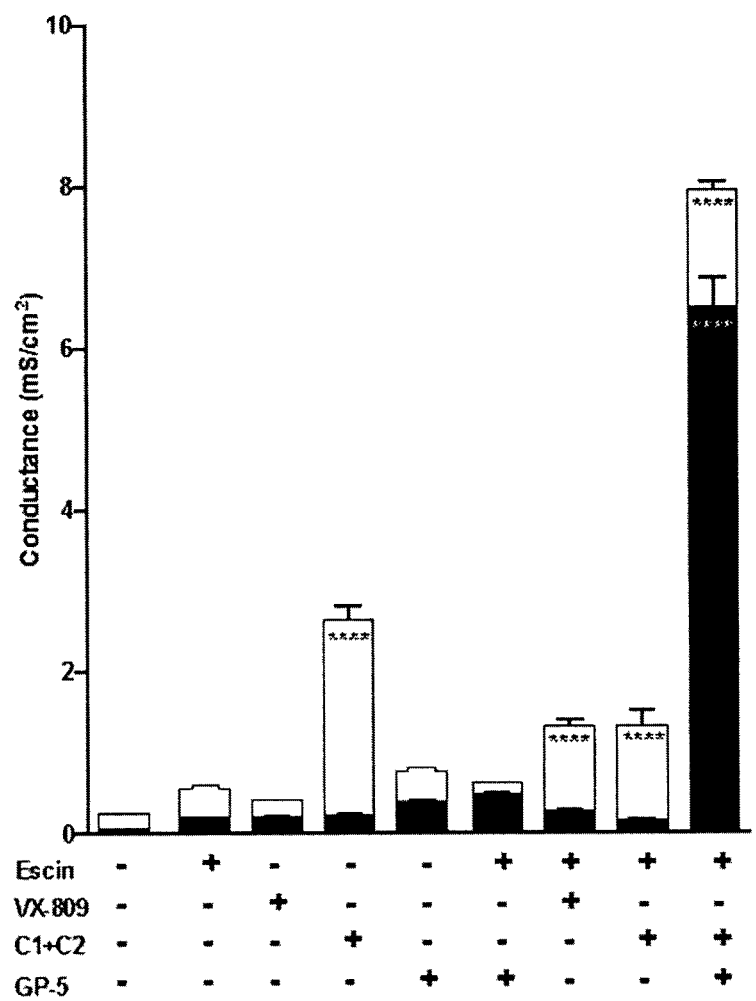
FIG. 12B shows the effect of escin in combination with CFTR potentiators (GP-5) and correctors (VX-809 and the combination of C1 and C2) on conductance in FRT W1282X cells. Escin (10 μM), VX-809 (3 μM), GP-5 (10 μM), C1+C2 (10 μM) and vehicle control (0.3% DMSO), either alone or in the indicated combinations, were pre-incubated with FRT W1282X cells for 48 hours prior to the addition of forskolin (20 μM) or VX-770 (10 μM) for stimulation of CFTR ($*P<0.05$, $P<0.01$, $*P<0.001$, $****P<0.0001$ as compared to vehicle control).

FIG. 12B shows the effect of escin in combination with the CFTR correctors VX-809 and the combination of C1+C2 and the CFTR potentiator GP-5 as well as the effect of escin in combination with all three compounds in FRT W1282X cells. Stimulation of CFTR activity was determined by an increase in CFTR conductance. Escin (10 μM), VX-809 (3 μM), GP-5 (10 μM), C1+C2 (10 μM) and vehicle control (0.3% DMSO), either alone or in the indicated combinations, were pre-incubated with FRT W1282X cells for 48 hours. During the assay the baseline conductance (Gt) was initially determined prior to the acute addition of forskolin (20 μM) and GP-5 (10 μM) to stimulate CFTR activity; the CFTR inhibitor, $CFTRa_{h}$-172 (10 μM), was added to inhibit CFTR activity at the end of the assay. In FRT W1282X cells, escin, VX-809, C1+C2 and GP-5 showed varying stimulatory effects on CFTR stimulation in the presence of forskolin and GP-5, with C1+C2 showing a significant effect on the addition of GP-5. The combination of GP-5 and C1+C2 significantly increased CFTR activity in the presence of forskolin and GP-5. The combination of escin with these compounds in stimulating CFTR activity was then determined. Escin showed a significant increase in CFTR activity when combined with VX-809 and C1+C2 in the presence of GP-5 only and significant increase in CFTR activity when combined with both C1+C2 and GP-5 in the presence of forskolin and GP-5. The combination of escin, C1+C2 and GP-5 showed the greatest stimulation of CFTR activity (in the presence of both forskolin and GP-5) of any of the combinations tested.

These results confirm that compounds of the present disclosure can stimulate read-through of CFTR PTCs and that the combination of CFTR potentiators and activators can further enhance the activity of the read-through stimulating compounds of the present disclosure.

Example 10—Enhanced PTC Read-Through with Escin in Combination with VX-809

The effect of the read-through stimulating compounds of the present disclosure in combination with the CFTR corrector VX-809 was further examined in FRT cells with the G542X, Y122X and W1282X mutations. Enhancement of PTC read-through by the compounds of the present disclosure was determined by an increase in CFTR conductance (FIGS. 13A-13C) or an increase in CFTR protein expression at the cell surface (FIGS. 14A-14C). CFTR conductance also indicated the CFTR was functional as a result of the read-through of the PTC. Escin (10 μM), VX-809 (3 μM), G418 (250 μg/ml) and vehicle control (0.3% DMSO), either alone or in the indicated combinations, were pre-incubated with FRT G542X, -Y122X and -W1282X cells for 48 hours (in this example, forskolin and VX-770/GP-5 were not added prior to determining the effects of the compounds.

Figure 13A:
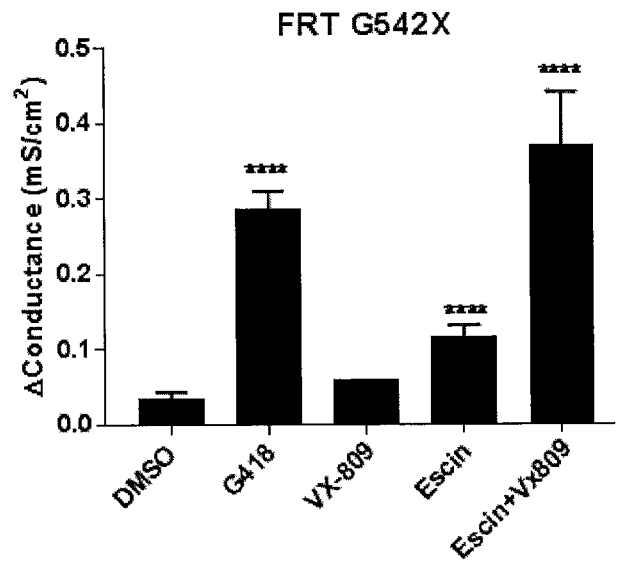
FIG. 13A shows the effect of escin and the CFTR corrector VX-809 on CFTR conductance in FRT G542X cells. Escin (10 μM), VX-809 (3 μM), G418 (250 μg/ml) and vehicle control (0.3% DMSO), either alone or in the indicated combinations, were pre-incubated with FRT G542X cells for 48 hours. During the assay the baseline conductance (Gt) was initially determined prior to the acute addition of forskolin (20 μM) and VX-770 (10 μM) to stimulate CFTR activity ($****P<0.0001$ as compared to vehicle control).
Figure 14A:
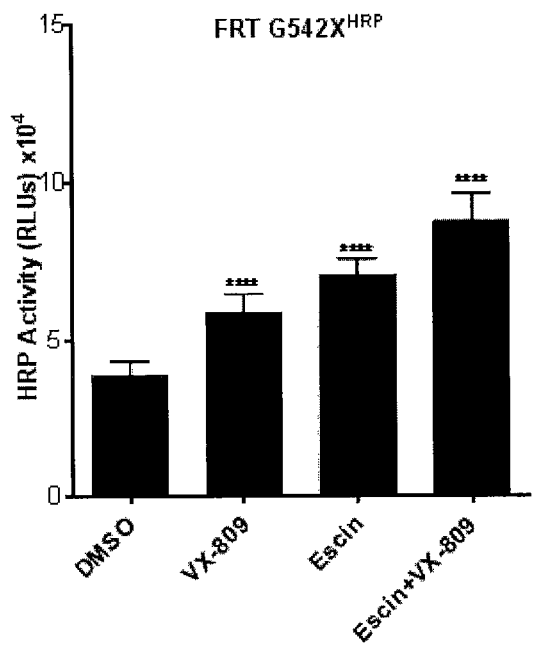
FIG. 14A shows the effect of escin and the CFTR corrector VX-809 on CFTR expression in FRT $G542X^{HRP}$ cells. Escin (10 μM), VX-809 (3 μM) and vehicle control (0.3% DMSO), either alone or in the indicated combinations, were pre-incubated with FRT $G542X^{HRP}$ cells for 48 hours ($****P<0.0001$ as compared to vehicle control).
Figure 14B:
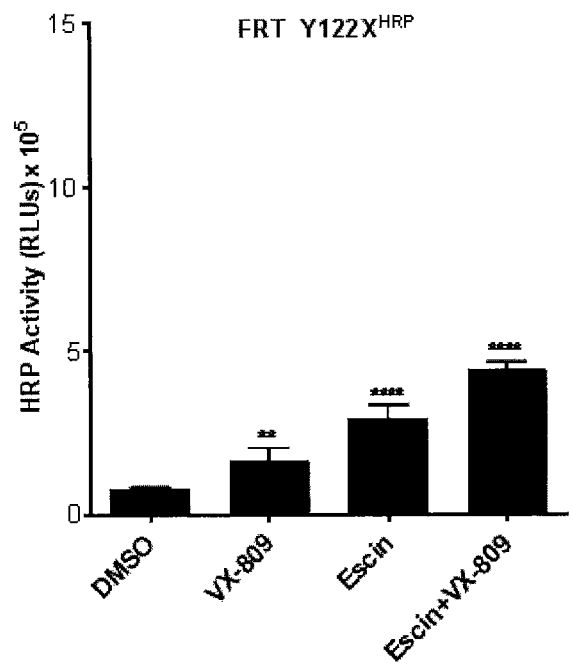
FIG. 14B shows the effect of escin and the CFTR corrector VX-809 on CFTR expression in FRT $Y122X^{HRP}$ cells. Escin (10 μM), VX-809 (3 μM) and vehicle control (0.3% DMSO), either alone or in the indicated combinations, were pre-incubated with FRT $Y122X^{HRP}$ cells for 48 hours ($P<0.01$, $**P<0.0001$ as compared to vehicle control).
Figure 14C:
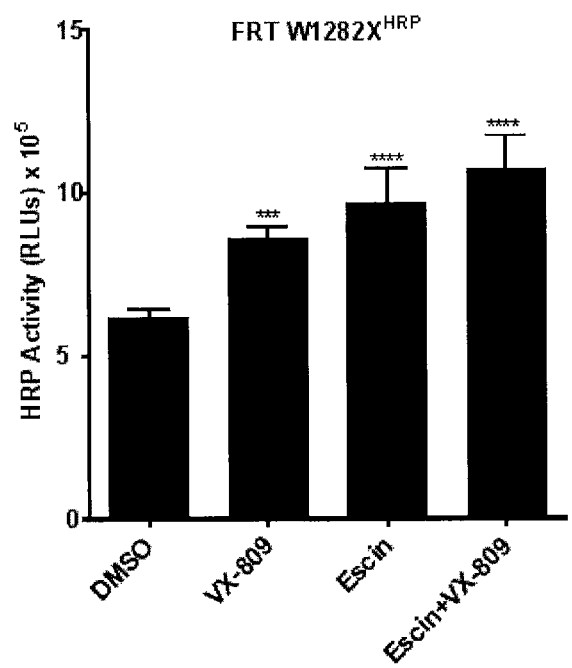
FIG. 14C shows the effect of escin and the CFTR corrector VX-809 on CFTR expression in FRT $W1282X^{HRP}$ cells. Escin (10 μM), VX-809 (3 μM) and vehicle control (0.3% DMSO), either alone or in the indicated combinations, were pre-incubated with FRT $W1282X^{HRP}$ cells for 48 hours ($*P<0.001$, $**P<0.0001$ as compared to vehicle control).

The results are shown in FIGS. 13A and 14A (FRT G542X cells), 13B and 14B (FRT Y122X cells) and 13C and 14C (FRT W1282X cells).

Figure 13B:
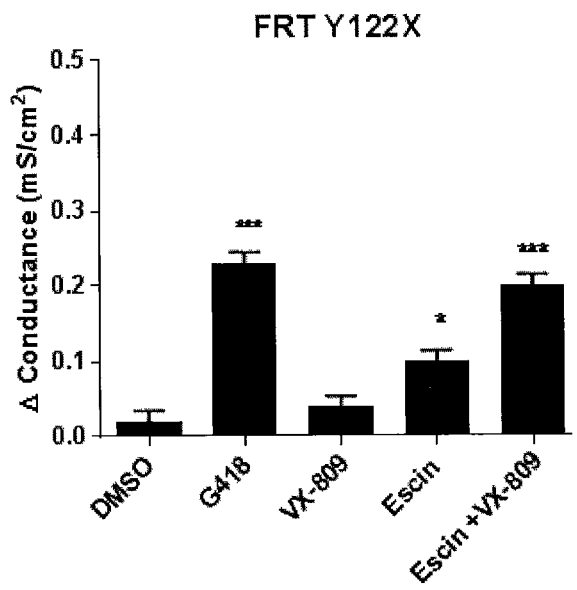
FIG. 13B shows the effect of escin and the CFTR corrector VX-809 on CFTR conductance in FRT Y122X cells. Escin (10 μM), VX-809 (3 μM), G418 (250 μg/ml) and vehicle control (0.3% DMSO), either alone or in the indicated combinations, were pre-incubated with FRT Y122X cells for 48 hours prior the determination of conductance as described in FIG. 13A ($*P<0.05$, $***P<0.001$ as compared to vehicle control).
Figure 13C:
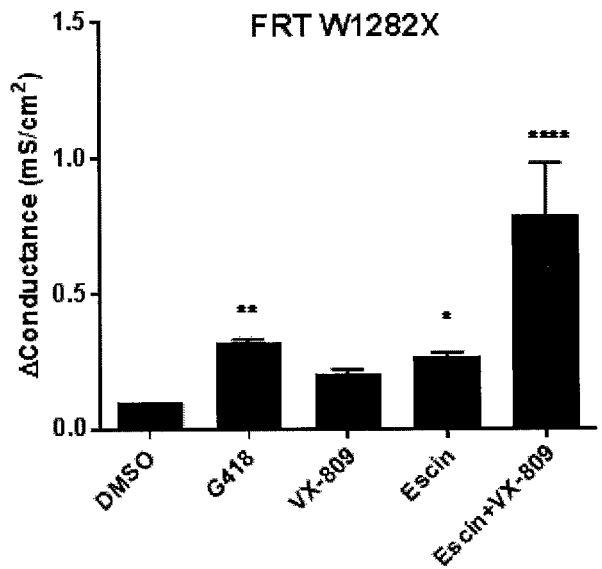
FIG. 13C shows the effect of escin and the CFTR corrector VX-809 on CFTR conductance in FRT W1282X cells. Escin (10 μM), VX-809 (3 μM), G418 (250 μg/ml) and vehicle control (0.3% DMSO), either alone or in the indicated combinations, were pre-incubated with FRT W1282X cells for 48 hours prior to the determination of conductance as described in FIG. 13A ($*P<0.05$, $P<0.01$, $**P<0.0001$ as compared to vehicle control).

In FRT G542X cells, escin and G418 showed significant stimulatory effects on CFTR conductance. The combination of escin and VX-809 showed a synergistic increase in the stimulatory effects on CFTR conductance as compared to VX-809 and escin alone (FIG. 13A). In FRT Y122X cells, escin and G418 showed significant stimulatory effects on CFTR conductance. The combination of escin and VX-809 showed a further increased stimulatory effect on CFTR conductance as compared to VX-809 and escin alone (FIG. 13B). In FRT W1282X cells, escin, and G418 showed significant stimulatory effects on CFTR conductance. The combination of escin and VX-809 showed a synergistic increase in the stimulatory effects on CFTR conductance as compared to VX-809 and escin alone (FIG. 13C).

In FRT G542X$^{HRP}$ cells, escin and VX-809 showed significant stimulatory effects on CFTR protein expression. The combination of escin and VX-809 showed a further increased stimulatory effect on CFTR protein expression as compared to VX-809 and escin alone (FIG. 14A). In FRT Y122X$^{HRP}$ cells, escin and VX-809 showed significant stimulatory effects on CFTR protein expression. The combination of escin and VX-809 showed a further increased stimulatory effect on CFTR protein expression as compared to VX-809 and escin alone (FIG. 14B). In FRT W1282X$^{HRP}$ cells, escin and VX-809 showed significant stimulatory effects on CFTR protein expression. The combination of escin and VX-809 showed a further increased stimulatory effect on CFTR protein expression as compared to VX-809 and escin alone (FIG. 14C).

Additional experiments were conducted in primary HBE cells from a donor with a heterozygous G542X/ΔF508 mutation. Enhancement of PTC read-through by the compounds of the present disclosure was determined by an increase in CFTR Isc. To determine short circuit current (Isc), HBE cells were treated with amiloride (100 µM) to block epithelial sodium channel activity followed by the addition of CFTR agonists FSK (10 µM) and VX-770 (10 µM); CFTR$_{Inh}$-172 (10 µM) was added at the end of the experiment to block CFTR-dependent Isc.

Figure 15A:
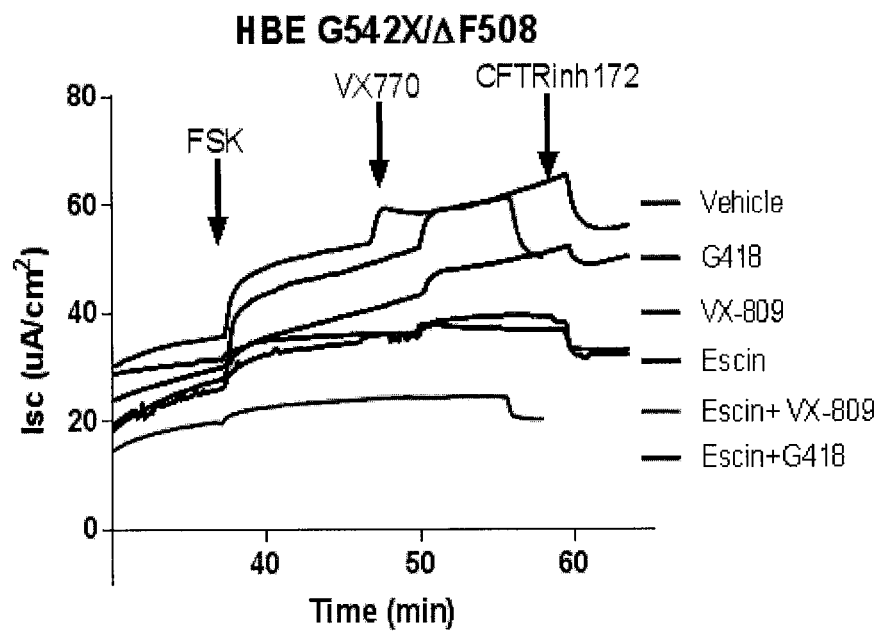
FIG. 15A shows a representative tracing illustrating the effect of escin in combination with the CFTR corrector VX-809 and G418 on Isc in HBE G542X/ΔF508 cells. HBE G542X/ΔF508 cells were treated for 48 hours with escin (10 μM) G418 (250 μg/ml), VX-809 (3 μM) or vehicle control (0.1% DMSO), either alone or in the indicated combinations. Forskolin (10 μM) and VX-770 (10 μM) were added to stimulate CFTR immediately prior to determination of Isc.
Figure 15B:
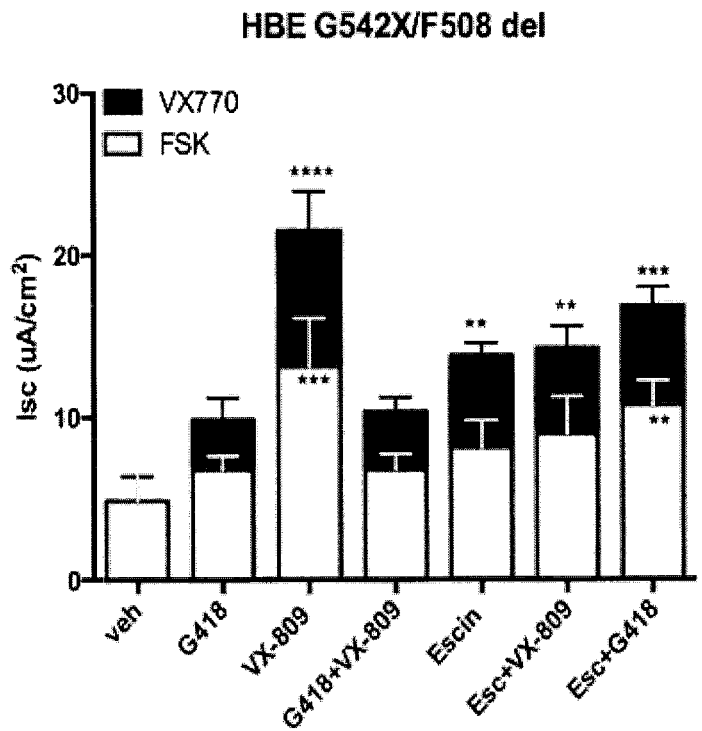
FIG. 15B shows the effect of escin in combination with the CFTR corrector VX-809 and G418 on Isc in HBE G542X/ΔF508 cells. The experimental set-up is the same as described in FIG. 15A ($P<0.01$, $*P<0.001$, $****p<0.0001$ as compared to vehicle control).

FIG. 15A shows a representative tracing on the effects of the tested compounds and combinations on Isc. FIG. 15B shows VX-809 and the combination of escin and G418 significantly increased Isc in the presence of forskolin and VX-809, escin, the combination of escin and VX-809 and the combination of escin and G418 significantly increased Isc in the presence of VX-770.

These results confirm that compounds of the present disclosure can stimulate read-through of CFTR PTCs and that the combination of CFTR potentiators can further enhance the activity of the read-through stimulating compounds of the present disclosure.

Example 11—Escin Stimulates Read-Through of PTCs in Hurler Syndrome

Hurler syndrome is the most severe form of a lysosomal storage disease and is caused by loss of the enzyme α-L-iduronidase (encoded by the IDUA gene). α-L-iduronidase participates in the degradation of glycosaminoglycans (GAGs) within the lysosome. In some populations, PTC mutations represent roughly two-thirds of the mutations that cause Hurler syndrome. Furthermore, even small restorations in α-L-iduronidase activity have been shown to reduce the effects of Hurler Syndrome. The two most common mutations in Hurler syndrome are the Q70X and W402X mutations.

Figure 16A:
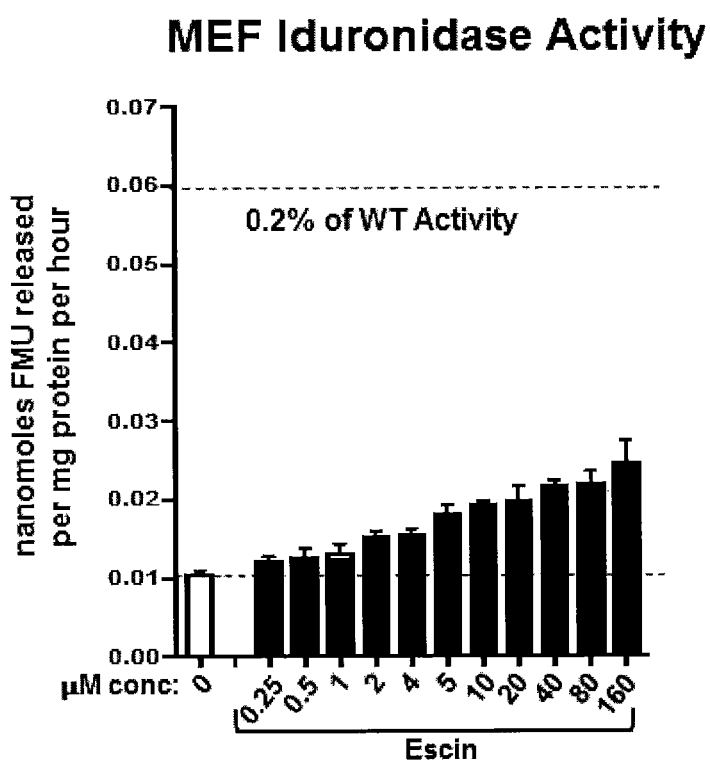
FIG. 16A shows the effect of escin on α-L-iduronidase activity in mouse embryonic fibroblast (MEF) cells derived from homozygous Idua-W402X mice. MEF cells were grown in the presence of escin (0.25 to 160 μM) or vehicle control (0.1% DMSO) for 48 hours. After 48 hours, cell lysates were obtained and the activity of MEF α-L-iduronidase was determined.

To investigate the effect of the read-through stimulating compounds of the present disclosure in Hurler syndrome, immortalized mouse embryonic fibroblasts (MEF) derived from homozygous Idua-W402X mice were grown in the presence of escin (0.25 to 160 µM), doxorubicin (50 to 160 µM) or vehicle control (0.1% DMSO) for 48 hours. After 48 hours, cell lysates were obtained and the activity of MEF α-L-iduronidase was determined. Enhancement of PTC read-through by the compounds of the present disclosure was determined by an increase in α-L-iduronidase activity. The results are shown in FIG. 16A for escin and FIG. 16B for doxorubicin. Dotted line (upper) indicates that a specific activity of 0.06 corresponds to approximately 0.2% of wild-type MEF α-L-iduronidase activity and dotted line (lower) indicates the activity in the presence of vehicle control only.

Escin treatment resulted in a dose-dependent increase in α-L-iduronidase activity as compared to vehicle control (FIG. 16A). Significant increases in α-L-iduronidase activity were seen at escin concentrations as low as 5 to 10 µM. Escin treatment did not significantly decrease total protein significantly, although some decrease in total protein was observed for escin concentrations over 10 µM.

Figure 16B:
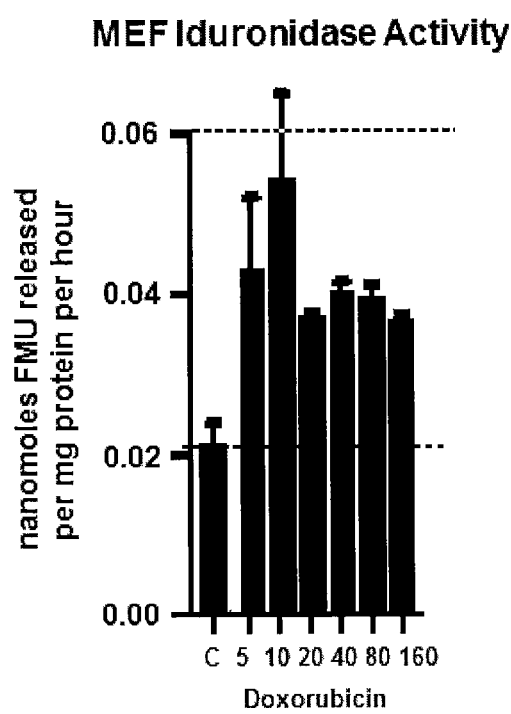
FIG. 16B shows the effect of doxorubicin on α-L-iduronidase activity in mouse embryonic fibroblast (MEF) cells derived from homozygous Idua-W402X mice. MEF cells were grown in the presence of doxorubicin (5.0 to 160 μM) or vehicle control (0.1% DMSO) for 48 hours. After 48 hours, cell lysates were obtained and the activity of MEF α-L-iduronidase was determined.

Doxorubicin treatment resulted in a dose-dependent increase in α-L-iduronidase activity as compared to vehicle control (FIG. 16B). Significant increases in α-L-iduronidase activity were seen at doxorubicin concentrations from 5 to 160 µM, with maximal stimulation being observed at lower doxorubicin concentrations. Doxorubicin treatment did decrease total protein concentrations by about 40% at all concentrations tested.

These results confirm that compounds of the present disclosure can stimulate read-through not only of CFTR PTCs but also PTCs present in other disease as well indicating the broad utility of the compounds of the present disclosure in stimulating read-through of PTC.

What is claimed:

1. A method for treating Hurler syndrome mediated by the presence of a premature termination codon, the method comprising the step of stimulating read-through of the premature termination codon by administering to the subject a therapeutically effective amount of a compound that stimulates the read-through of the premature termination codon in the subject, the compound selected from the group consisting of: escin, a compound of the formula IIa, or a pharmaceutically acceptable salt, hydrate or solvate of any of the foregoing:

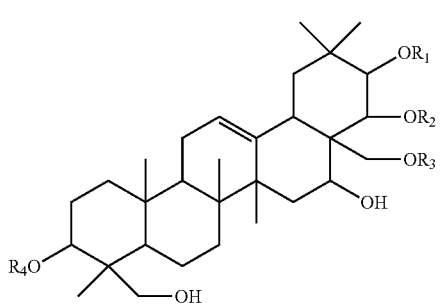

IIa wherein $R_1$, $R_2$ and $R_3$ are each independently selected from the group consisting of: —H, alkyl, alkenyl, alkanoyl and alkenoyl; and $R_4$ is selected from the group consisting of: a linear saccharide chain of 1-11 saccharide units, a branched saccharide chain of 1-11 saccharide units and —H.

2. The method of claim 1, wherein the compound is the compound of formula IIa, or a pharmaceutically acceptable salt, hydrate or solvate thereof.

3. The method of claim 2, wherein $R_1$ is selected from the group consisting of: —H, alkyl, alkenyl, acetyl, hexanoyl, benzoyl, ethylbutyryl, ethanoyl, propionyl, isobutyryl, butyryl, angeloyl, tigoyl, senecioyl, crotonoyl, 3,3-Dimethylartyloyl, cinnamoyl, pentenoyl, 2-propenoyl, (2E)-2-pentenoyl and 4-pentenoyl;

$R_2$ is acetyl or —H; and $R_3$ is —H or acetyl.

4. The method of claim 2, wherein $R_1$ is selected from the group consisting of: angeloyl and tigoyl;

$R_2$ is acetyl; and $R_3$ is —H.

5. The method of claim 2, wherein $R_1$ is selected from the group consisting of: angeloyl, and tigoyl;

$R_2$ is —H; and $R_3$ is acetyl.

6. The method of claim 2, wherein $R_4$ is:

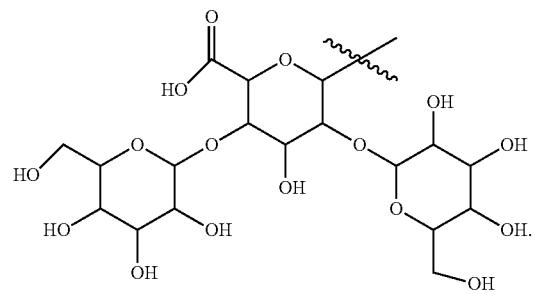 [SMILES: *C1OC(C(=O)O)C(OC2OC(CO)C(O)C(O)C2O)C(O)C1OC1OC(CO)C(O)C(O)C1O]

7. The method of claim 2, wherein the compound has the formula Ia:

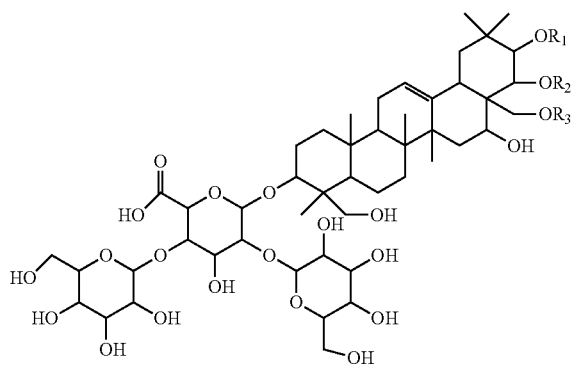

Ia wherein:

$R_1$ is selected from the group consisting of: angeloyl and tigoyl;

$R_2$ is selected from the group consisting of: acetyl and —H; and $R_3$ is selected from the group consisting of: acetyl and —H.

8. The method of claim 7, wherein $R_1$ is tigoyl, $R_2$ is acetyl and $R_3$ is —H, $R_1$ is angeloyl, $R_2$ is acetyl and $R_3$ is —H, $R_1$ is tigoyl, $R_2$ is —H and $R_3$ is acetyl, $R_1$ is angeloyl, $R_2$ is —H and $R_3$ is acetyl or a combination of the foregoing.

9. The method of claim 1, wherein the administering increases the stability of a mRNA containing the premature termination codon.

10. The method of claim 1, wherein the premature termination codon is selected from the group consisting of: W402X, Q70X, R628X, Q148X, E404X, Y343X and Q548X.

11. The method of claim 1 further comprising administering a secondary agent to the subject.

12. The method of claim 11, wherein the secondary agent is an NMD inhibitor, a histone deacetylase inhibitor combination of the foregoing.

13. A method for pharmacologically suppressing a premature termination codon associated with Hurler syndrome in a subject, the method comprising the step of stimulating read-through of the premature termination codon by administering to the subject a therapeutically effective amount of a compound that stimulates the read-through of the premature termination codon associated with Hurler syndrome in the subject, the compound selected from the group consisting of: escin, a compound of the formula IIa, or a pharmaceutically acceptable salt, hydrate or solvate of any of the foregoing:

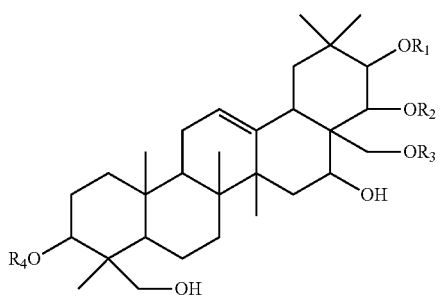

IIa wherein
$R_1$, $R_2$ and $R_3$ are each independently selected from the group consisting of: —H, alkyl, alkenyl, alkanoyl and alkenoyl; and
$R_4$ is selected from the group consisting of: a linear saccharide chain of 1-11 saccharide units, a branched saccharide chain of 1-11 saccharide units and —H.

14. The method of claim 13, wherein the compound is the compound of formula IIa, or a pharmaceutically acceptable salt, hydrate or solvate thereof.

15. The method of claim 14, wherein
$R_1$ is selected from the group consisting of: —H, alkyl, alkenyl, acetyl, hexanoyl, benzoyl, ethylbutyryl, ethanoyl, propionyl, isobutyryl, butyryl, angeloyl, tigoyl, senecioyl, crotonoyl, 3,3-Dimethylartyloyl, cinnamoyl, pentenoyl, 2-propenoyl, (2E)-2-pentenoyl and 4-pentenoyl;
$R_2$ is acetyl or —H; and
$R_3$ is —H or acetyl.

16. The method of claim 14, wherein
$R_1$ is selected from the group consisting of: angeloyl and tigoyl;
$R_2$ is acetyl; and
$R_3$ is —H.

17. The method of claim 14, wherein
$R_1$ is selected from the group consisting of: angeloyl, and tigoyl;
$R_2$ is —H; and
$R_3$ is acetyl.

18. The method of claim 14, wherein $R_4$ is:

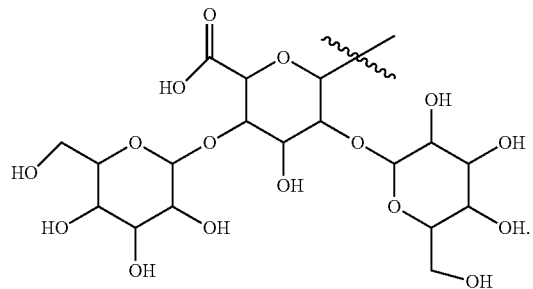

19. The method of claim 14, wherein the compound has the formula:

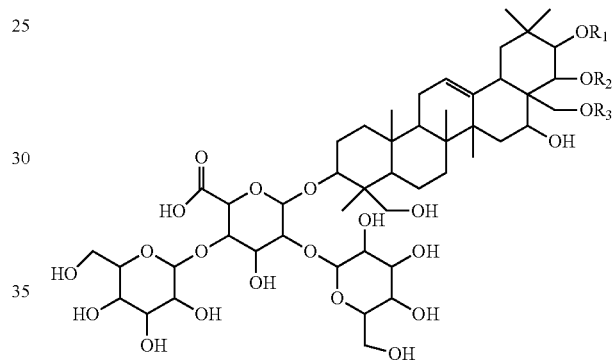

wherein:
$R_1$ is selected from the group consisting of: angeloyl and tigoyl;
$R_2$ is selected from the group consisting of: acetyl and —H; and
$R_3$ is selected from the group consisting of: acetyl and —H.

20. The method of claim 19, wherein $R_1$ is tigoyl, $R_2$ is acetyl and $R_3$ is —H, $R_1$ is angeloyl, $R_2$ is acetyl and $R_3$ is —H, $R_1$ is tigoyl, $R_2$ is —H and $R_3$ is acetyl, $R_1$ is angeloyl, $R_2$ is —H and $R_3$ is acetyl or a combination of the foregoing.

21. The method of claim 13, wherein the administering increases the stability of a mRNA containing the premature termination codon.

22. The method of claim 13, wherein the premature termination codon is selected from the group consisting of: W402X, Q70X, R628X, Q148X, E404X, Y343X and Q548X.

23. The method of claim 13 further comprising administering a secondary agent to the subject.

24. The method of claim 23, wherein the secondary agent is an NMD inhibitor, a histone deacetylase inhibitor combination of the foregoing.

* * * * *